(12) United States Patent
Abrams et al.

(10) Patent No.: US 10,675,295 B2
(45) Date of Patent: Jun. 9, 2020

(54) COMPOSITIONS AND METHODS FOR INHIBITING HMGB1 EXPRESSION

(71) Applicant: Dicerna Pharmaceuticals, Inc., Cambridge, MA (US)

(72) Inventors: Marc Abrams, Cambridge, MA (US); Girish Chopda, Cambridge, MA (US); Jihye Park, Cambridge, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 16/024,355

(22) Filed: Jun. 29, 2018

(65) Prior Publication Data

US 2019/0000870 A1 Jan. 3, 2019

Related U.S. Application Data

(60) Provisional application No. 62/526,971, filed on Jun. 29, 2017.

(51) Int. Cl.
*A61K 31/7125* (2006.01)
*C12N 15/113* (2010.01)

(52) U.S. Cl.
CPC ...... *A61K 31/7125* (2013.01); *C12N 2310/11* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | | | |
|---|---|---|---|---|
| 7,250,496 B2 * | 7/2007 | Bentwich | ............... | G16B 20/00 536/23.1 |
| 8,178,503 B2 * | 5/2012 | Rigoutsos | ............... | G16B 30/00 514/44 A |
| 9,278,108 B2 | 3/2016 | Takenaka et al. | | |
| 2009/0169546 A1 | 7/2009 | Wu et al. | | |
| 2015/0247149 A1 | 9/2015 | Feldstein et al. | | |

FOREIGN PATENT DOCUMENTS

| | | | | |
|---|---|---|---|---|
| WO | WO-2016057932 A1 * | 4/2016 | ..... | C12Y 101/01027 |
| WO | 2017079227 A1 | 5/2017 | | |

OTHER PUBLICATIONS

Chen et al., "Emerging role of high-mobility group box 1 (HMGB1) in liver diseases", Molecular Medicine, 2013, vol. 19, No. 1, pp. 357-366.
Ge et al., "Inhibition of high-mobility group box 1 expression by siRNA in rat hepatic stellate cells", World Journal of Gastroenterology, 2011, vol. 17, No. 36, pp. 4090-4098.
Hirschfield et al., "Pathogenesis of Cholestatic Liver Disease and Therapeutic Approaches", Gastroenterology, 2010, vol. 139, No. 5, pp. 1481-1496.
International Search Report and Written Opinion issued by the United States Patent Office as International Searching Authority for International Application No. PCT/US2018/40410, dated Nov. 2, 2018.
Perazzoli et al., "Gallic Acid and Dodecyl Gallate Prevents Carbon Tetrachloride-Induced Acute and Chronic Hepatotoxicity by Enhancing Hepatic Antioxidant Status and Increasing p53 Expression", Biological and Pharmaceutical Bulletin, 2017, vol. 40, No. 4, pp. 425-434.
Zeng et al., "Inhibition of HMGB1 release via salvianolic acid B-mediated SIRT1 up-regulation protects rats against non-alcoholic fatty liver disease", Scientific Reports, 2015, vol. 5, No. 1, pp. 1-13.

* cited by examiner

*Primary Examiner* — Tracy Vivlemore
(74) *Attorney, Agent, or Firm* — Byron V. Olsen; Dechert LLP

(57) ABSTRACT

This disclosure relates to oligonucleotides, compositions and methods useful for reducing HMGB1 expression, particularly in hepatocytes. Disclosed oligonucleotides for the reduction of HMGB1 expression may be double-stranded or single-stranded, and may be modified for improved characteristics such as stronger resistance to nucleases and lower immunogenicity. Disclosed oligonucleotides for the reduction of HMGB1 expression may also be designed to include targeting ligands to target a particular cell or organ, such as the hepatocytes of the liver, and may be used to treat liver fibrosis and related conditions.

20 Claims, 48 Drawing Sheets

Specification includes a Sequence Listing.

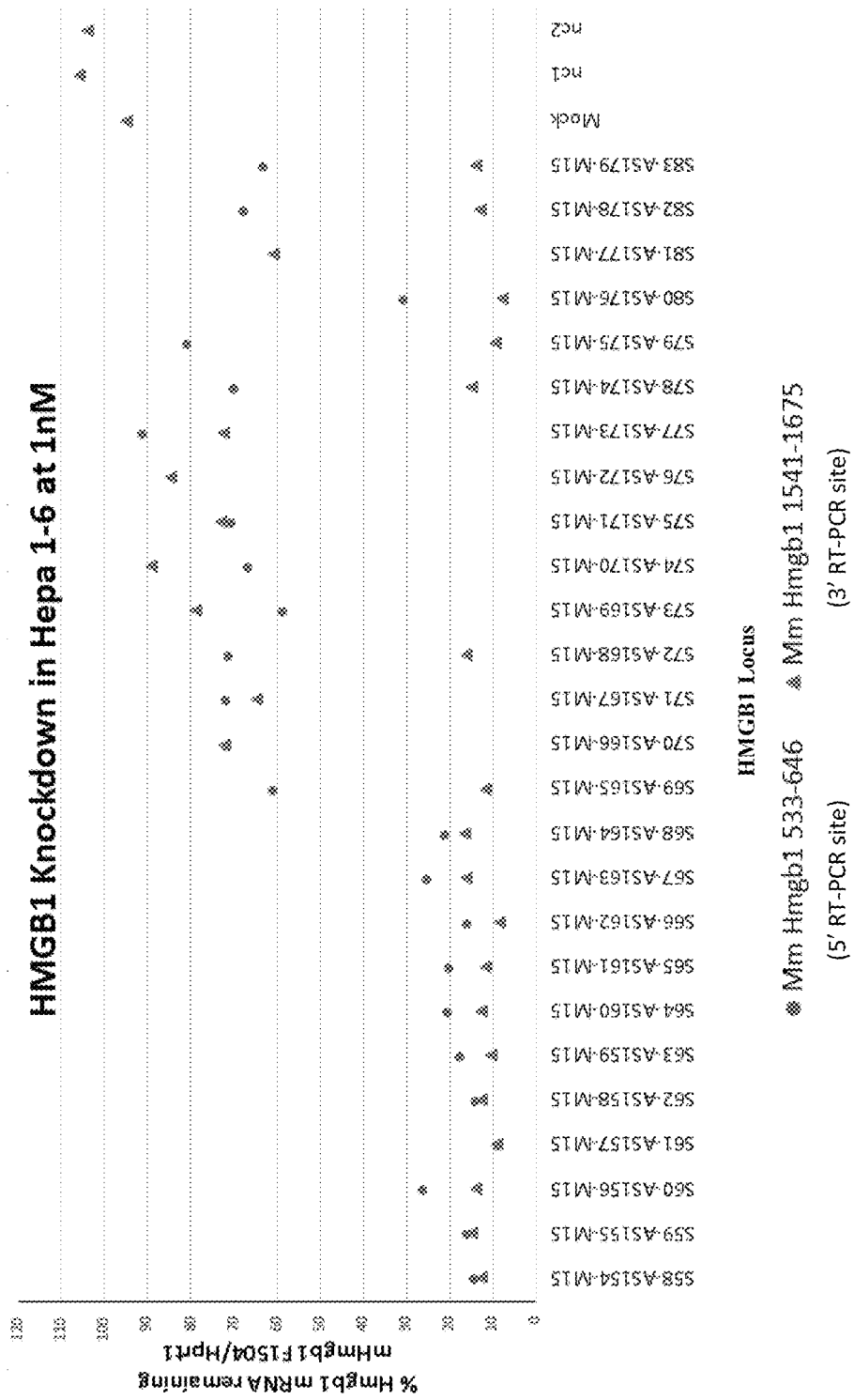

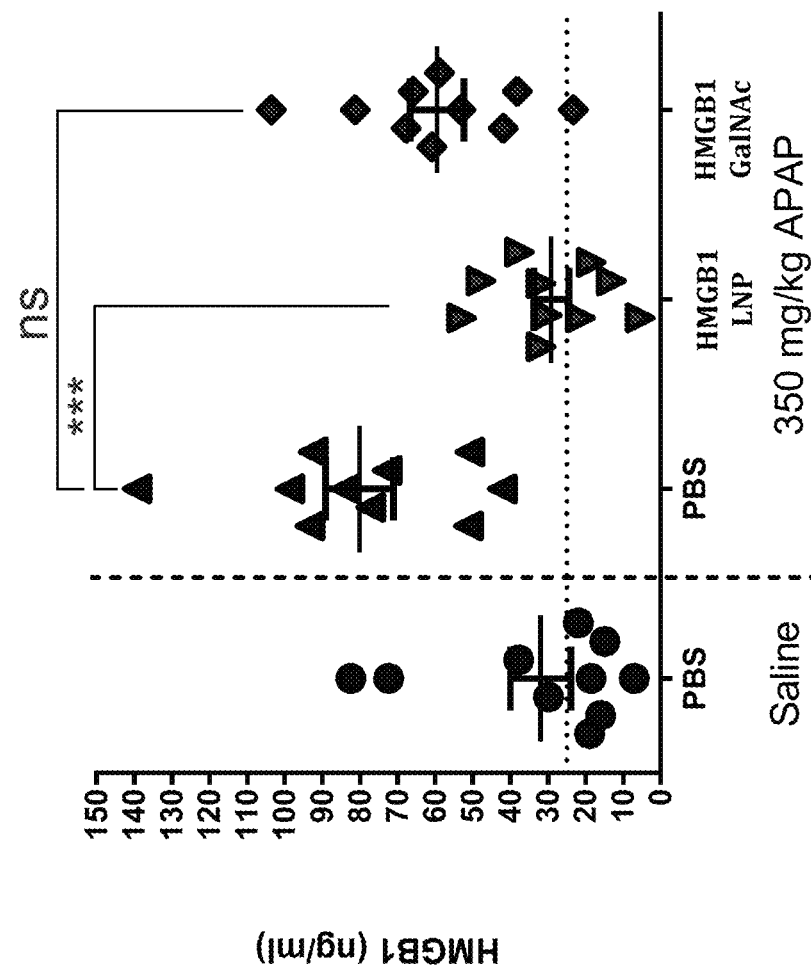

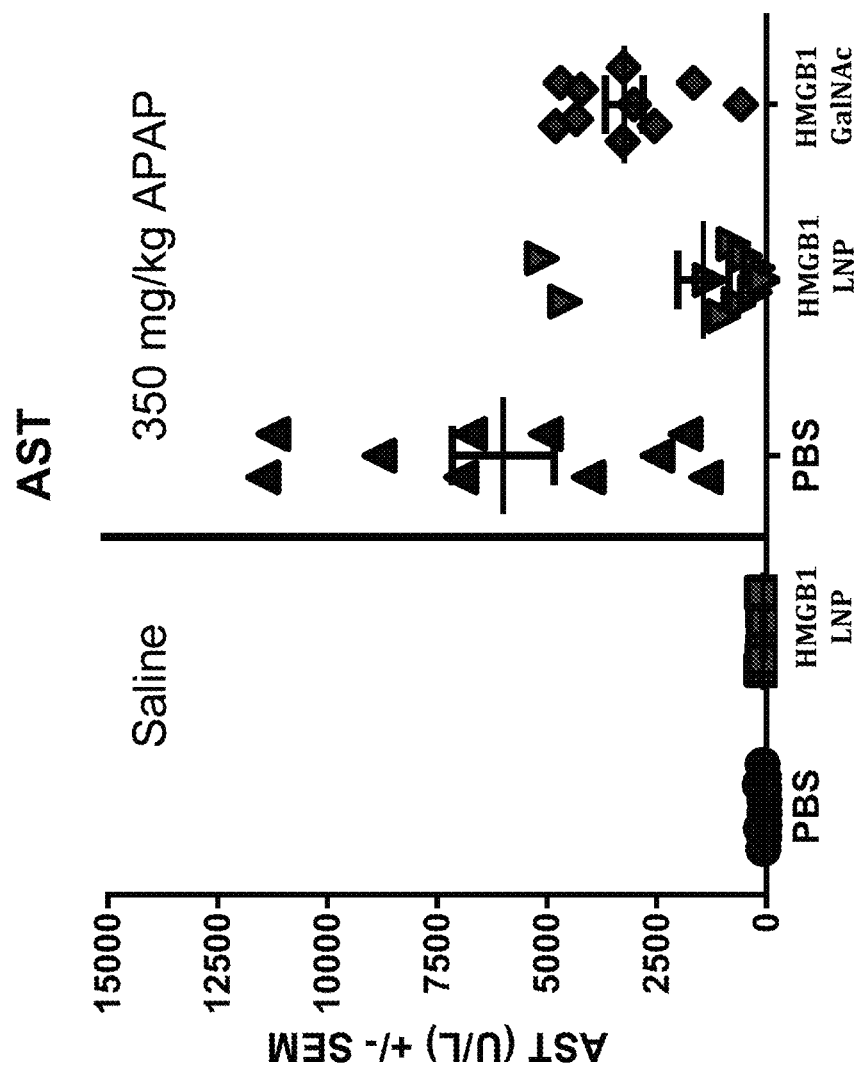

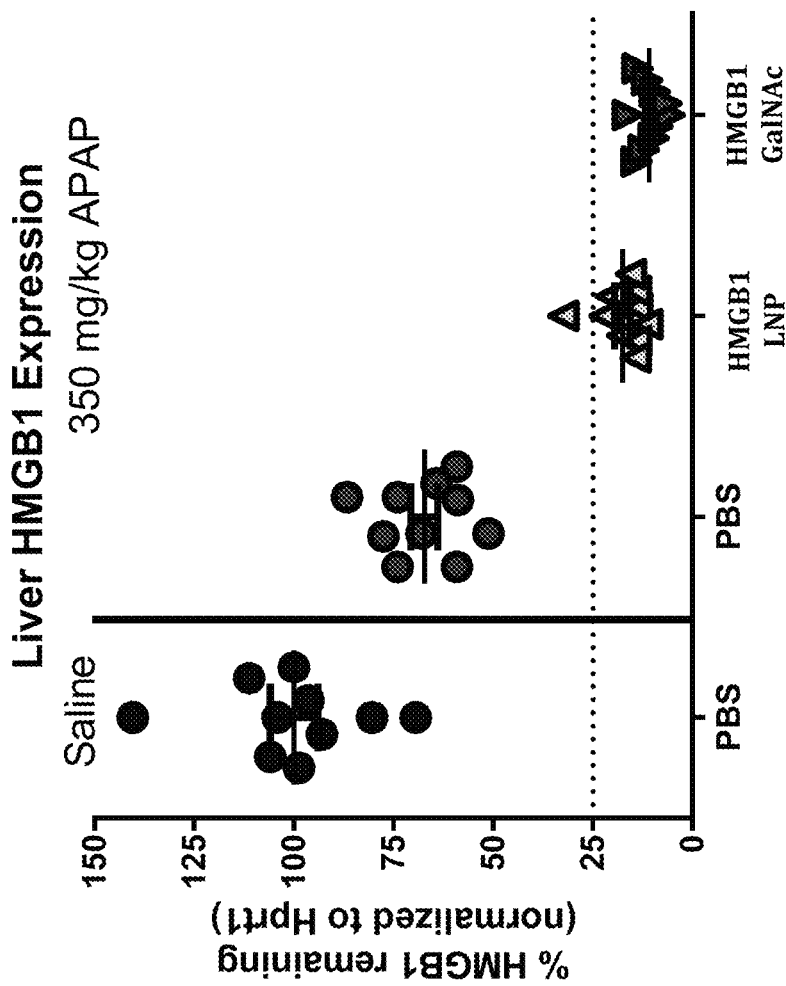

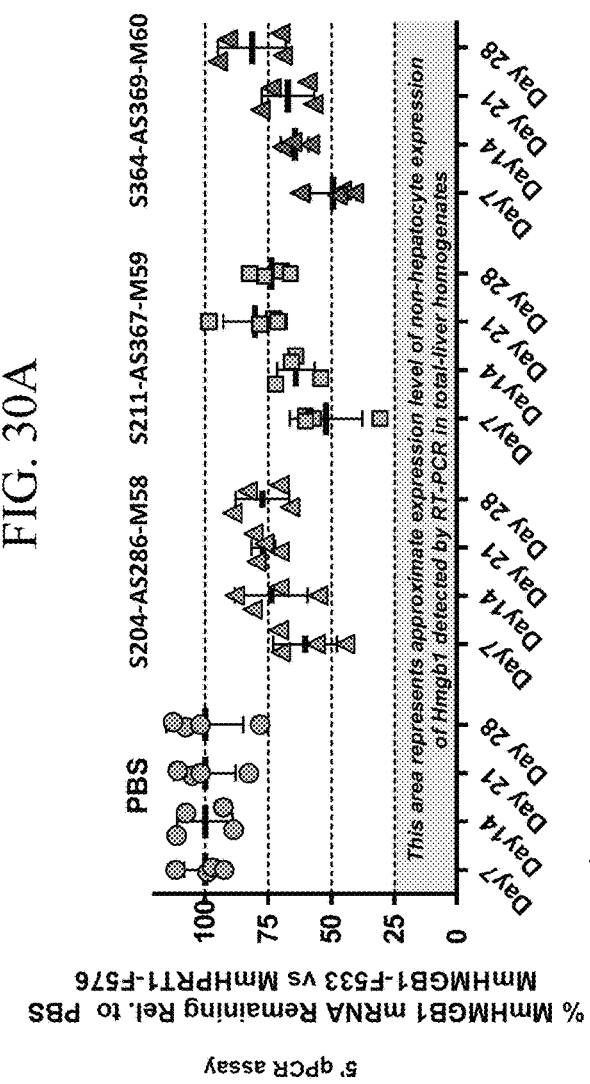
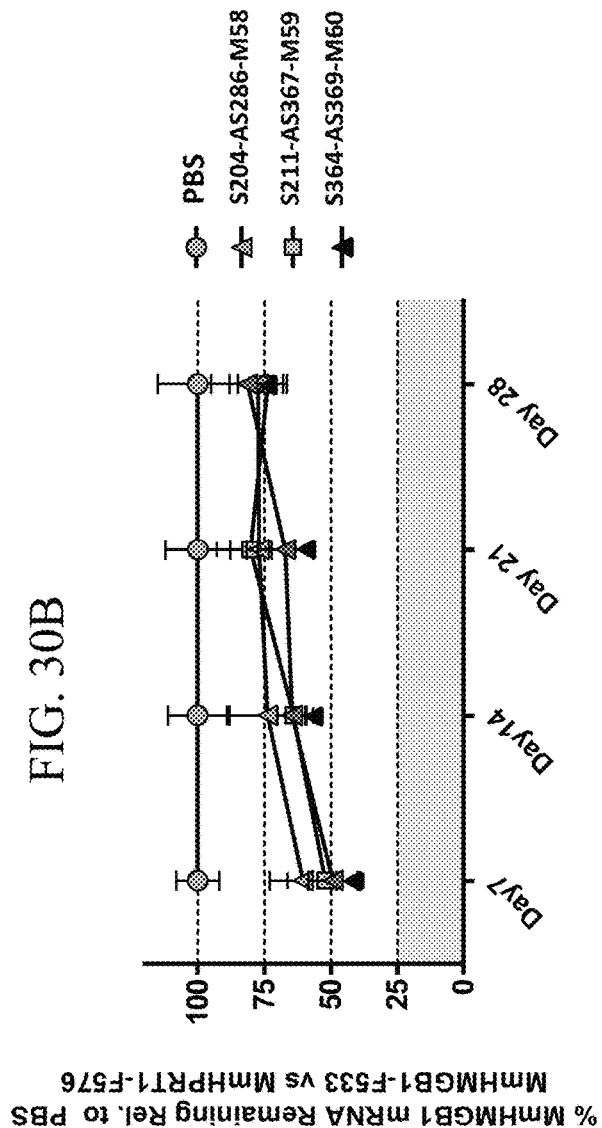
FIG. 30A
FIG. 30B

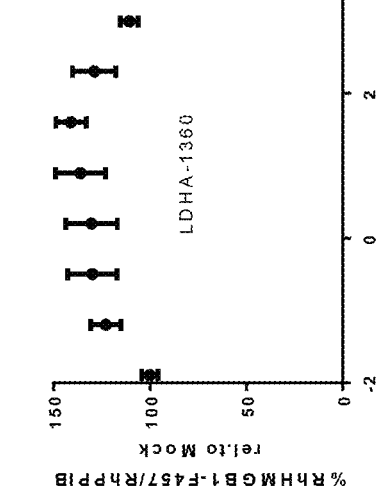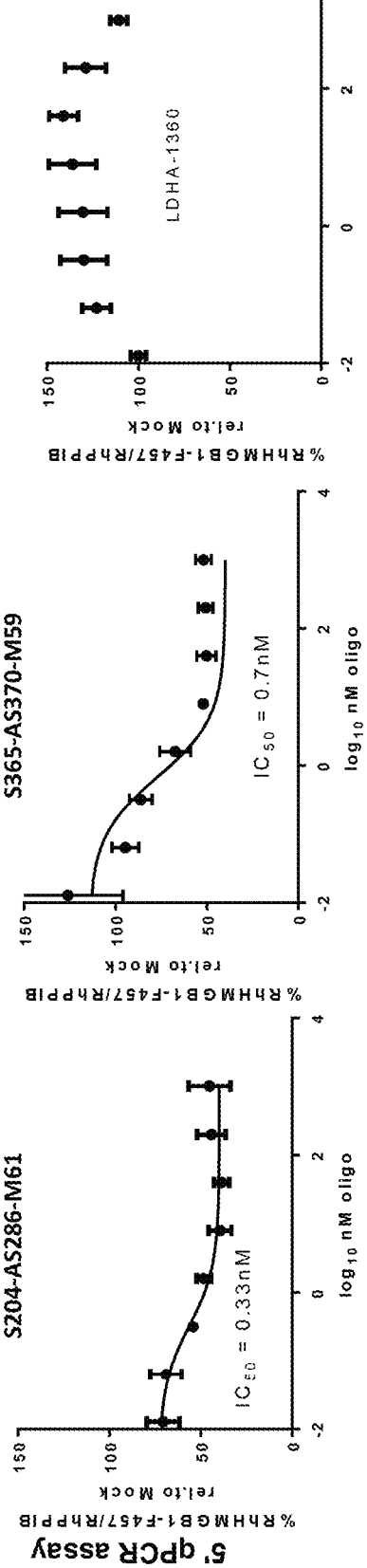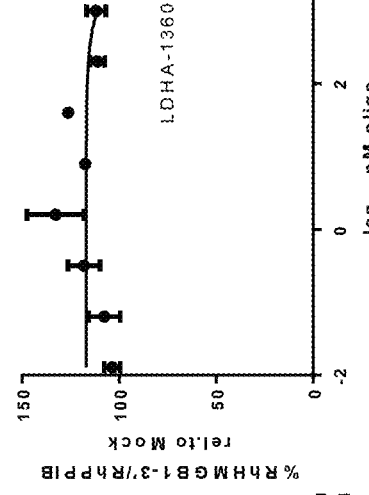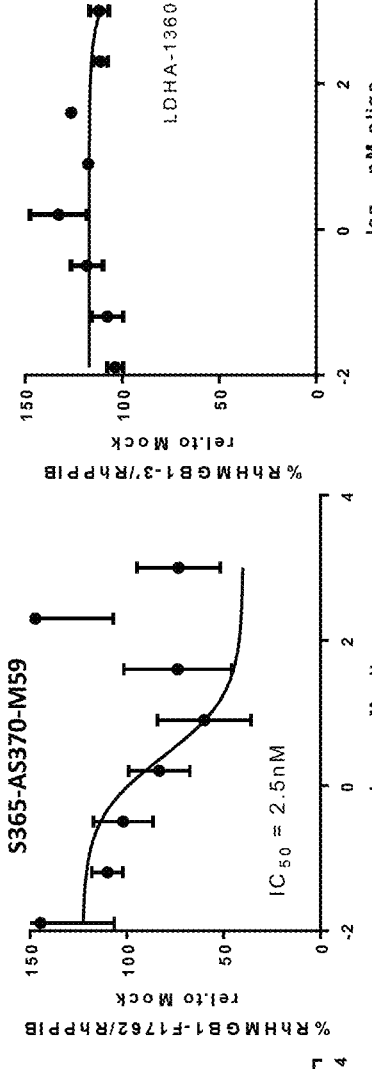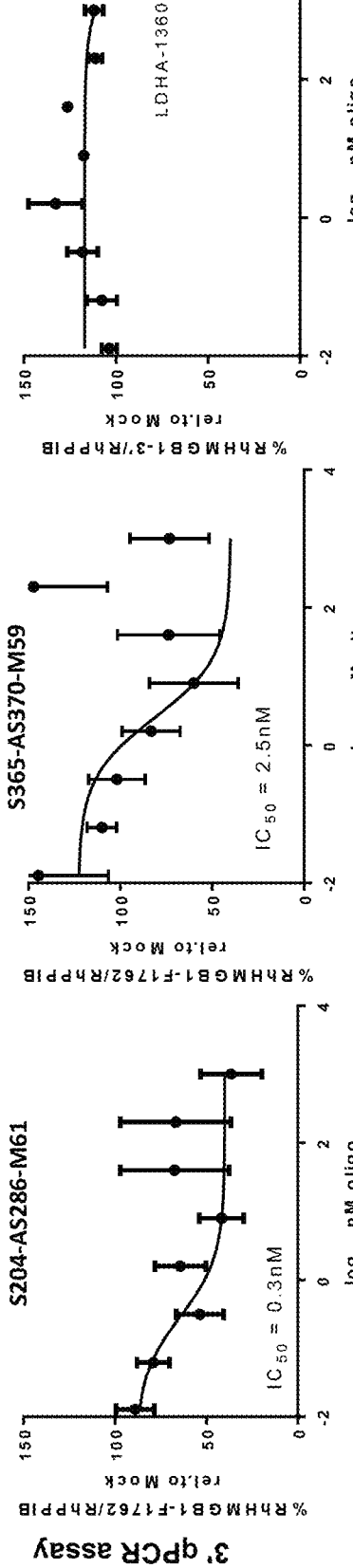

COMPOSITIONS AND METHODS FOR INHIBITING HMGB1 EXPRESSION

RELATED APPLICATIONS

This application claims the benefit of the filing date under 35 U.S.C. § 119 of U.S. Provisional Application Ser. No. 62/526,971, filed Jun. 29, 2017, and entitled "COMPOSITIONS AND METHODS FOR INHIBITING HMGB1 EXPRESSION", the entire contents of which are incorporated herein by reference.

FIELD OF THE INVENTION

The present application relates to oligonucleotides and uses thereof, particularly uses relating to the treatment of conditions involving fibrosis.

REFERENCE TO THE SEQUENCE LISTING

The present application is being filed along with a Sequence Listing in electronic format. The Sequence Listing is provided as a file entitled D0800.70002US01-SEQ.txt created on Jun. 28, 2018 which is 85 kilobytes in size. The information in electronic format of the sequence listing is incorporated herein by reference in its entirety.

BACKGROUND OF THE INVENTION

Tissue fibrosis is a condition characterized by an abnormal accumulation of extracellular matrix and inflammatory factors that result in scarring and promote chronic organ injury. In liver, fibrosis is a multi-cellular response to hepatic injury that can lead to cirrhosis and hepatocellular cancer. The response is often triggered by liver injury associated with conditions such as alcohol abuse, viral hepatitis, metabolic diseases, and liver diseases, such as a cholestatic liver disease, nonalcoholic fatty liver disease (NAFLD) and nonalcoholic steatohepatitis (NASH). Studies have implicated high mobility group box 1 (HMGB1) protein as having a pro-fibrotic role in liver fibrosis. (See, e.g., Li L-C, et al., Emerging role of HMGB1 in fibrotic diseases, J. Cell. Mol. Med. Vol 18, No 12, 2014 pp. 2331-2339) HMGB1 is a nuclear protein released from injured cells that functions as a proinflammatory mediator and has been shown to recruit hepatic stellate cells and liver endothelial cells to sites of liver injury. (Seo, Y S, et al., HMGB1 recruits hepatic stellate cells and liver endothelial cells to sites of ethanol-induced parenchymal cell injury, Am J Physiol Gastrointest Liver Physiol 305: G838-G848, 2013.) Hepatic stellate cells are believed to play a central role in the progression of liver fibrosis through their transformation into proliferative myofibroblastic cells that promote fibrogenic activity in the liver. (See, Kao Y H, et al. High-mobility group box 1 protein activates hepatic stellate cells in vitro. Transplant Proc. 2008; 40: 2704-5)

BRIEF SUMMARY OF THE INVENTION

Aspects of the disclosure relate to compositions and methods for treating fibrosis (e.g., liver fibrosis) in a subject. In some embodiments, potent RNAi oligonucleotides have been developed for selectively inhibiting HMGB1 expression. Accordingly, in some embodiments, RNAi oligonucleotides provided herein are useful for reducing HMGB1 expression, particularly in hepatocytes, and thereby decreasing or preventing fibrosis (see, e.g., Examples 2-4; FIGS. 14A-C, 17A-D, 19, and 22-27). In some embodiments, RNAi oligonucleotides incorporating nicked tetraloop structures are conjugated with GalNAc moieties to facilitate delivery to liver hepatocytes (through interactions with asialoglycoprotein receptor, which is primarily expressed on the surface of hepatocytes) to inhibit HMGB1 expression for the treatment of liver fibrosis. In some embodiments, methods are provided herein involving the use of RNAi oligonucleotides for treating subjects having or suspected of having liver conditions such as, for example, cholestatic liver disease, nonalcoholic fatty liver disease (NAFLD) and nonalcoholic steatohepatitis (NASH). In further embodiments, the disclosure is based on an identification of key regions (referred to as hotspots) of HMGB1 mRNA that are particularly amenable to targeting using oligonucleotide-based approaches. Accordingly, in some embodiments, oligonucleotides have been developed that target these mRNA hotspots to inhibit HMGB1 expression to treat fibrosis.

One aspect of the present disclosure provides oligonucleotides for reducing expression of HMGB1. In some embodiments, the oligonucleotides comprise an antisense strand comprising a sequence as set forth in any one of SEQ ID NOs: 97-192, 273-362, and 366-370. In some embodiments, the antisense strand consists of a sequence as set forth in any one of SEQ ID NOs: 97-192, 273-362, and 366-370. In some embodiments, the antisense strand comprises, or consists of, a sequence as set forth in any one of SEQ ID NOs: 273-362, and 366-370. In some embodiments, the antisense strand comprises, or consists of, a sequence as set forth in SEQ ID NO: 286, 367, 369, or 370. In some embodiments, the oligonucleotides further comprise a sense strand that comprises a sequence as set forth in any one of SEQ ID NOs: 1-96, 193-272, and 363-365. In some embodiments, the sense strand consists of a sequence as set forth in any one of SEQ ID NOs: 1-96, 193-272, and 363-365. In some embodiments, the sense strand comprises, or consists of, a sequence as set forth in any one of SEQ ID NOs: 193-272 and 363-365. In some embodiments, the sense strand comprises, or consists of, a sequence as set forth in SEQ ID NO: 204, 211, 364, 365.

One aspect of the present disclosure provides oligonucleotides for reducing expression of HMGB1, in which the oligonucleotides comprise an antisense strand of 15 to 30 nucleotides in length. In some embodiments, the antisense strand has a region of complementarity to a target sequence of HMGB1 as set forth in any one of SEQ ID NOs: 374-381. In some embodiments, the region of complementarity is at least 15, at least 16, at least 17, at least 18, at least 19, at least 20, at least 21, or at least 22 contiguous nucleotides in length. In some embodiments, the region of complementarity is fully complementary to the target sequence of HMGB1. In some embodiments, the region of complementarity to HMGB1 is at least 19 contiguous nucleotides in length.

In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the antisense strand is 27 nucleotides in length and the sense strand is 25 nucleotides in length. In some embodiments, the duplex region is at least 15, at least 16, at least 17, at least 18, at least 19, at least 20, or at least 21 nucleotides in length. In some embodiments, the antisense strand and sense strand form a duplex region of 25 nucleotides in length.

In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide further comprises a 3'-overhang sequence on the antisense strand of two nucleotides in length. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

In some embodiments, the sense strand comprises a sequence as set forth in any one of SEQ ID NOs: 1-96, 193-272, and 363-365. In some embodiments, the sense strand consists of a sequence as set forth in any one of SEQ ID NOs: 1-96, 193-272, and 363-365. In some embodiments, the antisense strand comprises a sequence as set forth in any one of SEQ ID NOs: 97-192, 273-362, and 366-370. In some embodiments, the antisense strand consists of a sequence as set forth in any one of SEQ ID NOs: 97-192, 273-362, and 366-370.

In some embodiments, the sense strand comprises at its 3'-end a stem-loop set forth as: S1-L-S2, in which S1 is complementary to S2, and in which L forms a loop between S1 and S2 of 3 to 5 nucleotides in length.

Another aspect of the present disclosure provides an oligonucleotide for reducing expression of HMGB1, the oligonucleotide comprising an antisense strand and a sense strand, in which the antisense strand is 21 to 27 nucleotides in length and has a region of complementarity to HMGB1, in which the sense strand comprises at its 3'-end a stem-loop set forth as: S1-L-S2, in which S1 is complementary to S2, and in which L forms a loop between S1 and S2 of 3 to 5 nucleotides in length, and in which the antisense strand and the sense strand form a duplex structure of at least 19 nucleotides in length but are not covalently linked (see, e.g., FIG. 2). In some embodiments, the region of complementarity is fully complementary to at least 15, at least 16, at least 17, at least 18, at least 19, at least 20, or at least 21 contiguous nucleotides of HMGB1 mRNA. In some embodiments, L is a tetraloop. In some embodiments, L is 4 nucleotides in length. In some embodiments, L comprises a sequence set forth as GAAA.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in a decreased level or prevention of liver fibrosis. In some embodiments, expression of HMGB1 protein is reduced by administering to the subject an oligonucleotide disclosed herein. In some embodiments, a subject has cholestatic or autoimmune liver disease.

Another aspect of the present disclosure provides a method of treating a subject having or at risk of having liver fibrosis. In some embodiments, methods provided herein comprise administering to the subject an oligonucleotide that reduces expression of HMGB1. In some embodiments, the subject has cholestatic or autoimmune liver disease. In some embodiments, the subject has nonalcoholic steatohepatitis (NASH). In some embodiments, the oligonucleotide administered to the subject is an RNAi oligonucleotide.

In some embodiments, an oligonucleotide is administered prior to exposure of a subject to a hepatotoxic agent. In some embodiments, an oligonucleotide is administered subsequent to exposure of a subject to a hepatotoxic agent. In some embodiments, the oligonucleotide is administered simultaneously with a subject's exposure to a hepatotoxic agent.

Another aspect of the present disclosure provides a method of treating a subject having or at risk of having nonalcoholic steatohepatitis (NASH). In some embodiments, the method comprises administering to the subject an oligonucleotide that reduces expression of HMGB1 in the subject.

In some embodiments, administration of an oligonucleotide disclosed herein results in a reduction in liver HMGB1 levels. In some embodiments, administration of an oligonucleotide disclosed herein results in a reduction in serum HMGB1 levels.

Another aspect of the present disclosure provides an oligonucleotide for reducing expression of HMGB1, in which oligonucleotide comprises a sense strand of 15 to 50 nucleotides in length and an antisense strand of 15 to 30 nucleotides in length, in which the sense strand forms a duplex region with the antisense strand, in which the sense strand comprises a sequence as set forth in any one of SEQ ID NO: 1-96, and in which the antisense strand comprises a complementary sequence selected from SEQ ID NO: 97-192. In some embodiments, the sense strand consists of a sequence as set forth in any one of SEQ ID NO: 1-96. In some embodiments, the antisense strand consists of a complementary sequence selected from SEQ ID NO: 97-192.

Another aspect of the present disclosure provides an oligonucleotide for reducing expression of HMGB1, in which oligonucleotide comprising a sense strand of 15 to 50 nucleotides in length and an antisense strand of 15 to 30 nucleotides in length, in which the sense strand forms a duplex region with the antisense strand, in which the sense strand comprises a sequence as set forth in any one of SEQ ID NO: 193-272 or 363-365 and in which the antisense strand comprises a complementary sequence selected from SEQ ID NO: 273-362 or 366-370. In some embodiments, the sense strand consists of a sequence as set forth in any one of SEQ ID NO: 193-272 or 363-365. In some embodiments, the antisense strand consists of a complementary sequence selected from SEQ ID NO: 273-362 or 366-370.

Another aspect of the present disclosure provide an oligonucleotide for reducing expression of HMGB1, in which the oligonucleotide comprises a sense strand of 15 to 50 nucleotides in length and an antisense strand of 15 to 30 nucleotides in length, in which the sense strand forms a duplex region with the antisense strand, in which the sense strand comprises a sequence as set forth in any one of SEQ ID NO: 204, 211, 364, 365 and in which the antisense strand comprises a complementary sequence selected from SEQ ID NO: 286, 367, 369, 370. In some embodiments, the sense strand comprises a sequence as set forth in SEQ ID NO: 204, and the antisense strand comprises a sequences as set for in SEQ ID NO: 286. In some embodiments, the sense strand comprises a sequence as set forth in SEQ ID NO: 211, and the antisense strand comprises a sequences as set for in SEQ ID NO: 367. In some embodiments, the sense strand comprises a sequence as set forth in SEQ ID NO: 364, and the antisense strand comprises a sequences as set for in SEQ ID NO: 369. In some embodiments, the sense strand comprises a sequence as set forth in SEQ ID NO: 365, and the antisense strand comprises a sequences as set for in SEQ ID NO: 370. In some embodiments, the sense strand consists of a sequence as set forth in SEQ ID NO: 204, and the antisense strand consists of a sequences as set for in SEQ ID NO: 286. In some embodiments, the sense strand consists of a sequence as set forth in SEQ ID NO: 211, and the antisense strand consists of a sequences as set for in SEQ ID NO: 367. In some embodiments, the sense strand consists of a sequence as set forth in SEQ ID NO: 364, and the antisense strand consists of a sequences as set for in SEQ ID NO: 369. In some embodiments, the sense strand consists of a sequence as set forth in SEQ ID NO: 365, and the antisense strand consists of a sequences as set for in SEQ ID NO: 370.

Another aspect of the present disclosure provide an oligonucleotide for reducing expression of HMGB1, in which the oligonucleotide comprises a pair of sense and antisense strands selected from a row of Table 7. In some embodiments, an oligonucleotide provided herein comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all nucleotides in the oligonucleotide are modified. In some embodiments, the oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate. In some embodiments, at least one nucleotide of the oligonucleotide is conjugated to one or more targeting ligands. In some embodiments, each targeting ligand comprises a carbohydrate, amino sugar, cholesterol, polypeptide or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIGS. 3A-3D are a series of graphs showing the percent of HMGB1 mRNA remaining after a phase 1 screen of 96 HMGB1 oligonucleotides in Hepa1-6 cells. "Mm HMBG1 533-646" indicates the position of the 5' RT-PCR site and "Mm HMBG1 1541-1675" indicates the position of the 3' RT-PCR site on the mouse mRNA.

FIGS. 13A-13B are a set of graphs showing the percentage of HMGB1 mRNA (normalized to Hprt1 mRNA) remaining in mice after a 350 mg/kg APAP injection and treatment with GalNAc-conjugated HMGB1 oligonucleotides, LNP formulated HMGB1 oligonucleotides, or a PBS control. FIG. 13A shows liver HMGB1 expression and FIG. 16B shows serum HMGB1 expression. Saline-injected animals were used as controls. The HMGB1 oligonucleotide used in FIGS. 13A-13B is S212-AS296-M49.

FIGS. 14A-14C are a series of graphs showing AST, ALT, and serum miR122 expression post HMGB1 treatment in mice after a 350 mg/kg APAP injection and treatment with GalNAc-conjugated HMGB1 oligonucleotides, LNP formulated HMGB1 oligonucleotides, or a PBS control. Saline-injected animals were used as controls. The HMGB1 oligonucleotide used in FIGS. 14A-14C is S212-AS296-M49.

FIGS. 16A-16B are graphs showing the percentage of HMGB1 mRNA remaining in the liver or serum of mice after a 350 mg/kg APAP injection and treatment with GalNAc-conjugated HMGB1 oligonucleotides, LNP formulated HMGB1 oligonucleotides, or a PBS control. FIG. 16A shows liver HMGB1 expression and FIG. 16B shows serum HMGB1 expression. Saline-injected animals were used as controls. The HMGB1 oligonucleotide used in FIGS. 16A-16B is S212-AS296-M56.

FIGS. 30A-30D are graphs showing an in vivo activity evaluation of three GalNAc-conjugated HMGB1 oligonucleotides at 4-different time points. The data show the amount of HMGB1 mRNA remaining (normalized to the remaining HMGB1 mRNA levels in mice treated with PBS) on day 7, 14, 21, or 28 after administration of the oligonucleotides. FIGS. 30A and 30B show the results of 5' qPCR reactions. FIGS. 30C and 30D show the results of 3' qPCR reactions. The results showed that all tested GalNAc-conjugated HMGB1 oligonucleotides were potent in knocking down HMGB1 3 weeks after injection.

FIGS. 33A-33G are IC50 curves demonstrating uptake and activity of the 2 GalNAc-conjugates HMGB1 oligonucleotides in primary monkey hepatocytes. The IC50 curves were normalized to mock treatment. Results for RhHMGB1 5' qPCR reactions are shown in FIGS. 33A-33C), and results for 3' qPCR reactions are shown in FIGS. 33D-33F. A GalNAc-conjugate LDHA oligonucleotide was used as assay control (FIGS. 33C, 33F, and 33G). The level of remaining RhLDHA mRNA was measured by a LDHA specific primer in qPCR assay (FIG. 33G).

DETAILED DESCRIPTION OF THE INVENTION

Figure 1:
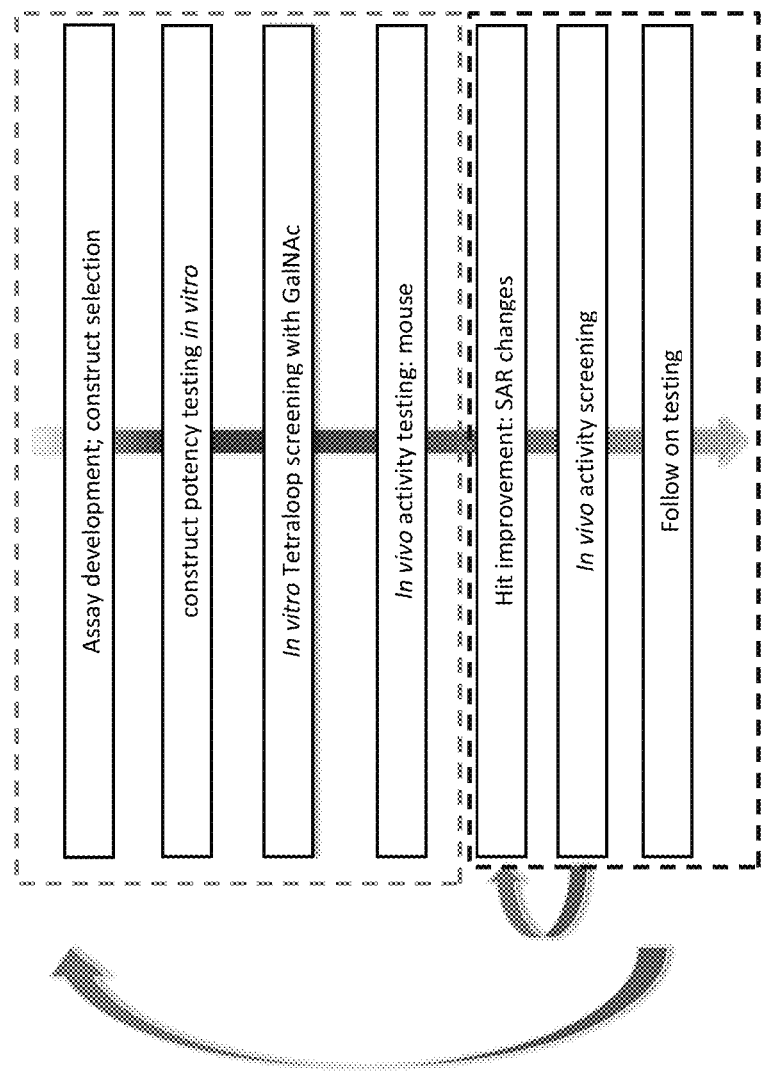
FIG. 1 is a flowchart depicting the experimental design used to select compounds for testing in cell and animal models and to develop double-stranded oligonucleotides for reducing expression of HMGB1. SAR: Structure-Activity Relationship.

According to some aspects, the disclosure provides oligonucleotides targeting HMGB1 mRNA that are effective for reducing HMGB1 expression in cells, particularly liver cells (e.g., hepatocytes) for the treatment of liver fibrosis. Accordingly, in related aspects, the disclosure provided methods of treating fibrosis that involve selectively reducing HMGB1 gene expression in liver. In certain embodiments, HMGB1 targeting oligonucleotides provided herein are designed for delivery to selected cells of target tissues (e.g., liver hepatocytes) to treat fibrosis in those tissues.

Further aspects of the disclosure, including a description of defined terms, are provided below.

I. Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administering: As used herein, the terms "administering" or "administration" means to provide a substance (e.g., an oligonucleotide) to a subject in a manner that is pharmacologically useful (e.g., to treat a condition in the subject).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells, and has a major role in binding, internalization, and subsequent clearance of circulating glycoproteins that contain terminal galactose or N-acetylgalactosamine residues (asialoglycoproteins).

Attenuates: As used herein, the term "attenuates" means reduces or effectively halts. As a non-limiting example, one or more of the treatments provided herein may reduce or effectively halt the onset or progression of liver fibrosis or liver inflammation in a subject. This attenuation may be exemplified by, for example, a decrease in one or more aspects (e.g., symptoms, tissue characteristics, and cellular, inflammatory or immunological activity, etc.) of liver fibrosis or liver inflammation, no detectable progression (worsening) of one or more aspects of liver fibrosis or liver inflammation, or no detectable aspects of liver fibrosis or liver inflammation in a subject when they might otherwise be expected.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other so as to form regions of complementarity, as described herein.

Deoxyribonucleotide: As used herein, the term "deoxyribonucleotide" refers to a nucleotide having a hydrogen in place of a hydroxyl at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, the complementary base-pairing of duplex region(s) of a double-stranded oligonucleotide is formed between of antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequence of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glu1), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Hepatotoxic agent: As used herein, a "hepatotoxic agent" is a chemical compound, virus, or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

Liver inflammation: As used herein, the term "liver inflammation" or "hepatitis" refers to a physical condition in which the liver becomes swollen, dysfunctional, and/or painful, especially as a result of injury or infection, as may be caused by exposure to a hepatotoxic agent. Symptoms may include jaundice (yellowing of the skin or eyes), fatigue, weakness, nausea, vomiting, appetite reduction, and weight loss. Liver inflammation, if left untreated, may progress to fibrosis, cirrhosis, liver failure, or liver cancer.

Liver fibrosis: As used herein, the term "liver fibrosis" or "fibrosis of the liver" refers to an excessive accumulation in the liver of extracellular matrix proteins, which could include collagens (I, III, and IV), fibronectin, undulin, elastin, laminin, hyaluronan, and proteoglycans resulting from inflammation and liver cell death. Liver fibrosis, if left untreated, may progress to cirrhosis, liver failure, or liver cancer.

Loop: As used herein the term, "loop" refers to a unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to a internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

Nicked Tetraloop Structure: A "nicked tetraloop structure" is a structure of a RNAi oligonucleotide characterized by the presense of separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

Oligonucleotide: As used herein, the term "oligonucleotide" refers to a short nucleic acid, e.g., of less than 100 nucleotides in length. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotides.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analogs contain a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, U.S. Provisional Application No. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to HMGB1 mRNA sequence) may result in a decrease in the amount of RNA transcript, protein and/or activity (e.g., encoded by the HMGB1 gene) compared to a cell that is not treated with the double-stranded oligonucleotide. Similarly, "reducing expression" as used herein refers to an act that results in reduced expression of a gene (e.g., HMGB1).

Region of Complementarity: As used herein, the term "region of complementary" refers to a sequence of nucleotides of a nucleic acid (e.g., a double-stranded oligonucleotide) that is sufficiently complementary to an antiparallel sequence of nucleotides to permit hybridization between the two sequences of nucleotides under appropriate hybridization conditions, e.g., in a phosphate buffer, in a cell, etc.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature (Tm) of an adjacent stem duplex that is higher than the Tm of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C. or at least 75° C. in 10 mM NaHPO$_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include but are not limited to non-Watson-Crick base pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors of HMGB1 Expression i. HMGB1 Hotspots

In some embodiments, oligonucleotide-based inhibitors of HMGB1 expression are provided herein that can be used to achieve a therapeutic benefit. Through examination of the HMGB1 mRNA, including mRNAs of multiple different species (human, rhesus monkey, and mouse (see, e.g., Example 1) and in vitro and in vivo testing, it has been discovered that certain regions of HMGB1 mRNA are hotspots for targeting because they are more amenable than others to oligonucleotide-based inhibition. In some embodiments, a hotspot region of HMGB1 comprises, or consists of, a sequence as forth in any one of SEQ ID NO:374-381. These regions of HMGB1 mRNA may be targeted using oligonucleotides as discussed herein for purposes of inhibiting HMGB1 mRNA expression.

Accordingly, in some embodiments, oligonucleotides provided herein are designed so as to have regions of complementarity to HMGB1 mRNA (e.g., within a hotspot of HMGB1 mRNA) for purposes of targeting the mRNA in cells and inhibiting its expression. The region of complementary is generally of a suitable length and base content to enable annealling of the oligonucleotide (or a strand thereof) to HMGB1 mRNA for purposes of inhibiting its expression. In some embodiments, the region of complementarity is at least 12, at least 13, at least 14, at least 15, at least 16, at least 17, at least 18, at least 19 or at least 20 nucleotides in length. In some embodiments, an oligonucleotide provided herein has a region of complementarity to HMGB1 that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to HMGB1 that is 12, 13, 14, 15, 16, 17, 18, 19, 20, 21, 22, 23, 24, 25, 26, 27, 28, 29 or 30 nucleotides in length.

In some embodiments, an oligonucleotide disclosed herein comprises a region of complementarity (e.g., on an antisense strand of a double-stranded oligonucleotide) that is at least partially complementary to a sequence as set forth in any one of SEQ ID NO: 1-96. In some embodiments, an oligonucleotide disclosed herein comprises a region of complementarity (e.g., on an antisense strand of a double-stranded oligonucleotide) that is fully complementary to a sequence as set forth in any one of SEQ ID NO: 1-96. In some embodiments, a region of complementarity of an oligonucleotide (e.g., on an antisense strand of a double-stranded oligonucleotide) is complementary to a contiguous sequence of nucleotides of a sequence as set forth in any one of SEQ ID NOs: 1-96, 193-272, and 363-365 that is in the range of 10 to 25 nucleotides (e.g., 10 to 25, 12 to 22, 15 to 25, 17 to 21, 18 to 25, 19-25, or 15 to 30 nucleotides) in length. In some embodiments, a region of complementarity of an oligonucleotide (e.g., on an antisense strand of a double-stranded oligonucleotide) is complementary to a contiguous sequence of nucleotides of a sequence as set forth in any one of SEQ ID NOs: 1-96, 193-272, and 363-365 that is 10, 11, 12, 13, 14, 15, 16, 17, 18, 19, 20, 21, 22, 23, 24, or 25 contiguous nucleotides in length.

In some embodiments, a region of complementarity of an oligonucleotide that is complementary to contiguous nucleotides of a sequence as set forth in any one of SEQ ID NOs: 1-96, 193-272, and 363-365 spans the entire length of an antisense strand. In some embodiments, a region of complementarity of an oligonucleotide that is complementary to contiguous nucleotides of a sequence as set forth in any one of SEQ ID NOs:1-96, 193-272, and 363-365 spans a portion of the entire length of an antisense strand. In some embodiments, an oligonucleotide disclosed herein comprises a region of complementarity (e.g., on an antisense strand of a double-stranded oligonucleotide) that is at least partially (e.g., fully) complementary to a contiguous stretch of nucleotides spanning nucleotides 1-19 of a sequence as set forth in any one of SEQ ID NOs: 193-272, 193-272, and 363-365.

In some embodiments, a region of complementarity to HMGB1 may have one or more mismatches compared with a corresponding sequence of HMGB1 mRNA. A region of complementarity on an oligonucleotide may have up to 1, up to 2, up to 3, up to 4, up to 5, etc. mismatches provided that it maintains the ability to form complementary base pairs with HMGB1 mRNA under appropriate hybridization conditions. Alternatively, a region of complementarity on an oligonucleotide may have no more than 1, no more than 2, no more than 3, no more than 4, or no more than 5 mismatches provided that it maintains the ability to form complementary base pairs with HMGB1 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with HMGB1 mRNA under appropriate hybridization conditions.

ii. Types of Oligonucleotides

There are a variety of structures of oligonucleotides that are useful for targeting HMGB1 in the methods of the present disclosure, including RNAi, antisense, miRNA, etc. Any of the structures described herein or elsewhere may be used as a framework to incorporate or target a sequence described herein (e.g., a hotpot sequence of HMBG1 such as those illustrated in SEQ ID NOs: 374-381).

In some embodiments, oligonucleotides for reducing the expression of HMGB1 expression engage RNA interference (RNAi) pathways upstream or downstream of dicer involvement. For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, oligonucleotides provided herein are designed to engage in the RNA interference pathway downstream of the involvement of dicer (e.g., dicer cleavage). Such oligonucleotides may have an overhang (e.g., of 1, 2, or 3 nucleotides in length) in the 3' end of the sense strand. Such oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. Longer oligonucleotide designs are also available including oligonucleotides having a guide strand of 23 nucleotides and a passenger strand of 21 nucleotides, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region. See, for example, U.S. Pat. Nos. 9,012,138, 9,012,621, and 9,193,753, each of which are incorporated herein for their relevant disclosures.

In some embodiments, oligonucleotides as disclosed herein may comprise sense and antisense strands that are both in the range of 17 to 26 (e.g., 17 to 26, 20 to 25, or 21-23) nucleotides in length. In some embodiments, an oligonucleotide as disclosed herein comprises a sense and antisense strand that are both in the range of 19-21 nucleotide in length. In some embodiments, the sense and antisense strands are of equal length. In some embodiments, an oligonucleotide comprises sense and antisense strands, such that there is a 3'-overhang on either the sense strand or the antisense strand, or both the sense and antisense strand. In some embodiments, for oligonucleotides that have sense and antisense strands that are both in the range of 21-23 nucleotides in length, a 3' overhang on the sense, antisense, or both sense and antisense strands is 1 or 2 nucleotides in length. In some embodiments, the oligonucleotide has a guide strand of 23 nucleotides and a passenger strand of 21 nucleotides, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of HMGB1 are microRNA (miRNA), short hairpin RNA (shRNA), and short siRNA (see, e.g., Hamilton et al., Embo J., 2002, 21(17): 4671-4679; see also U.S. Application No. 20090099115).

Still, in some embodiments, an oligonucleotide for reducing HMGB1 expression as described herein is single-stranded. Such structures may include, but are not limited to single-stranded RNAi molecules. Recent efforts have demonstrated the activity of single-stranded RNAi molecules (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iii. Double-Stranded Oligonucleotides

Double-stranded oligonucleotides for targeting HMGB1 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked. In some embodiments, a duplex formed between a sense and antisense strand is at least 15 (e.g., at least 15, at least 16, at least 17, at least 18, at least 19, at least 20, or at least 21) nucleotides in length. In some embodiments, a duplex formed between a sense and antisense strand is in the range of 15-30 nucleotides in length (e.g., 15 to 30, 15 to 27, 15 to 22, 18 to 22, 18 to 25, 18 to 27, 18 to 30, or 21 to 30 nucleotides in length). In some embodiments, a duplex formed between a sense and antisense strand is 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

In some embodiments, an oligonucleotide provided herein comprises a sense strand having a sequence as set forth in any one of SEQ ID NO: 1-96 and an antisense strand comprising a complementary sequence selected from SEQ ID NO: 97-192, as is arranged Table 7 (e.g., a sense strand comprising a sequence as set forth in SEQ ID NO: 1 and an antisense strand comprising a sequence as set forth in SEQ ID NO: 97). In some embodiments, an oligonucleotide provided herein comprises a sense strand comprising a sequence as set forth in any one of SEQ ID NO: 193-272 and 363-365 and an antisense strand comprising a complementary sequence selected from SEQ ID NO: 273-362 and 366-370, as is also arranged Table 7 (e.g., a sense strand comprising a sequence as set forth in SEQ ID NO: 193 and an antisense strand comprising a sequence as set forth in SEQ ID NO: 273). It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

In some embodiments, a double-stranded oligonucleotide comprises a 25 nucleotide sense strand and a 27 nucleotide antisense strand that when acted upon by a dicer enzyme results in an antisense strand that is incorporated into the mature RISC. In some embodiments, a sense strand of an oligonucleotide is longer than 27 nucleotides (e.g., 28, 29, 30, 31, 32, 33, 34, 35, 36, 37, 38, 39 or 40 nucleotides). In some embodiments, a sense strand of an oligonucleotide is longer than 25 nucleotides (e.g., 26, 27, 28, 29 or 30 nucleotides). The length of a duplex formed between a sense and antisense strand of an oligonucleotide may be 12 to 30 nucleotides (e.g., 12 to 30, 12 to 27, 15 to 25, 18 to 30 or 19 to 30 nucleotides) in length. In some embodiments, the length of a duplex formed between a sense and antisense strand of an oligonucleotide is at least 12 nucleotides long (e.g., at least 12, at least 15, at least 20, or at least 25 nucleotides long). In some embodiments, the length of a duplex formed between a sense and antisense strand of an oligonucleotide is 12, 13, 14, 15, 16, 17, 18, 19, 20, 21, 22, 23, 24, 25, 26, 27, 28, 29, or 30 nucleotides in length.

In some embodiments, oligonucleotides provided herein have one 5' end that is thermodynamically less stable compared to the other 5' end. In some embodiments, an asymmetry oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7 or 8 nucleotides in length). Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, two terminal nucleotides on the 3' end of an antisense strand are modified. In some embodiments, the two terminal nucleotides on the 3' end of the antisense strand are complementary with the target. In some embodiments, the two terminal nucleotides on the 3' end of the antisense strand are not complementary with the target. In some embodiments, two terminal nucleotides on each 3' end of an oligonucleotide in the nicked tetraloop structure are GG. Typically, one or both of the two terminal GG nucleotides on each 3' end of an oligonucleotide is not complementary with the target.

In some embodiments, there is one or more (e.g., 1, 2, 3, 4, 5) mismatch between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

a. Antisense Strands

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments a sense strand complementary with a guide strand may be referred to as a "passenger strand."

In some embodiments, an oligonucleotide provided herein comprises an antisense strand that is up to 50 nucleotides in length (e.g., up to 30, up to 27, up to 25, up to 21, or up to 19 nucleotides in length). In some embodiments, an oligonucleotide provided herein comprises an antisense strand is at least 12 nucleotides in length (e.g., at least 12, at least 15, at least 19, at least 21, at least 25, or at least 27 nucleotides in length). In some embodiments, an antisense strand of an oligonucleotide disclosed herein is in the range of 12 to 50 or 12 to 30 (e.g., 12 to 30, 11 to 27, 11 to 25, 15 to 21, 15 to 27, 17 to 21, 17 to 25, 19 to 27, or 19 to 30) nucleotides in length. In some embodiments, an antisense strand of any one of the oligonucleotides disclosed herein is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments an oligonucleotide disclosed herein comprises an antisense strand comprising a sequence as set forth in any one of SEQ ID NO: 97-192, 273-362, or 366-370. In some embodiments, an oligonucleotide comprises an antisense strand comprising at least 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NO: 97-192, 273-362, or 366-370. In some embodiments, an oligonucleotide comprises an antisense strand comprising a contiguous sequence of nucleotides that is in the range of 12 to 30 nucleotides (e.g., 12 to 27, 12 to 22, 15 to 25, 17 to 21, 18 to 27, 19 to 27, or 15 to 27 nucleotides) in length of any of the sequences as set forth in any one of SEQ ID NO: 97-192, 273-362, or 366-370. In some embodiments, an oligonucleotide comprises an antisense strand comprising a contiguous sequence of nucleotides of a sequence as set forth in any one of SEQ ID NO: 97-192, 273-362, or 366-370 that is 12, 13, 14, 15, 16, 17, 18, 19, 20, 21, 22, 23, 24, 25, 26, or 27 contiguous nucleotides in length. In some embodiments, an oligonucleotide comprises an antisense strand that consists of a sequence as set forth in any one of SEQ ID NO: 97-192, 273-362, or 366-370.

b. Sense Strands

In some embodiments, a double-stranded oligonucleotide may have a sense strand of up to 40 nucleotides in length (e.g., up to 40, up to 35, up to 30, up to 27, up to 25, up to 21, up to 19 up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 35, or at least 38 nucleotides in length). In some embodiments, an oligonucleotide may have a sense strand in a range of 12 to 50 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, a sense strand of an oligonucleotide is longer than 27 nucleotides (e.g., 28, 29, 30, 31, 32, 33, 34, 35, 36, 37, 38, 39 or 40 nucleotides). In some embodiments, a sense strand of an oligonucleotide is longer than 25 nucleotides (e.g., 26, 27, 28, 29 or 30 nucleotides).

In some embodiments, an oligonucleotide disclosed herein comprises a sense strand sequence as set forth in in any one of SEQ ID NO: 1-96, 193-272, or 363-365. In some embodiments, an oligonucleotide has a sense strand that comprises at least 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NO: 1-96, 193-272, or 363-365. In some embodiments, an oligonucleotide has a sense strand that comprises a contiguous sequence of nucleotides that is in the range of 7 to 36 nucleotides (e.g., 12 to 30, 12 to 27, 12 to 22, 15 to 25, 17 to 21, 18 to 27, 19-27, 20-36, or 15 to 36 nucleotides) in length of any of the sequences as set forth in any one of SEQ ID NO: 1-96, 193-272, or 363-365. In some embodiments, an oligonucleotide has a sense strand that comprises a contiguous sequence of nucleotides of a sequence as set forth in any one of SEQ ID NO: 1-96, 193-272, or 363-365 that is 12, 13, 14, 15, 16, 17, 18, 19, 20, 21, 22, 23, 24, 25, 26, 27, 28, 29, 30, 31, 32, 33, 34, 35, or 36 nucleotides in length. In some embodiments, an oligonucleotide has a sense strand that consists of a sequence as set forth in any one of SEQ ID NO: 1-96, 193-272, or 363-365.

In some embodiments, a sense strand comprises a stem-loop at its 3'-end. In some embodiments, a sense strand comprises a stem-loop at its 5'-end. In some embodiments, a strand comprising a stem loop is in the range of 2 to 66 nucleotides long (e.g., 2 to 66, 10 to 52, 14 to 40, 2 to 30, 4 to 26, 8 to 22, 12 to 18, 10 to 22, 14 to 26, or 14 to 30 nucleotides long). In some embodiments, a strand comprising a stem loop is 8, 9, 10, 11, 12, 13, 14, 15, 16, 17, 18, 19, 20, 21, 22, 23, 24, 25, 26, 27, 28, 29, or 30 nucleotides in length. In some embodiments, a stem comprises a duplex of 1, 2, 3, 4, 5, 6, 7, 8, 9, 10, 11, 12, 13, or 14 nucleotides in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 1, 2, 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides. However, in some embodiments, a tetraloop comprises or consists of 3 to 6 nucleotides, and typically consists of 4 to 5 nucleotides. In certain embodiments, a tetraloop comprises or consists of three, four, five, or six nucleotides.

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides maybe be delivered in vivo by conjugating them to or encompassing them in a lipid nanoparticle (LNP) or similar carrier. However, when an oligonucleotide is not protected by an LNP or similar carrier, it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every sugar is modified at the 2'-position. These modifications may be reversible or irreversible. In some embodiments, an oligonucleotide as disclosed herein has a number and type of modified nucleotides and sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred herein to a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. A 2'-modification may be 2'-aminoethyl, 2'-fluoro, 2'-O-methyl, 2'-O-methoxyethyl, and 2'-deoxy-2'-fluoro-β-d-arabinonucleic acid. Typically, the modification is 2'-fluoro, 2'-O-methyl, or 2'-O-methoxyethyl. In some embodiments a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) with a phosphate group or other group, which can be used, for example, to attach linkers, adapters or labels or for the direct ligation of an oligonucleotide to another nucleic acid.

b. 5' Terminal Phophates

In some embodiments, 5'-terminal phosphate groups of oligonucleotides enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, U.S. Provisional Application No. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprise a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—$CH_2$—PO(OH)$_2$ or —O—CH2-PO(OR)$_2$, in which R is independently selected from H, $CH_3$, an alkyl group, $CH_2CH_2CN$, $CH_2OCOC(CH_3)_3$, $CH_2OCH_2CH_2Si(CH_3)_3$, or a protecting group. In certain embodiments, the alkyl group is $CH_2CH_3$. More typically, R is independently selected from H, $CH_3$, or $CH_2CH_3$.

c. Modified Intranucleoside Linkages

In some embodiments, phosphate modifications or substitutions may result in an oligonucleotide comprises at least one (e.g., at least 1, at least 2, at least 3 or at least 5) comprising a modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base Modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments a universal base is a heterocyclic moiety located at the 1' position of a nucleotide sugar moiety in a modified nucleotide, or the equivalent position in a nucleotide sugar moiety substitution, that, when present in a duplex, can be positioned opposite more than one type of base without substantially altering structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower Tm than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., Nature Biotechnology, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. *J. Am. Chem. Soc.* 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2' carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of sugar, particularly when the modified nucleotide is the 3'-terminal nucleotide of the oligonucleotide. In some embodiments, the glutathione-sensitive moiety comprises a sulfonyl group. See, e.g., U.S. Prov. Appl. No. 62/378,635, entitled Compositions Comprising Reversibly Modified Oligonucleotides and Uses Thereof, which was filed on Aug. 23, 2016, and the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligand.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferring, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligand are conjugated to a 2 to 4 nucleotide overhang or extension on the 5' or 3' end of the sense or antisense strand) such that the targeting ligands resemble bristles of a toothbrush and the oligonucleotide resembles a toothbrush. For example an oligonucleotide may comprise a stem-loop at either the 5' or 3' end of the sense strand and 1, 2, 3 or 4 nucleotides of the loop of the stem may be individually conjugated to a targeting ligand.

In some embodiments, it is desirable to target an oligonucleotide that reduces the expression of HMGB1 to the hepatocytes of the liver of the subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to a one or more bivalent GalNAc, trivalent GalNAc, or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligand are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example an oligonucleotide may comprise a stem-loop at either the 5' or 3' end of the sense strand and 1, 2, 3 or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand where each GalNAc moiety is conjugated to one nucleotide.

Any appropriate method or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable.

In some embodiments, a duplex extension (e.g., of up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of HMGB1. Such compositions can be suitably formulated such that when administered to a subject, either into the immediate environment of a target cell or systemically, a sufficient portion of the oligonucleotides enter the cell to reduce HMGB1 expression. Any of a variety of suitable oligonucleotide formulations can be used to deliver oligonucleotides for the reduction of HMGB1 as disclosed herein. In some embodiments, an oligonucleotide is formulated in buffer solutions such as phosphate buffered saline solutions, liposomes, micellar structures, and capsids.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine, can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing HMGB1 expression) or more, although the percentage of the active ingredient(s) may be between about 1% 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing HMGB1 Expression in Cells

In some embodiments, methods are provided for delivering to a cell an effective amount any one of oligonucleotides disclosed herein for purposes of reducing expression of HMGB1 in the cell. Methods provided herein are useful in any appropriate cell type. In some embodiments, a cell is any cell that expresses HMGB1 (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell that has been obtained from a subject and that may have undergone a limited number of a passages, such that the cell substantially maintains is natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of oligonucleotides disclosed herein for purposes of reducing expression of HMGB1 solely in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of HMGB1 expression (e.g., RNA, protein). In some embodiments, the extent to which an oligonucleotide provided herein reduces levels of expression of HMGB1 is evaluated by comparing expression levels (e.g., mRNA or protein levels of HMGB1 to an appropriate control (e.g., a level of HMGB1 expression in a cell or population of cells to which an oligonucleotide has not been delivered or to which a negative control has been delivered). In some embodiments, an appropriate control level of HMGB1 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of HMGB1 expression in a cell. In some embodiments, the reduction in levels of HMGB1 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of HMGB1. The appropriate control level may be a level of HMGB1 expression in a cell or population of cells that has not been contacted with an oligonucleotide as described herein. In some embodiments, the effect of delivery of an oligonucleotide to a cell according to a method disclosed herein is assessed after a finite period of time. For example, levels of HMGB1 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing HMGB1 expression in for attenuating the onset or progression of liver fibrosis in a subject. In some embodiments, the methods may comprise administering to a subject in need thereof an effective amount of any one of the oligonucleotides disclosed herein. Such treatments could be used, for example, to slow or halt any type of liver fibrosis. The present disclosure provides for both prophylactic and therapeutic methods of treating a subject at risk of (or susceptible to) a disease or disorder associated with liver fibrosis and/or liver inflammation.

In certain aspects, the disclosure provides a method for preventing in a subject, a disease or disorder as described herein by administering to the subject a therapeutic agent (e.g., an oligonucleotide or vector or transgene encoding same). In some embodiments, the subject to be treated is a subject who will benefit therapeutically from a reduction in the amount of HMGB1 protein, e.g., in the liver. Subjects at risk for the disease or disorder can be identified by, for example, one or a combination of diagnostic or prognostic assays known in the art (e.g., identification of liver fibrosis and/or liver inflammation). Administration of a prophylactic agent can occur prior to the detection of or the manifestation of symptoms characteristic of the disease or disorder, such that the disease or disorder is prevented or, alternatively, delayed in its progression.

Methods described herein are typically involve administering to a subject in an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

As a non-limiting set of examples, the oligonucleotides of the instant disclosure would typically be administered quarterly (once every three months), bi-monthly (once every two months), monthly, or weekly. For example, the oligonucleotides may be administered every one, two, or three weeks. The oligonucleotides may be administered daily.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Example 1: Development of HMGB1 RNAi Oligonucleotides Using Human and Mouse Cell-Based Assays FIG. 1 shows a workflow using human and mouse-based assays to develop candidate RNAi oligonucleotides for inhibition of HMGB1 expression. First, a computer-based algorithm was used to generate candidate oligonucleotide sequences (25-27-mer) for HMGB1 inhibition. Cell-based assays and PCR assays were then employed for evaluation of candidate RNAi oligonucleotides for their ability to reduce HMBG1 expression.

The computer algorithm provided RNAi oligonucleotide sequences that were complementary to the human HMGB1 mRNA (SEQ ID NO: 371, Table 1), of which certain sequences were also complementary to the monkey HMGB1 mRNA (SEQ ID NO: 372, Table 1), and the mouse HMGB1 mRNA (SEQ ID NO: 373, Table 1).

TABLE 1

Sequences of human, rhesus monkey and mouse HMGB1 mRNA

| Species | GenBank RefSeq # | Sequence Identifier |
| --- | --- | --- |
| Human | NM_002128.5 | SEQ ID NO: 371 |
| Monkey | NM_001283356.1 | SEQ ID NO: 372 |
| Mouse | NM_010439.4 | SEQ ID NO: 373 |

The algorithm produced hundreds of RNAi oligonucleotide sequences of which 96 oligonucleotides were identified bioinformatically as top candidates for experimental evaluation in a cell-based assay. In this assay, Hepa 1-6 (ATCC® CRL-1830™) hepatocyte cells expressing HMGB1 were transfected with the oligonucleotides. Cells were maintained for a period of time following transfection and then levels of remaining HMGB1 mRNA were interrogated using TAQMAN®-based qPCR assays. Two qPCR assays, a 3' assay and a 5' assay were used. All 96 RNAi oligonucleotides were evaluating using the same modification pattern, designated M15, which contains a combination of ribonucleotides, deoxyribonucleotides and 2'-O-methyl modified nucleotides. The sequences of the oligonucleotides tested are provided in Table 2.

TABLE 2

| Candidate oligonucleotide Sequences for Mouse Hepa 1-6 Cell-Based Assay | | | | |
| --- | --- | --- | --- | --- |
| Hs | Rh | Mm | Sense SEQ ID NO | Corresponding Antisense SEQ ID NO |
| X | X | X | 1-11; 24-43; 54-69; 96 | 97-107; 120-139; 150-165; 192 |
| X | X |   | 12-23; 53; 70; 71; 73-75; 89-93; 95 | 108-119; 149; 166; 167; 169-171; 185-189; 191 |
| X |   |   | 44-52 | 140-148 |

Hs: human, Rh: rhesus monkey, and Mm: mouse; the sense and antisense SEQ ID NO columns provide the sense strand and respective antisense strand that are hybridized to make each oligonucleotide. For example, sense strand with SEQ ID NO: 1 hybridizes with antisense strand with SEQ ID NO: 97; each of the oligonucleotides tested had the same modification pattern.

Hot Spots in HMGB1 mRNA

Data from the screen of the 96 candidate RNAi oligonucleotides is shown in FIGS. 3A-3D. Top performing oligonucleotides in the cell based assay that resulted in less than or equal to 25% mRNA remaining compared to negative controls were selected as hits for further experimental characterization. Oligonucleotides that were not found to inhibit HMGB1 expression were used as negative controls. House-keeping gene Hypoxanthine-guanine phosphoribosyltransferase (HPRT) was used as a normalizing gene for HMGB1 expression, as its expression is not altered by inhibiting the expression of HMGB1.

Hotspots in human HMGB1 mRNA were identified by examining the activity and locations of these oligonucleotides. A hotspot was identified as a stretch on the human HMGB1 mRNA sequence associated with at least two oligonucleotides resulting in mRNA levels that were less than or equal to 25% in either assay compared with controls.

Accordingly, the following hotspots within the human HMGB1 mRNA sequence were identified: 935-965; 1100-1130; 1160-1215; 1230-1270; 1470-1500; 1680-1710; 2190-2220; and 2280-2310.

The sequences of the hotspots are outlined in Table 3.

TABLE 3

Sequences of Hotspots

| Hotspot Position | Sequence | SEQ ID NO: |
|---|---|---|
| 935-965 | TAAGATTTGTTTTTAAACTGTACAGTGTCTT | 374 |
| 1100-1130 | TTGGTGCACAGCACAAATTAGTTATATATGG | 375 |
| 1160-1215 | TCTGATGCAGCTTATACGAAATAATTGTTGT TCTGTTAACTGAATACCACTCTGTA | 376 |
| 1230-1270 | AAAAAAGTTGCAGCTGTTTTGTTGACATTCT GAATGCTTCT | 377 |
| 1470-1500 | TGAGATAGTTTTCATCCATAACTGAACATCC | 378 |
| 1680-1710 | TACCATGTAATGGCAGTTATATTTTGCAGTT | 379 |
| 2190-2220 | TTTACACGCTTTTGTGATGGAGTGCTGTTTT | 380 |
| 2280-2310 | AATACTGAACATCTGAGTCCTGGATGATACT | 381 |

Dose Response Analysis

Figure 4:
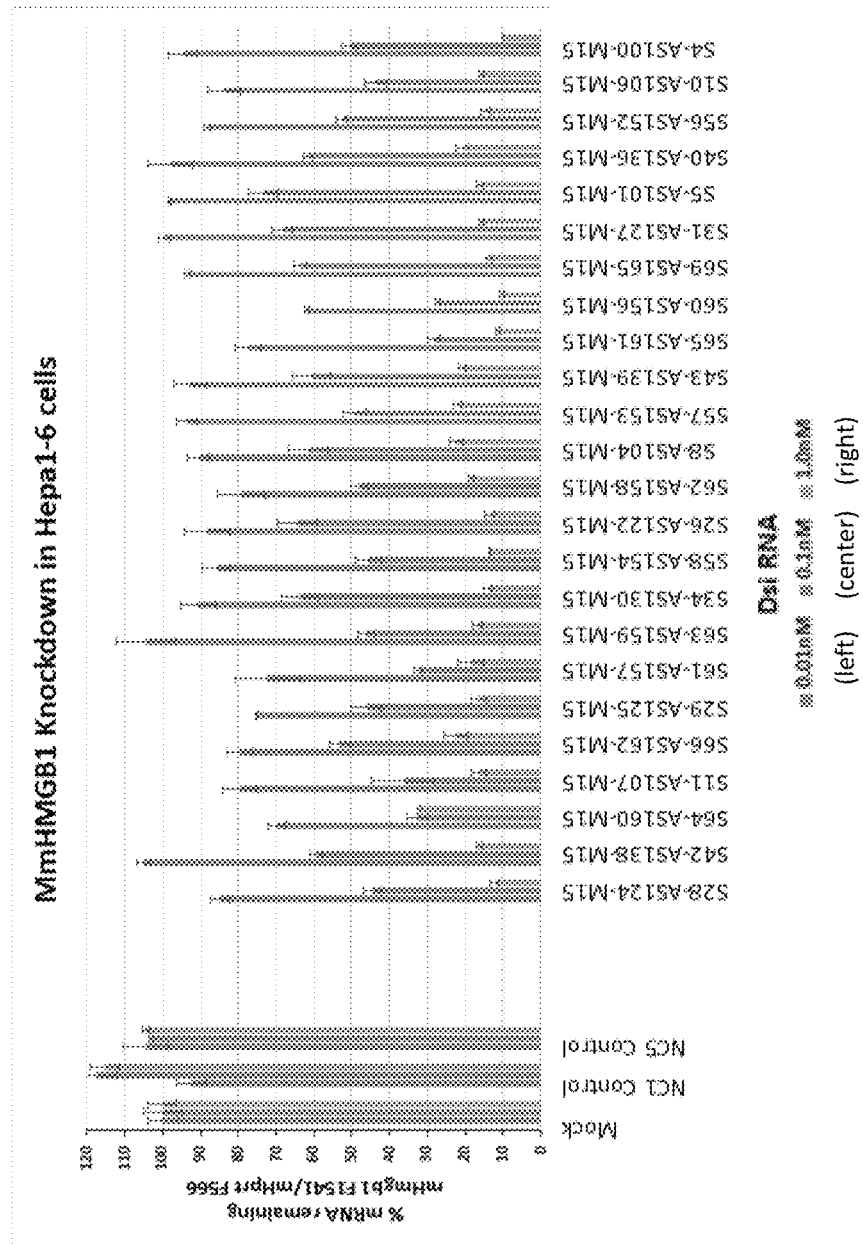
FIG. 4 is a graph showing the percentage of mRNA remaining after HMGB1 oligonucleotide phase 2 screening of 96 HMGB1 oligonucleotides at three different concentrations (1 nM, 0.1 nM and 0.01 nM) in Hepa1-6 cells (3' assay).

Twenty-four top performing RNAi oligonucleotides were selected for analysis in a secondary screen, taking into account gene location and sequence conservation between species. In this secondary screen, the RNAi oligonucleotides were tested using the same assay as in the primary screen, but at three different concentrations (1 nM, 0.1 nM and 0.01 nM) (FIG. 4). Those RNAi oligonucleotides showing activity at two more concentrations were then subjected to further analysis.

Figure 5:
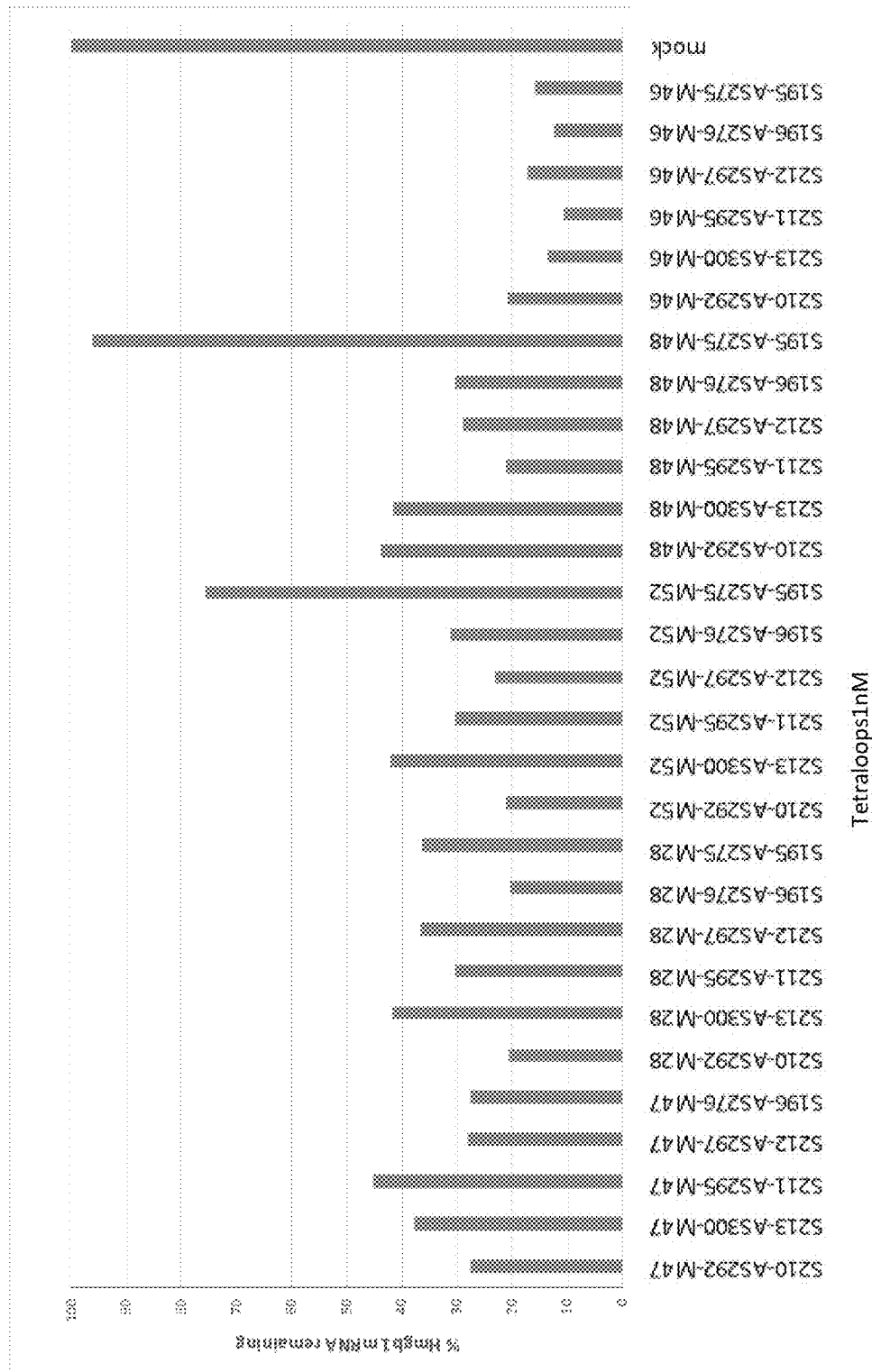
FIG. 5 is a graph showing the results of screening in Hepa1-6 cells using HMGB1 oligonucleotides of different base sequences in the nicked tetraloop structure, adapted to different modification patterns and an unmodified control.
Figure 6:
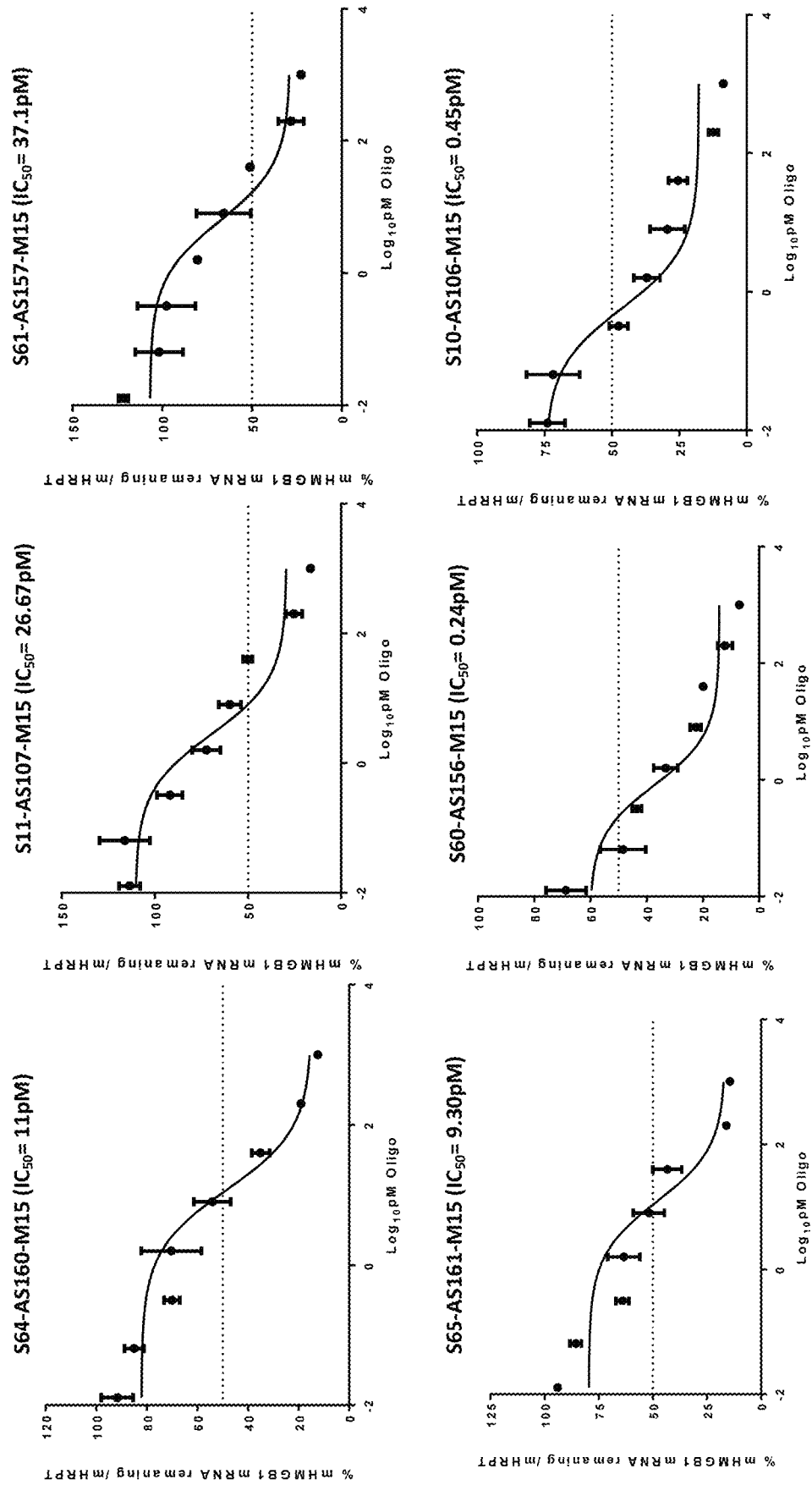
FIG. 6 is a graph showing the $IC_{50}$ results for six HMGB1 oligonucleotides selected from dose response curve screening in Hepa1-6 cells.

In this further analysis of the top candidates from the secondary screen, the sequences were incorporated into RNAi oligonucleotides in a nicked tetraloop structure format (a 36-mer passenger strand with a 22-mer guide strand). These RNAi oligonucleotides in the nicked tetraloop structure format were initially tested at 1 nM for their ability to reduce HMGB1 mRNA expression. FIG. 5 shows data for RNAi oligonucleotides made from different base sequences with nicked tetraloop structures, each adapted to four different modification patterns, designated M28, M47, M48, and M52, which comprise in their sense and antisense strands 2'-fluoro and 2'-O-methyl modified nucleotides in different arrangements and phosphorothioate and phosphodiester linkages, and include in their antisense strands a phosphate analog positioned at the 5' terminal nucleotide, and an unmodified control, designated M46. The top RNAi oligonucleotides were further tested using a full dose response curve in Hepa1-6 cells in order to determine the half maximal inhibitory concentration ($IC_{50}$) for each compound (see FIG. 6).

In Vivo Murine Experimentation

Figure 2:
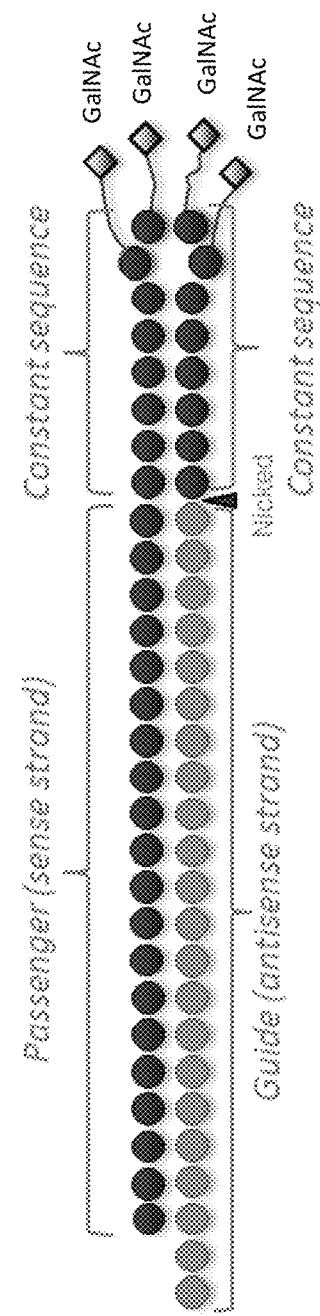
FIG. 2 is a schematic showing a non-limiting example of a double-stranded oligonucleotide with a nicked tetraloop structure that has been conjugated to four GalNAc moieties (diamonds on the right side of the molecule).
Figure 3A:
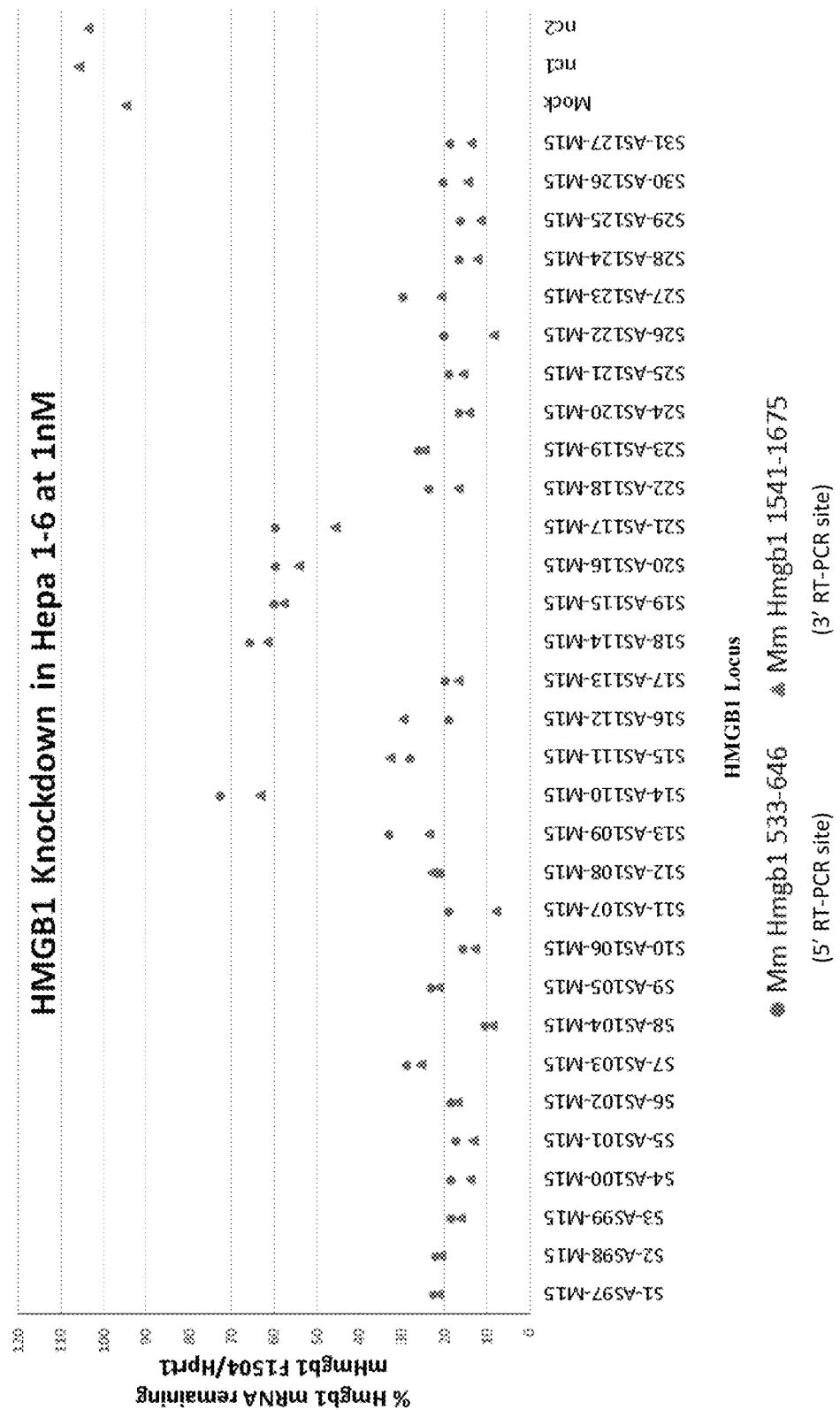
Figure 3B:
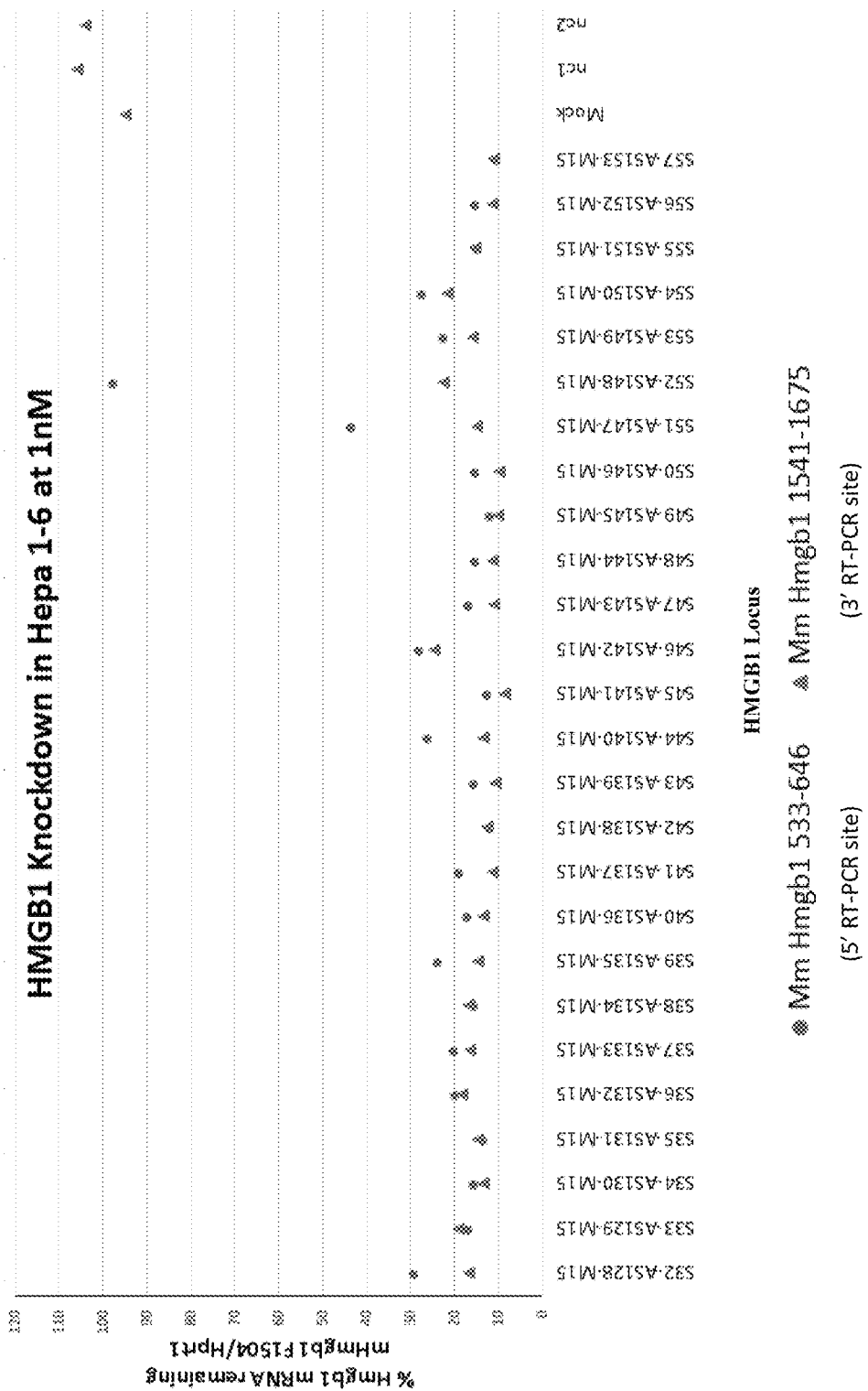
Figure 3D:
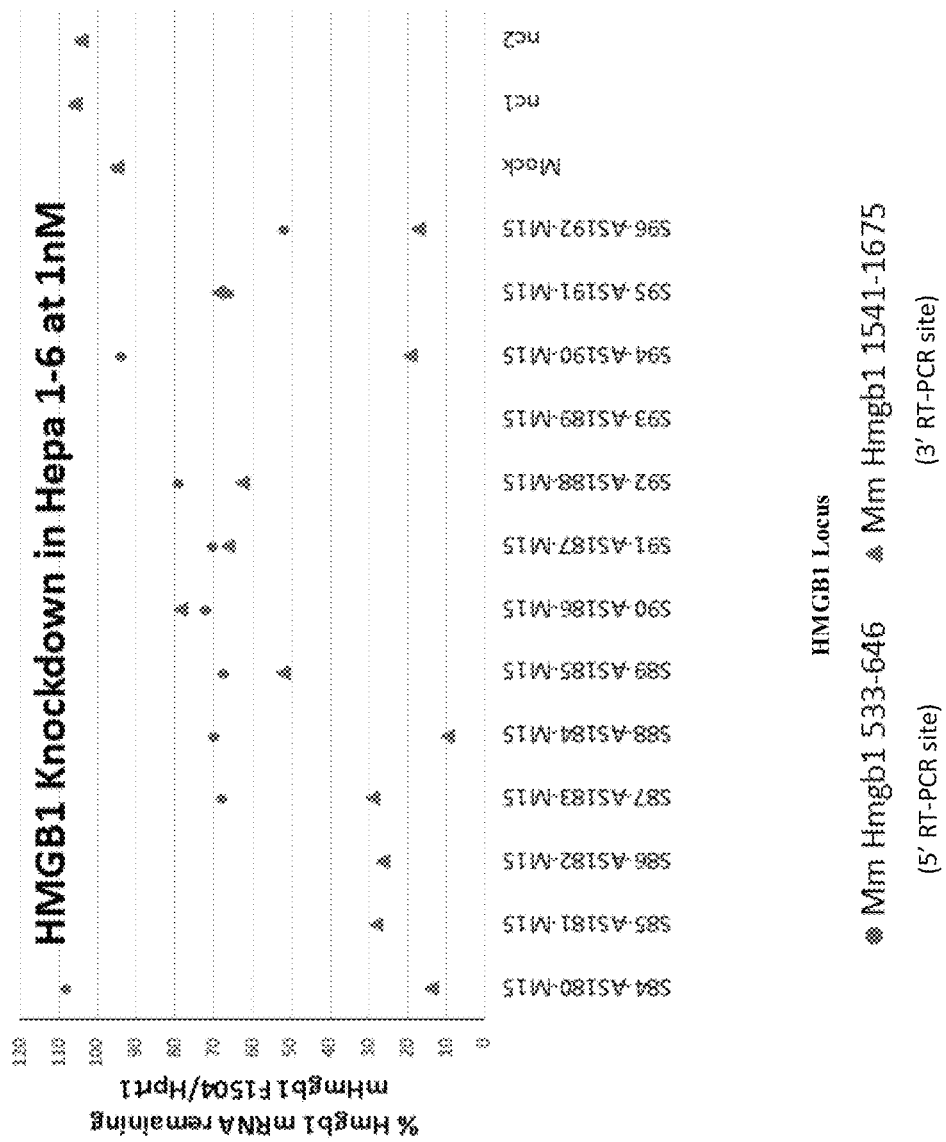

Data from the above in vitro experiments were assessed to identify tetraloops and modification patterns that would improve delivery properties while maintaining activity for reduction of HMGB1 expression in the mouse hepatocytes. Based on this analysis, select oligonucleotides were then conjugated to GalNAc moieties. Monovalent GalNAc moieties were conjugated to each nucleotide of the GAAA sequence in the tetraloop of the sense strand, as illustrated in FIG. 2. Conjugation was performed using a click linker. The GalNAc used was as shown below:

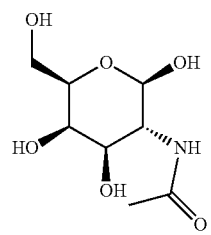

N-Acetyl-b-D-galactosamine (CAS#: 14131-60-3)

Figure 7:
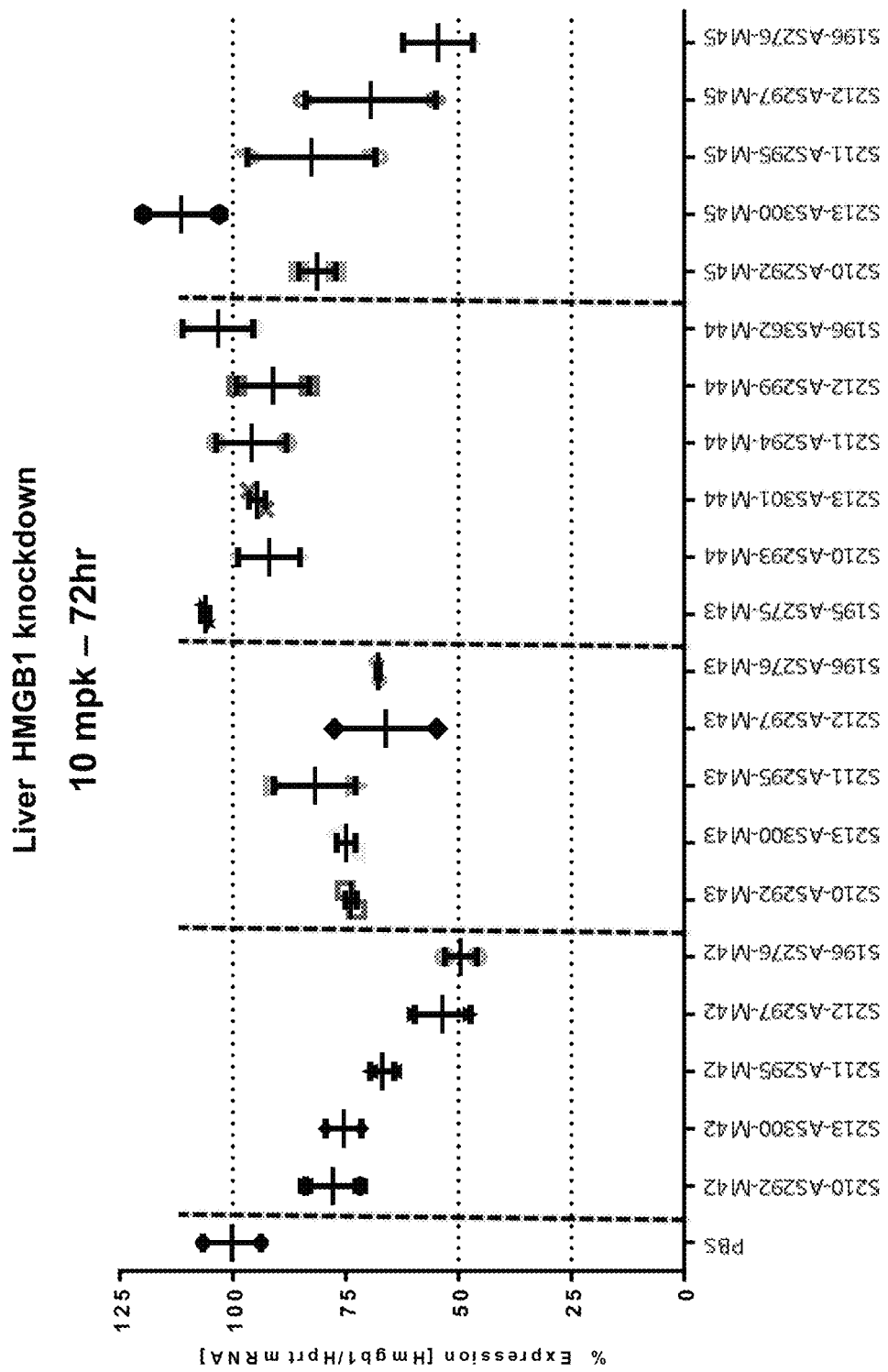
FIG. 7 is a graph showing the amount of HMGB1 mRNA relative to the amount HPRT mRNA remaining in the liver 72 hours after subcutaneous administration of 10 mg/kg (mpk) GalNAc-conjugated HMGB1 oligonucleotide in C57BL/6.

Groups of GalNAc-conjugated RNAi oligonucleotides with different modification patterns and nicked tetraloop structures were subcutaneously administered to C57BL/6 mice at 10 mg/kg. The percentage of HMGB1 mRNA as compared to HPRT control mRNA was measured at 72 hours (FIG. 7).

Figure 8:
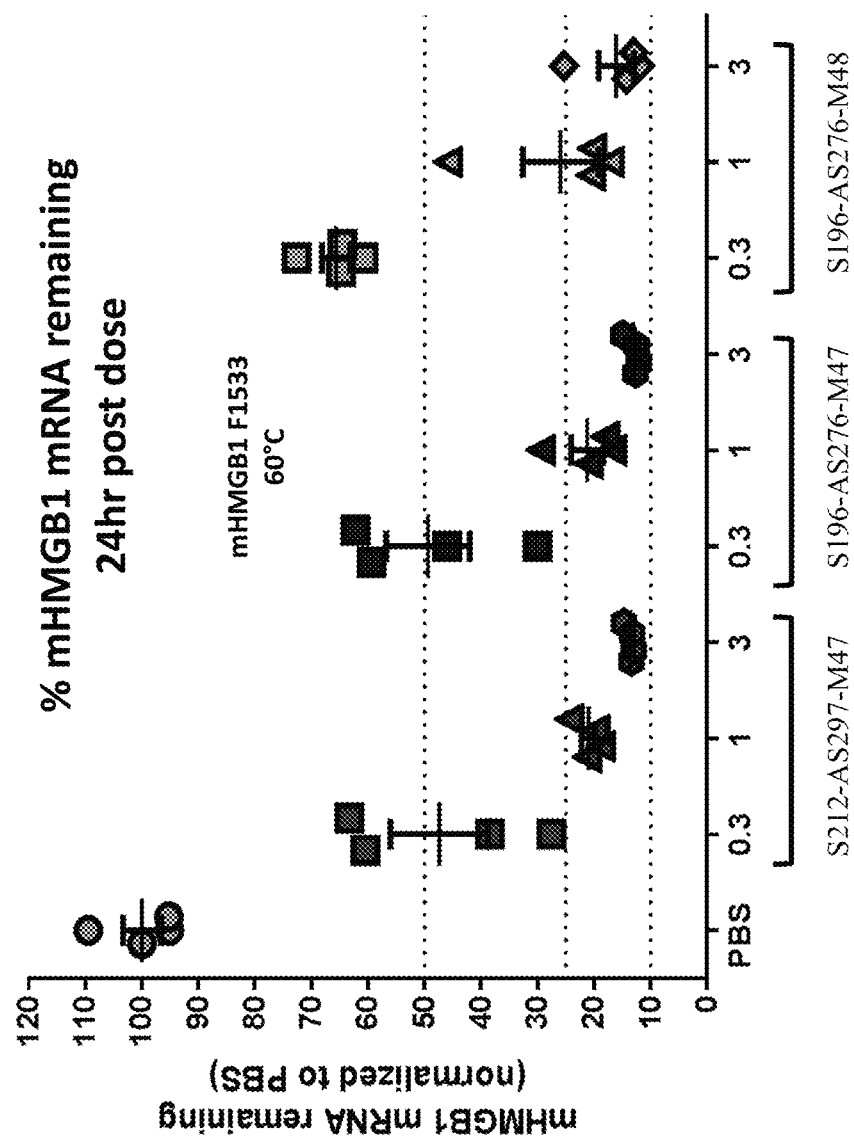
FIG. 8 is a graph showing an in vivo activity evaluation of three HMGB1 oligonucleotides in a nicked tetraloop structure. LNP formulated oligonucleotides were administered intravenously to mice at three different dosages (0.3 mg/kg, 1 mg/kg and 3 mg/kg). The data show the amount of HMGB1 mRNA remaining at 24 hours after administration normalized to a PBS control treatment.

Three candidate GalNAc-conjugated oligonucleotides containing nicked tetraloop structures were tested again at three different doses (0.3 mg/kg, 1 mg/kg, and 3 mg/kg) for the amount of HMGB1 mRNA remaining at 24 hours after oligonucleotide administration compared to a PBS control using TAQMAN®-based qPCR assays (FIG. 8).

Figure 9:
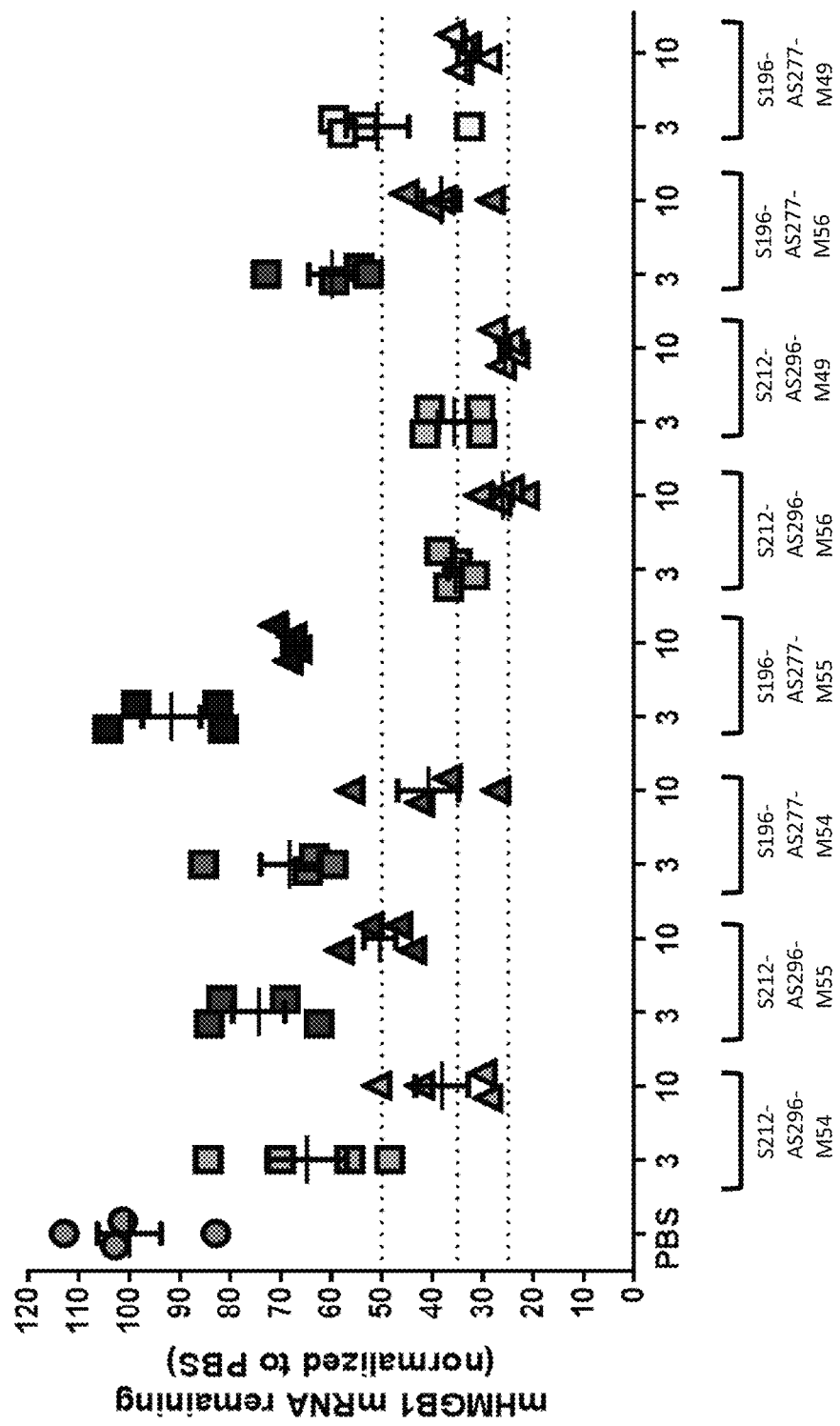
FIG. 9 is a graph showing an in vivo activity evaluation of GalNAc-conjugated HMGB1 oligonucleotides in a nicked tetraloop structure. Two different oligonucleotide sequences were tested with four different oligonucleotide modification patterns (denoted as M49, M54, M55, M56, which contain different arrangements of 2'-fluoro and 2'-O-methyl modified nucleotides, phophorothiate linkages, and included a phosphate analog positioned at the 5' terminal nucleotide of their antisense strands). Oligonucleotides were subcutaneously administered to mice at two different dosages (3 mg/kg and 10 mg/kg). The data show the amount of HMGB1 mRNA remaining at 24 hours after administration normalized to a PBS control treatment.
Figure 10:
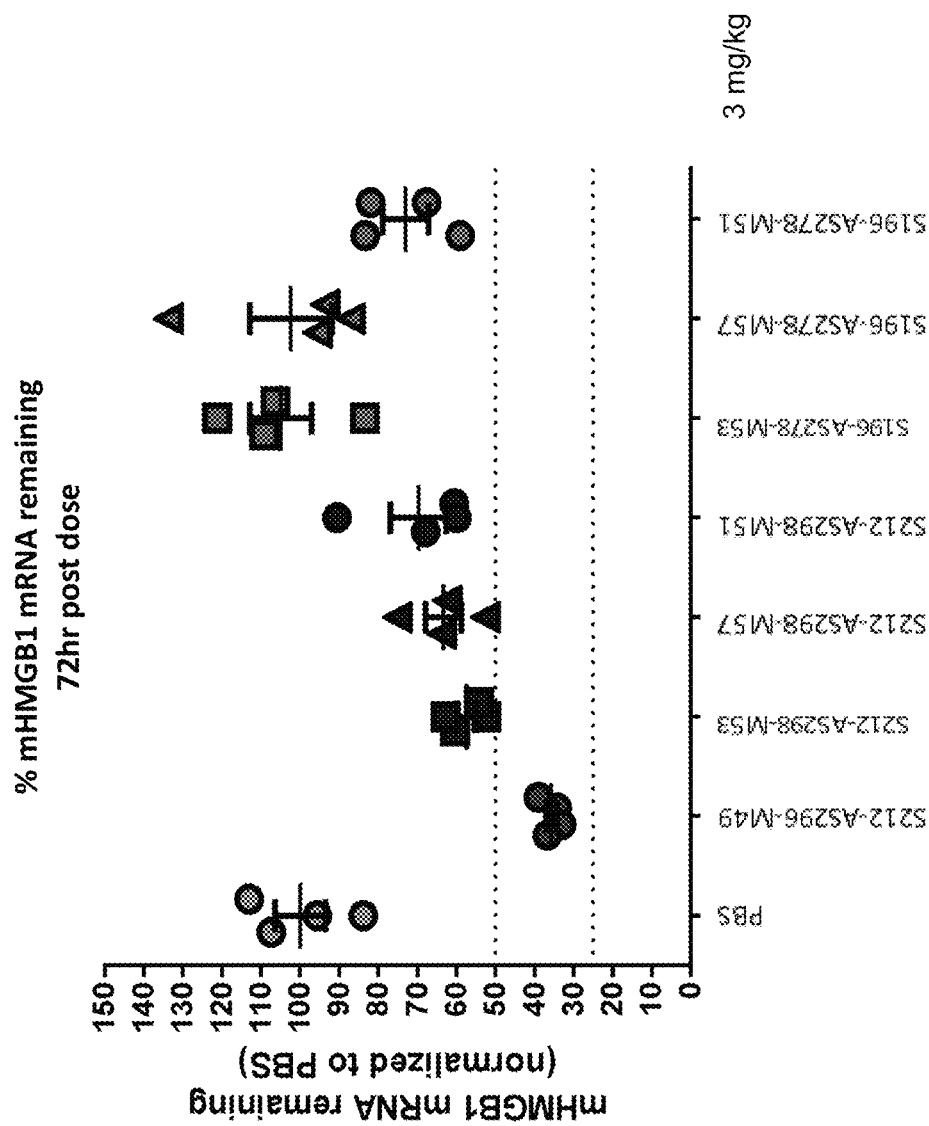
FIG. 10 is a graph showing an in vivo activity evaluation of GalNAc-conjugated HMGB1 oligonucleotides in a nicked tetraloop structure. Different oligonucleotide sequences were tested in four different oligonucleotide modification patterns (denoted as M49, M51, M53, M57). Oligonucleotides were subcutaneously administered to mice at 3 mg/kg. The data show the amount of HMGB1 mRNA remaining at 72 hours after administration normalized to a PBS control treatment.

Two of the RNAi oligonucleotides were selected for further testing using different modification patterns at 3 mg/kg or 3 mg/kg and 10 mg/kg. Again, the percentage of HMGB1 mRNA remaining at 72 hours after oligonucleotide administration compared to a PBS control was interrogated using TAQMAN®-based qPCR assays (FIG. 9 and FIG. 10, respectively). The oligonucleotides were tested in different modification patterns denoted as M49, M54, M55, M56, which comprise in their sense and antisense strands 2'-fluoro and 2'-O-methyl modified nucleotides in different arrangements and phosphorothioate and phosphodiester linkages, and include in their antisense strands a phosphate analog positioned at the 5' terminal nucleotide.

Figure 11:
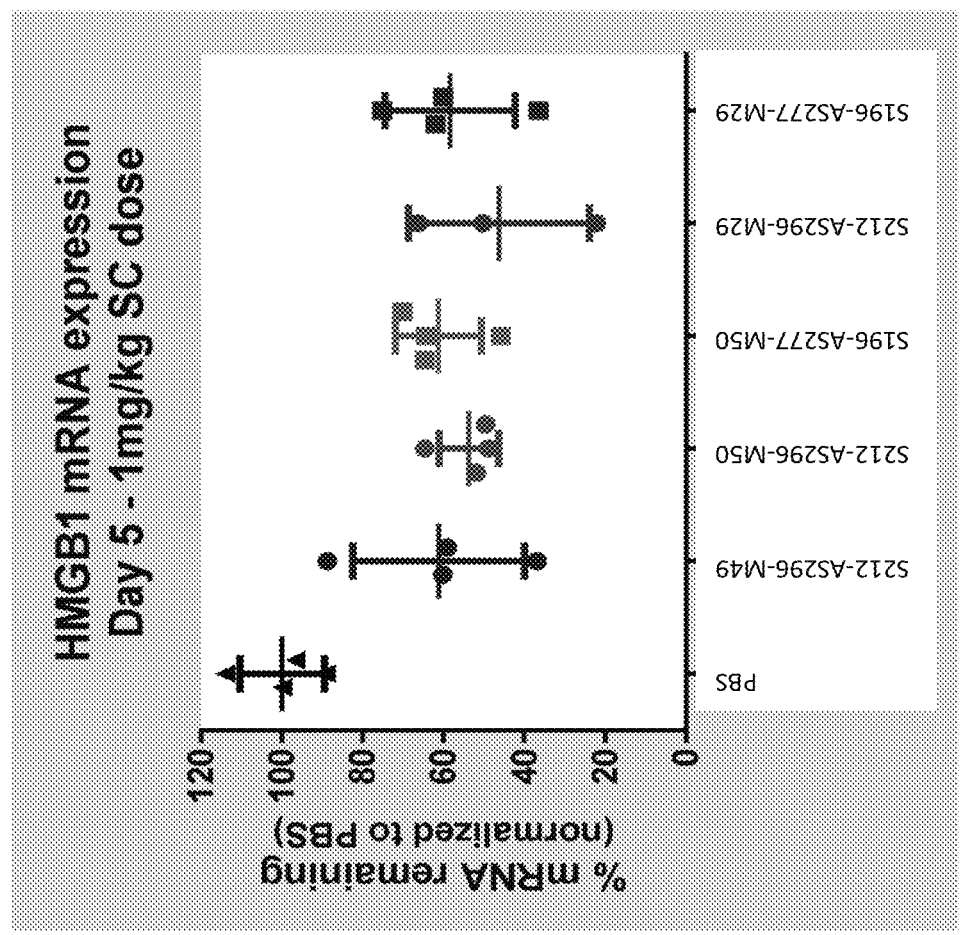
FIG. 11 is a graph showing an in vivo activity evaluation of GalNAc-conjugated HMGB1 oligonucleotides in a nicked tetraloop structure. Two different oligonucleotide sequences were tested in different modification patterns (denoted as M29, M49, and M50). The HMGB1 oligonucleotides were designed to bind to conserved sequences identified by the algorithm in the human, rhesus, and mouse sequences ("triple common" sequences). The data show the amount of HMGB1 mRNA remaining at day 5 (normalized to a PBS control treatment) after a 1 mg/kg subcutaneous dose.

The percentage of HMGB1 mRNA remaining at day 5 (as compared to a PBS control) after a 1 mg/kg subcutaneous dose of GalNAc-conjugated HMGB1 RNAi oligonucleotides containing nicked tetraloop structures was determined for oligonucleotides of the same sequence with different modifications (FIG. 11) as well as oligonucleotides of different sequence that retained the same modification pattern.

The triple-common sequences were also tested alongside sequences that were only identified in human HMGB1 gene ("human uniques") for activity in mice that were hydrodynamically injected with the RNAi oligonucleotides (HDI mice). Briefly, mice were intravenously administered 2 mL of human HMGB1 and NEOMYCIN plasmid—containing solution over seven seconds through the tail vein. 1 mg/kg RNAi oligonucleotide was subcutaneously injected into each mouse four days prior to HDI injection. The percentage of remaining HMGB1 mRNA was subsequently determined (normalized to NEO-168) using TAQMAN®-based qPCR assays. These results demonstrated that RNAi oligonucleotides complementary the triple common sequences selected from the previous screening downregulate HMGB1 expression more strongly than selected oligonucleotides that bound only the human unique sequences.

Example 2: Evaluation of Treatment in Models of Hepatotoxic Agents

Candidate RNAi oligonucleotides identified in Example 1 were further tested in models of APAP-induced (acetaminophen-induced) liver injury. Acetaminophen is known to be metabolized and form the active metabolite N-acetyl-p-benzoquinone imine (NAPQI). NAPQI binds to mitochondrial proteins to form NAPQI protein adducts, leading to hepatocyte necrosis.

Model 1—APAP

Figure 12:
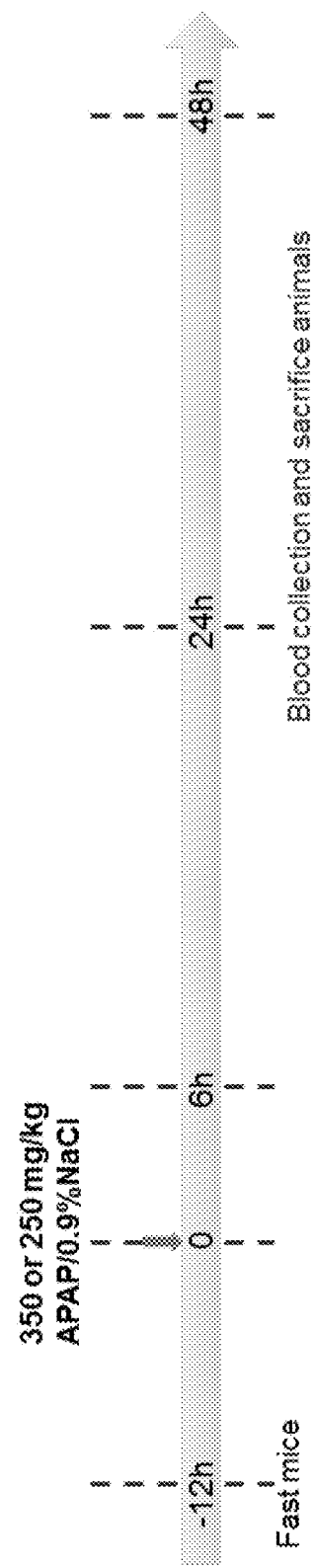
FIG. 12 is a schematic showing the flowchart of an experimental model for APAP-induced liver injury with C57BL/6 male mice (10 to 11 weeks). In this model, mice received an intraperitoneal injection of 350 or 250 mg/kg APAP after a fasting period of 12 hours. Blood and/or tissue samples were collected at 6, 24, and 48 hours.

Groups of 10 C57BL/6 male mice (10-11 weeks old) were fasted for 12 hours prior to administration of 250 or 350 mg/kg APAP in a 0.9% NaCl intraperotineal injection. Blood and/or liver tissues were collected at 6, 24, and 48 hours. Endpoint measurements for the study were quantification of liver damage (ALT, AST, and GLDH-IDEXX levels), profiling biomarkers (serum/liver HMGB1 levels and miR122 levels through ELISA, Western blots, and RT-qPCR), and liver staining (H&E, HMGB1, Ly6-B, and F4/80 staining). See schematic in FIG. 12.

Figure 13A:
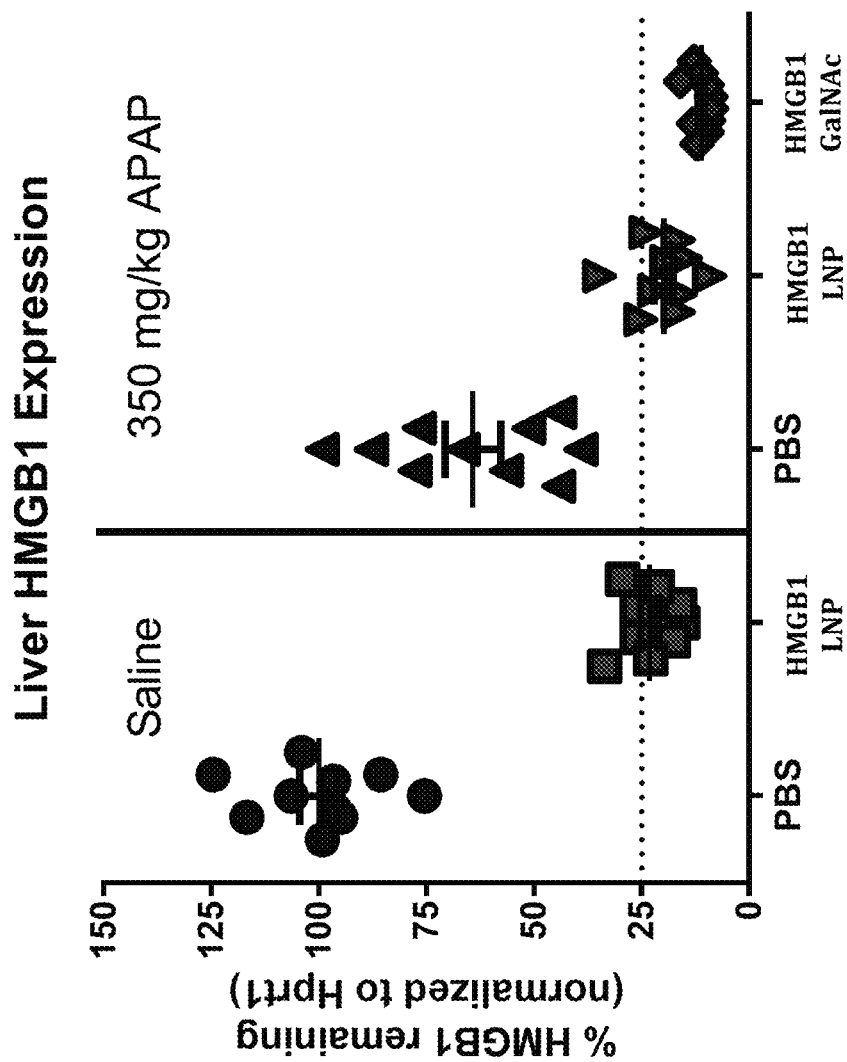

FIGS. 13A and 13B show the percentage of HMGB1 remaining in the liver (normalized to Hprt1) and serum (mg/mL) of animals treated with 350 mg/kg APAP versus a saline control injection. HMGB1 mRNA levels were interrogated using TAQMAN®-based qPCR assays. GalNAc conjugated RNAi oligonucleotides containing nicked tetraloop structures and RNAi oligonucleotides provided in a lipid nanoparticle formulation (LNP formulated RNAi oligonucleotides) downregulated >80% HMGB1 mRNA. However, serum HMGB1 was significantly reduced only in HMGB1-LNP treated animals. The HMGB1 oligonucleotide used in the experiments depicted in FIGS. 13A-13B is S212-AS296-M49.

Figure 14B:
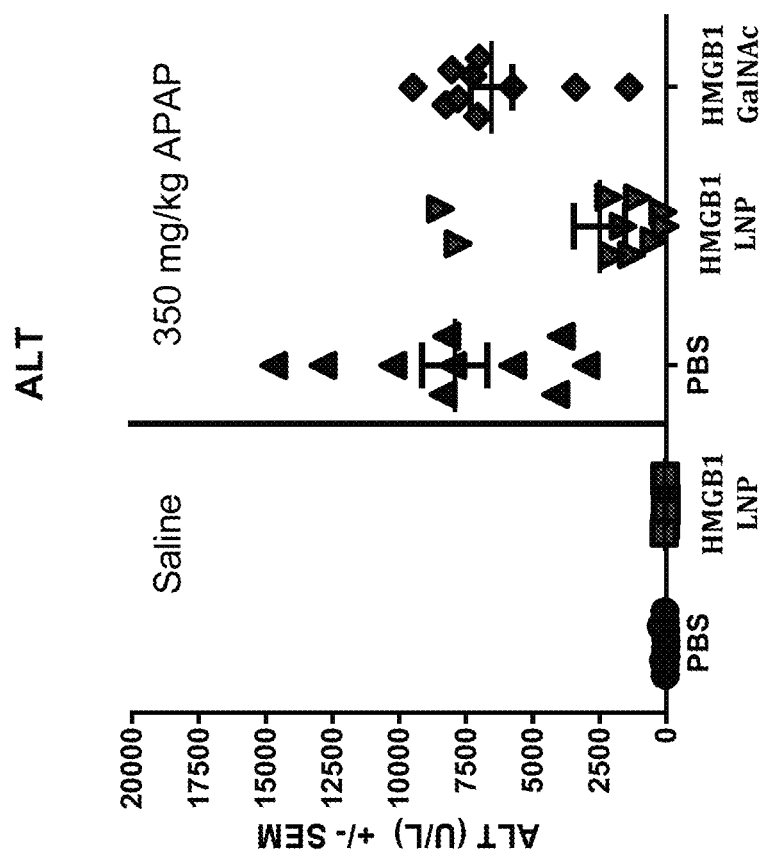
Figure 14C:
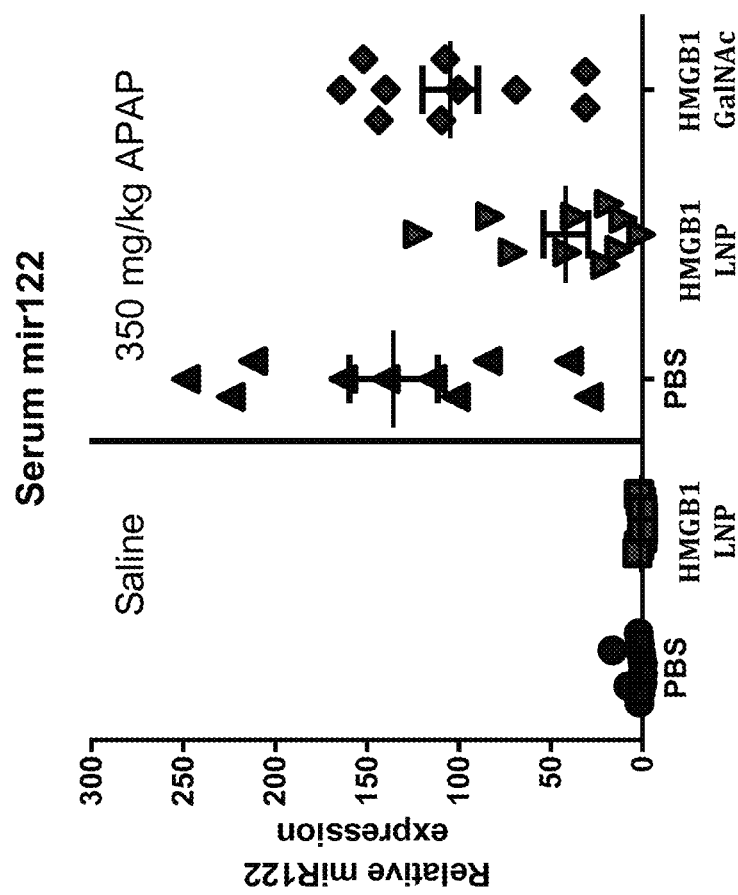

Liver function tests (LFTs) were also performed in animals treated with 350 mg/kg APAP. These experiments also demonstrated a decrease in hepatotoxicity according to serum AST, ALT, and miR122 levels in both LNP formulated and GalNAc conjugated HMGB1 oligonucleotides containing nicked tetraloop structures with a larger decrease seen when using the LNP formulated RNAi oligonucleotides (see FIGS. 14A-14C). The HMGB1 oligonucleotide in the experiments depicted in FIGS. 14A-14C is S212-AS296-M49.

Model 2—APAP

Figure 15:
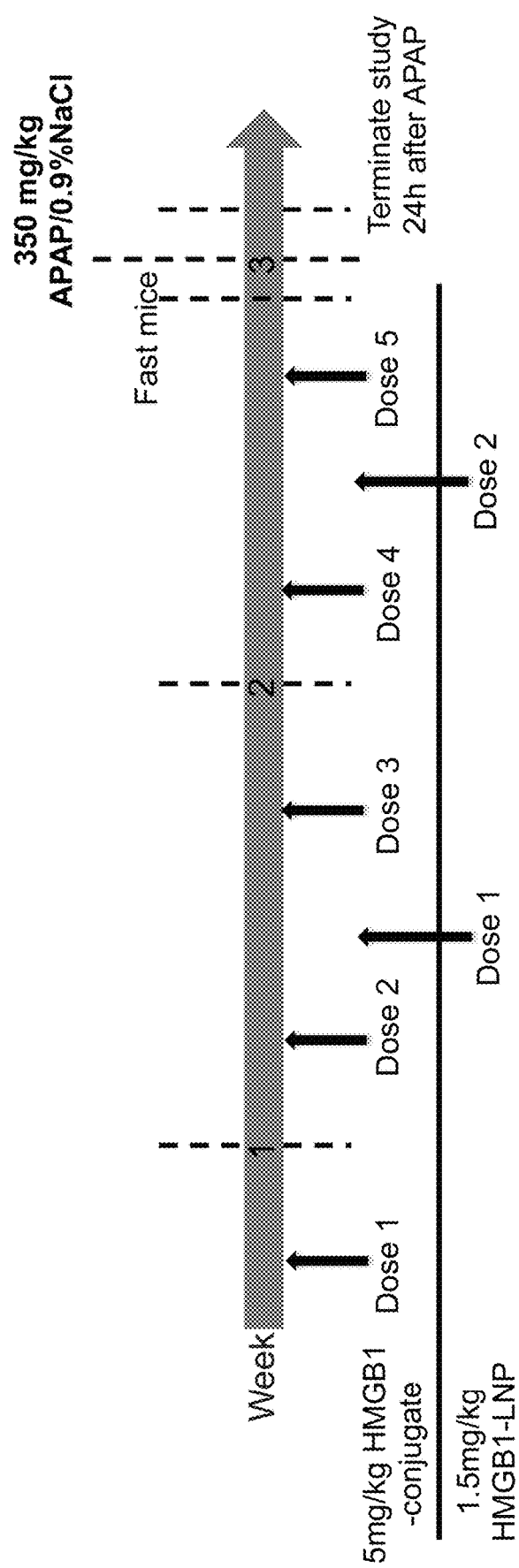
FIG. 15 is a schematic showing the flowchart of an experimental model for APAP-induced liver injury. In this model, animals were treated with either five doses of a GalNAc-conjugated HMGB1 oligonucleotides at 5 mg/kg or two doses of LNP formulated HMGB1 oligonucleotides at 1.5 mg/kg. Following a two-week period of administration of the oligonucleotides and a fasting period of 12 hours, mice received an intraperotineal (I.P.) injection of 350 mg/kg APAP in 0.9% NaCl. One day (24 hours) after administration of the APAP injection, tissue and/or blood samples were harvested.

In a second study using a model for APAP toxicity, groups of 10 C57BL/6 male mice (10-11 weeks old) were fasted for 12 hours prior to administration of 350 mg/kg APAP in a 0.9% NaCl intraperotineal injection. Animals were treated with 5 mg/kg of GalNAc-conjugated RNAi oligonucleotide containing nicked tetraloop structures or 1.5 mg/kg of LNP formulated RNAi oligonucleotide multiple times prior to APAP administration. Blood and/or liver tissues were collected 24 hours after APAP administration. Endpoint measurements for the study were quantification of liver damage (ALT, AST, and GLDH-IDEXX levels), profiling biomarkers (serum/liver HMGB1 levels and miR122 levels through ELISA and RT-qPCR), and liver staining (H&E and HMGB1 immunohistochemistry). See schematic shown in FIG. 15.

Figure 16B:
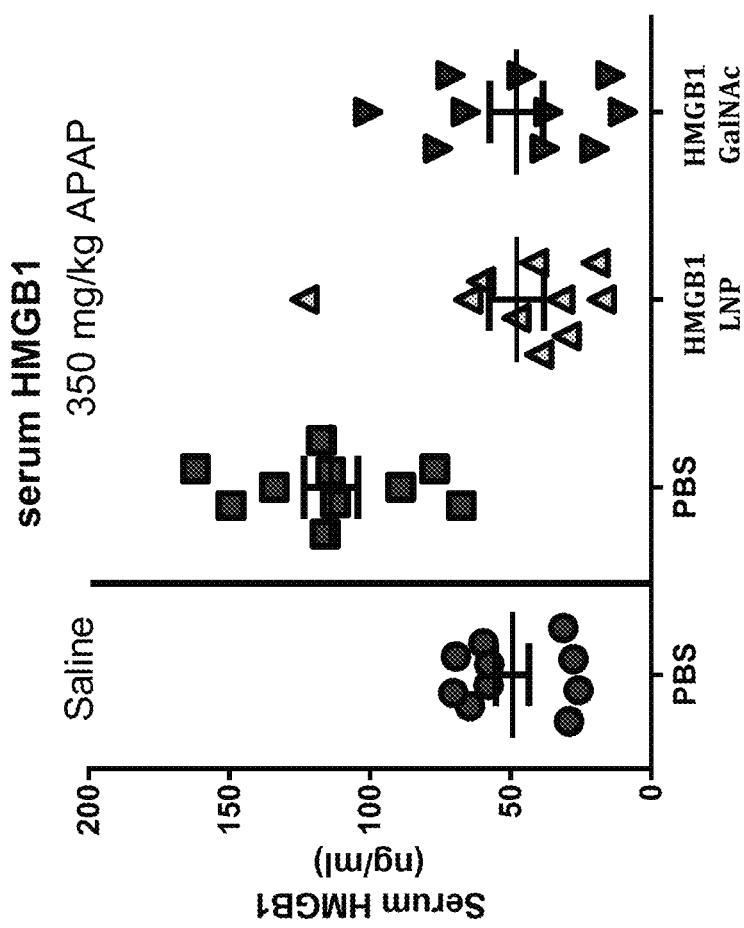
Figure 17B:
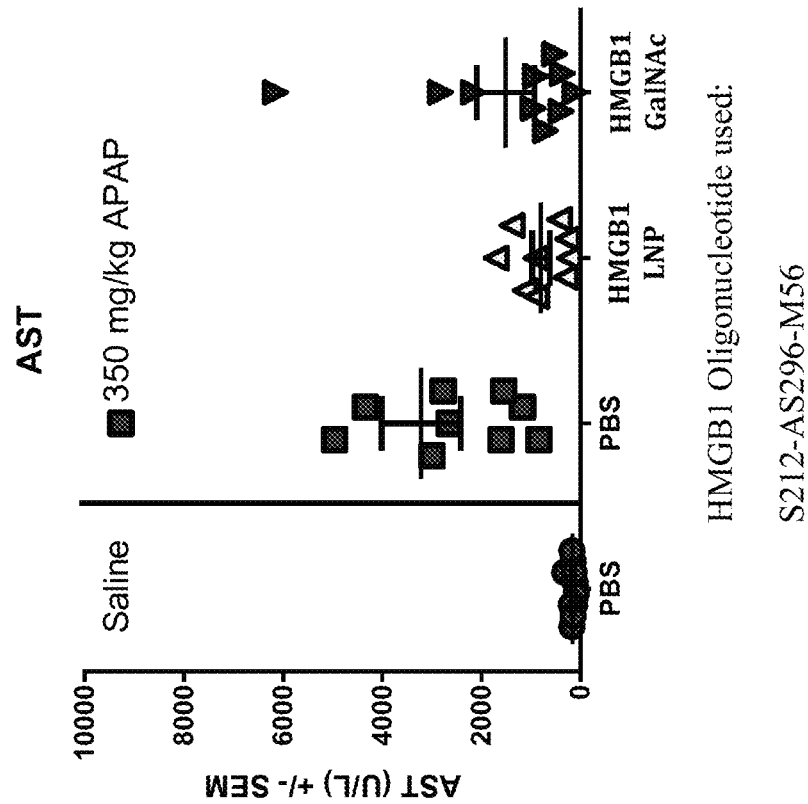
FIGS. 17A-17D are a series of graphs showing ALT (FIG. 17A), AST (FIG. 20B), LDH (FIG. 20C), and miR122 expression (FIG. 17D) in 350 mg/kg APAP treated animals after treatment with GalNAc-conjugated HMGB1 oligonucleotides, LNP formulated HMGB1 oligonucleotides, or a PBS control. Saline-injected animals were used as controls. The HMGB1 oligonucleotide used in FIGS. 17A-17D is S212-AS296-M56.
Figure 17A:
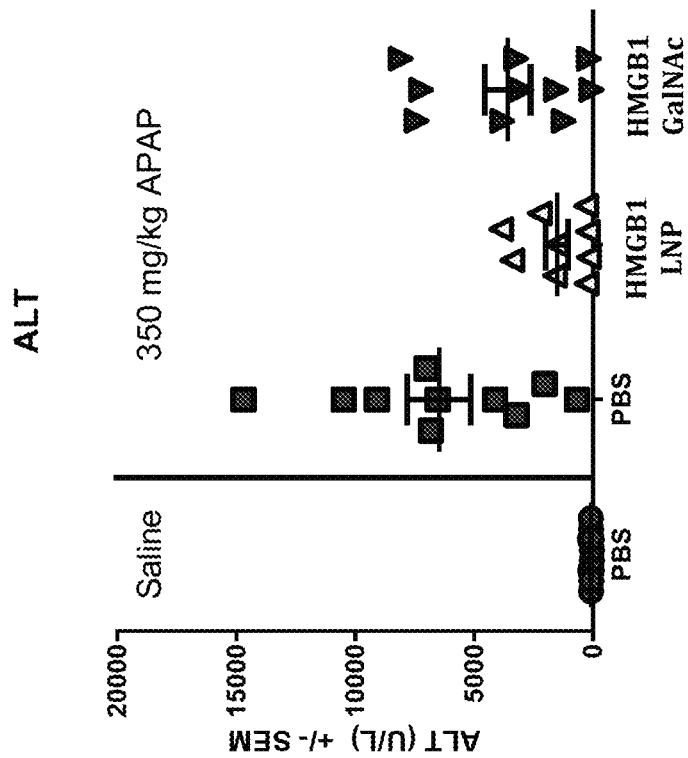
Figure 17D:
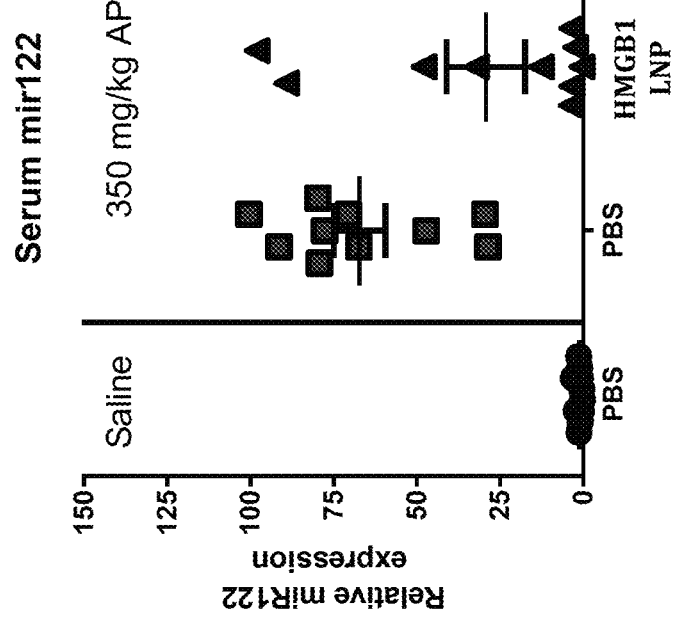
Figure 17C:
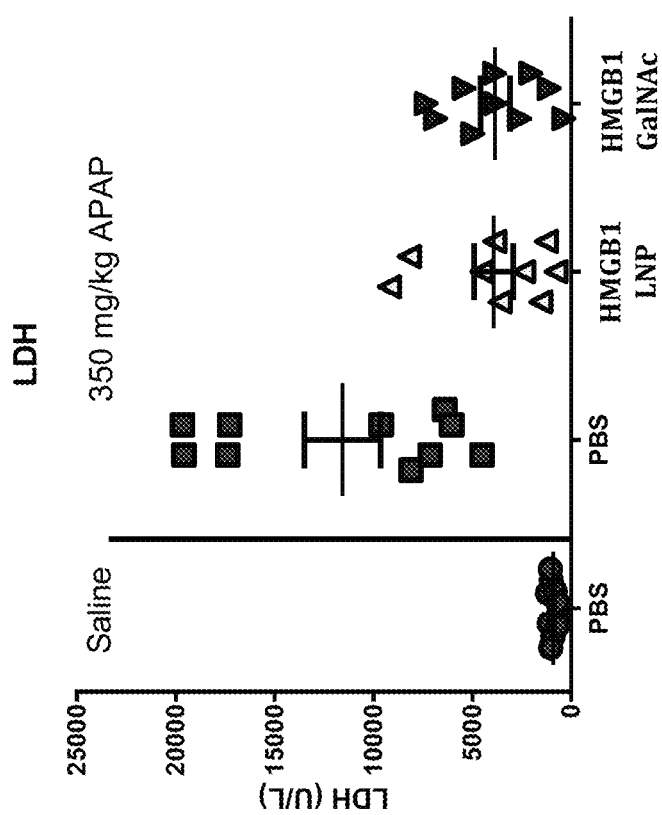

FIGS. 16A-16B show the percentage of HMGB1 remaining in the liver (normalized to Hprt1) and serum (mg/mL) of animals treated with 350 mg/kg APAP versus a saline control injection. HMGB1 mRNA levels were interrogated using TAQMAN®-based qPCR assays. GalNAc conjugated RNAi oligonucleotides containing nicked tetraloop structures and LNP formulated RNAi oligonucleotides downregulated >80% HMGB1 mRNA in the liver. Serum HMGB1 was also significantly reduced using both GalNAc conjugated RNAi oligonucleotides containing nicked tetraloop structures and LNP formulated RNAi oligonucleotides. The HMGB1 oligonucleotide used in the experiments depicted in FIGS. 16A-16B is S212-AS296-M56.

Further, ALT, AST, LDH, and serum miR122 levels were measured in APAP-treated mice and demonstrated that administration of GalNAc conjugated or LNP formulated HMGB1 oligonucleotides inhibited liver damage (see FIGS. 17A-17D). The HMGB1 oligonucleotide used in the experiments depicted in FIGS. 17A-17D is S212-AS296-M56.

Collectively, the studies using APAP toxicity models demonstrated that HMGB1 oligonucleotide treated animals have decreased HMGB1 serum levels and liver injury when compared to control animals.

Model 3—Carbon Tetrachloride

Figure 18:
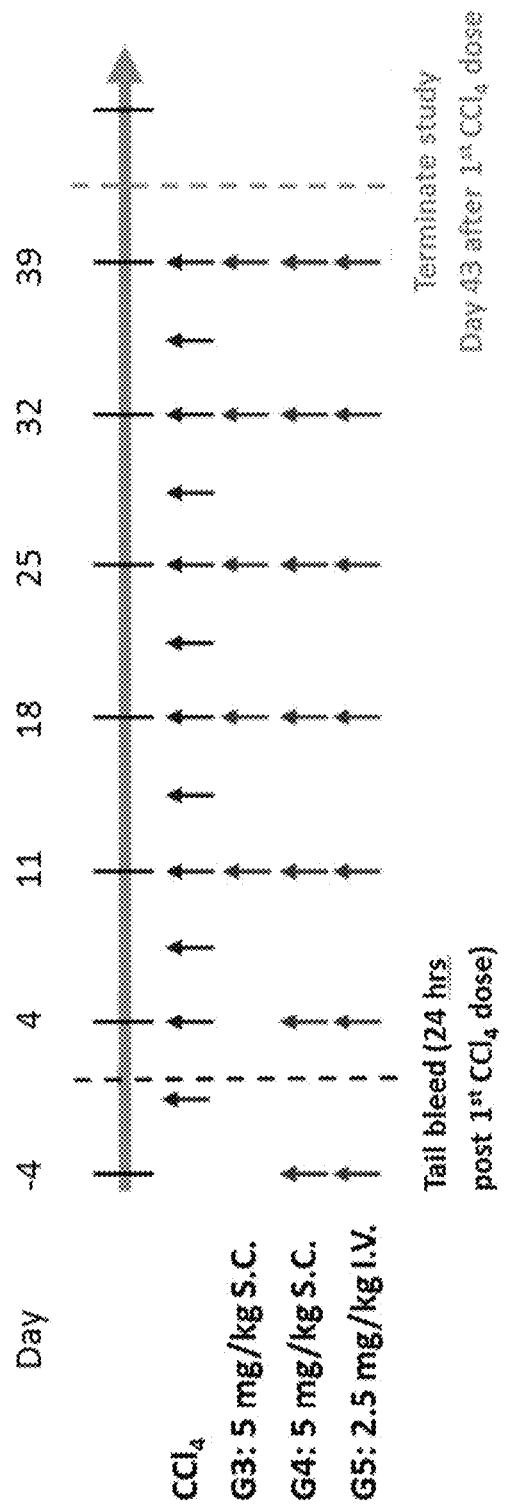
FIG. 18 is a schematic showing the flowchart of a carbon tetrachloride ($CCl_4$) model for anti-fibrotic activity with GalNAc-conjugated HMGB1 oligonucleotide dosing regimens.
Figure 19:
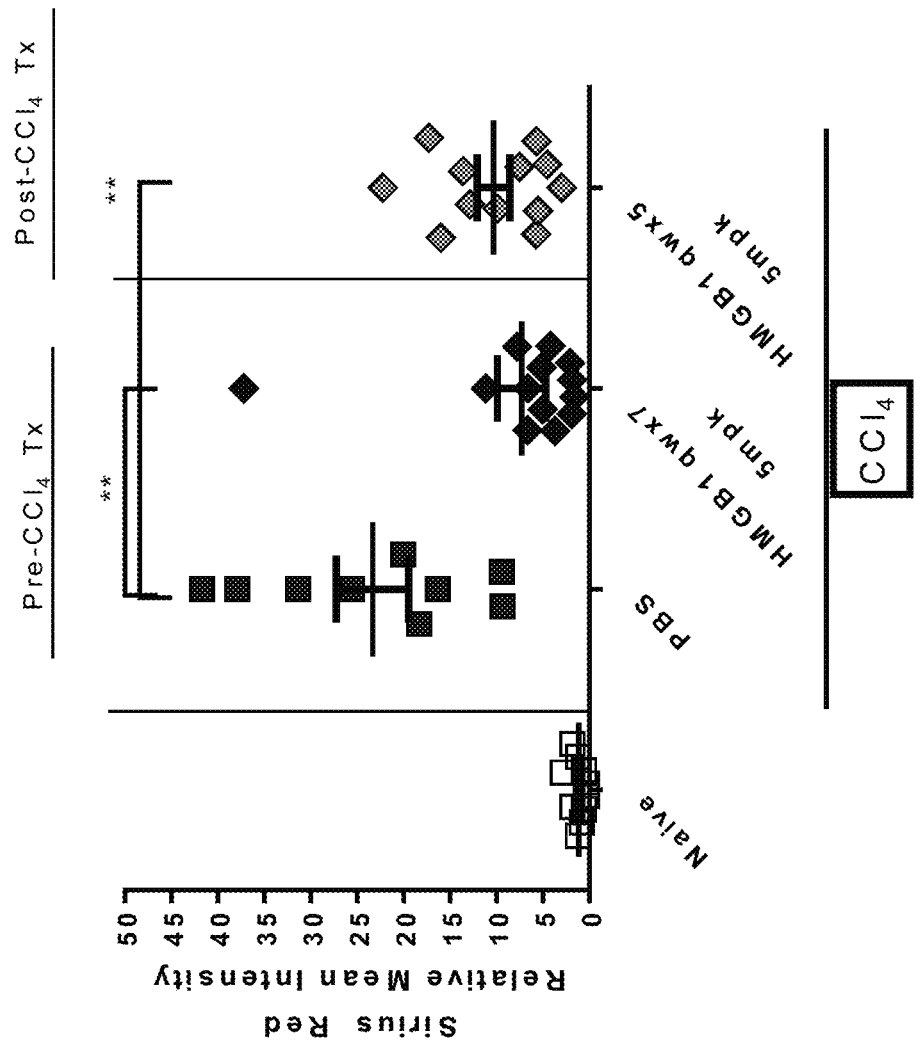
FIG. 19 is a graph of Sirius Red relative mean intensity levels in a $CCl_4$ model for anti-fibrotic activity after treatment with a subcutaneous 5 mg/kg dose of GalNAc-conjugated HMGB1 oligonucleotides every 5 or 7 weeks or a PBS control. The HMGB1 oligonucleotide used in FIG. 19 is S212-AS296-M49.
Figure 20:
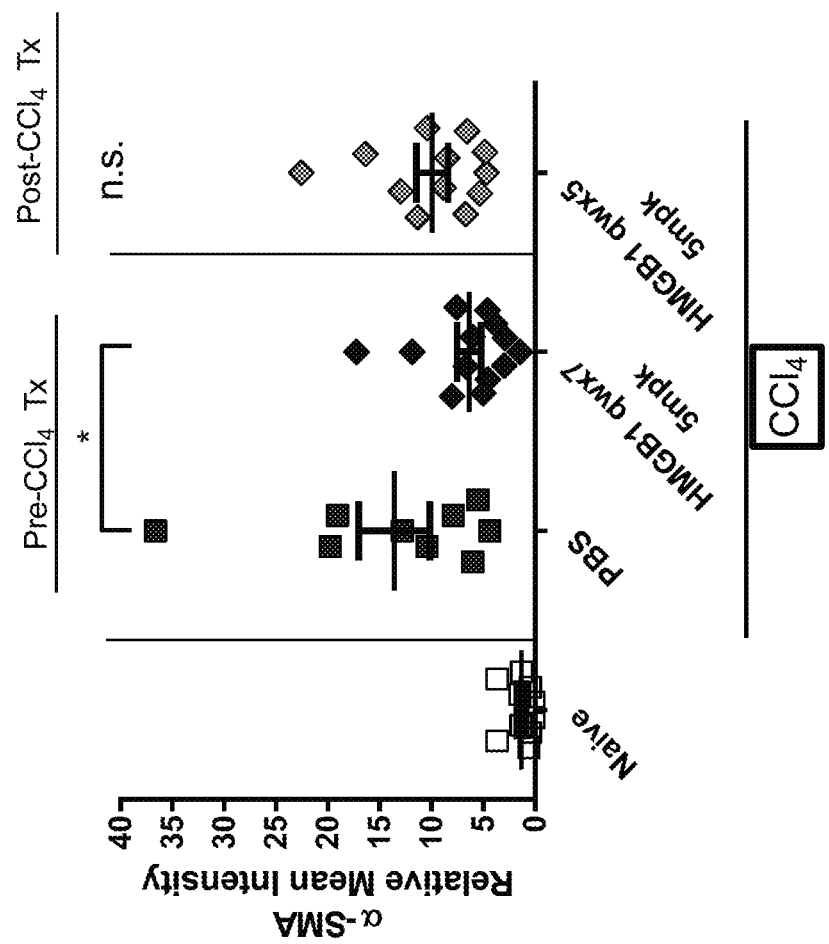
FIG. 20 is a graph of alpha-smooth muscle actin relative mean intensity levels in a $CCl_4$ model for anti-fibrotic activity after treatment with a subcutaneous 5 mg/kg dose of GalNAc-conjugated HMGB1 oligonucleotides every 5 or 7 weeks or a PBS control. The HMGB1 oligonucleotide used in FIG. 20 is S212-AS296-M49.
Figure 21:
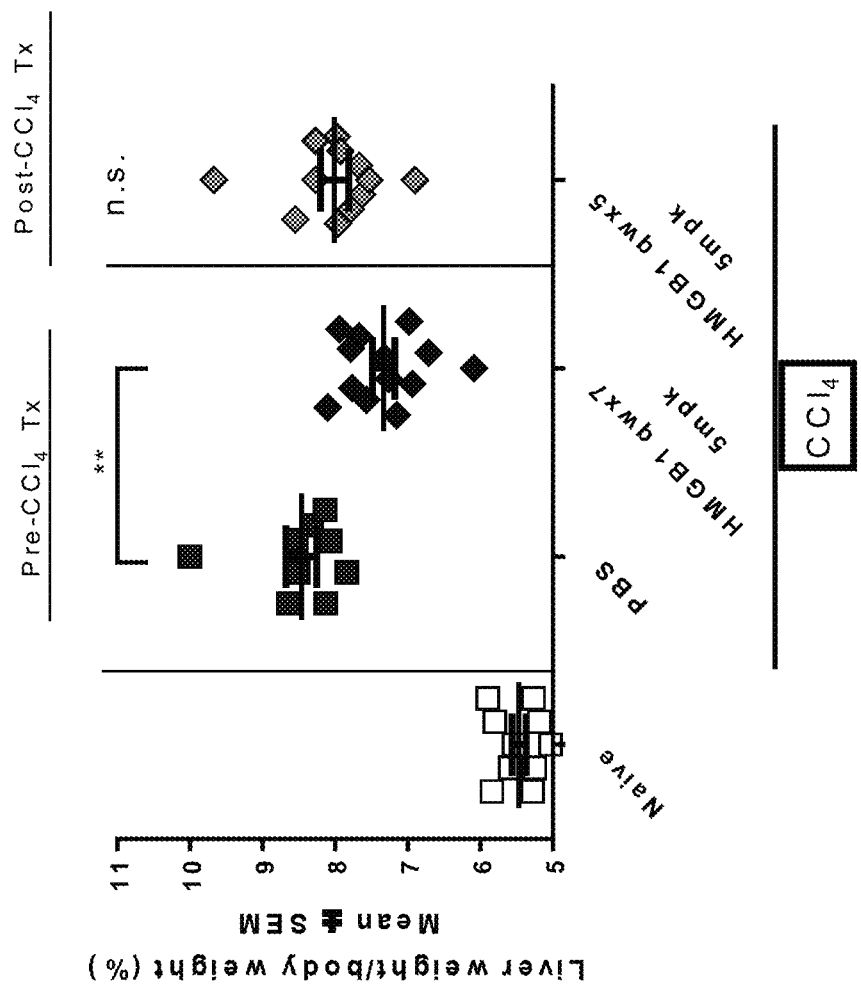
FIG. 21 is a graph of liver weight to body weight ratios in a $CCl_4$ model for anti-fibrotic activity after treatment with a subcutaneous 5 mg/kg dose of GalNAc-conjugated HMGB1 oligonucleotides every 5 or 7 weeks or a PBS control. The HMGB1 oligonucleotide used in FIG. 21 is S212-AS296-M49.
Figure 22:
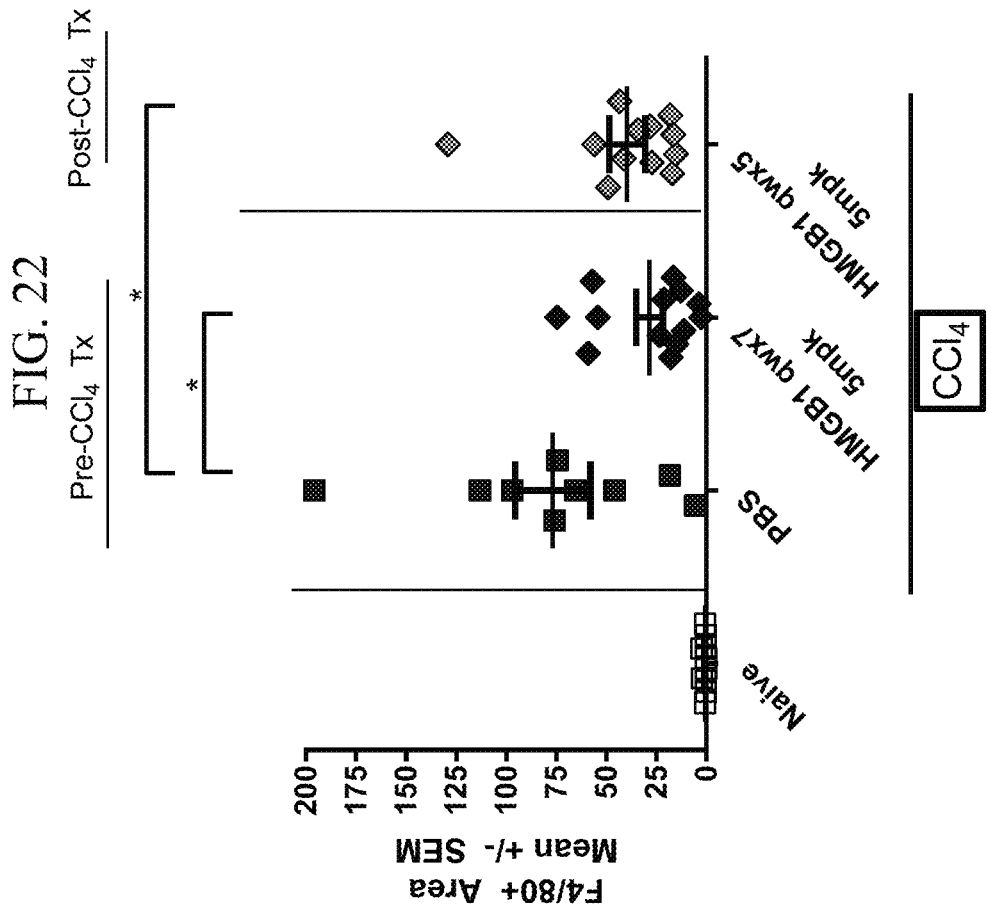
FIG. 22 is a graph of F4/80+ area in a $CCl_4$ model for anti-fibrotic activity after treatment with a subcutaneous 5 mg/kg dose of GalNAc-conjugated HMGB1 oligonucleotides every 5 or 7 weeks or a PBS control. The HMGB1 oligonucleotide used in FIG. 22 is S212-AS296-M49.

Groups of mice were administered 3 μl per gram of body weight carbon tetrachloride mixed with olive oil ($CCl_4$:olive oil at a 1:5 v/v ratio) or an olive oil control solution twice per week for six weeks through intraperotineal injection. As shown in Table 4 and FIG. 18, animals were randomized into the groups shown and either left untreated or were treated with GalNAc-conjugated HMGB1 oligonucleotides containing nicked tetraloop structures or PBS via subcutaneous (S.C.) or intravenous (I.V.) injection once per week for 5 or 6 wks according to study design.

TABLE 4

Group Designation and compound dosing schedule

| Group | $CCl_4$ | Treatment | Dose (mg/kg) | Volume (ml/kg) | Dosing start | Frequency and days of dosing | No. mice | Route |
|---|---|---|---|---|---|---|---|---|
| 1 | Olive oil | — | — | — | — | — | 10 | — |
| 2 | $CCl_4$ | PBS | 0 | 10 | Day −4 | qw × 6 weeks | 10 | S.C. |
| 3 | $CCl_4$ | GalNAc-conjugated HMGB1 oligo | 5 | 10 | Day 11 | qw × 5 weeks | 10 | S.C. |
| 4 | $CCl_4$ | GalNAc-conjugated HMGB1 oligo | 5 | 10 | Day −4 | qw × 6 weeks | 10 | S.C. |
| 5 | $CCl_4$ | LNP HMGB1 oligo | 2.5 | 10 | Day-4 | qw × 6 weeks | 10 | I.V. |

Several parameters indicative of liver injury were examined in the mice at the end of the study. Significant reductions were seen in both fibrosis (using Sirius Red staining) and macrophage infiltration and activation (using immunohistochemistry analysis with an antibody specific for the F4/80 protein, which is a mouse macrophage marker) in both groups of HMGB1 RNAi oligonucleotide-treated animals when compared to PBS-treated animals. Significant reductions were also seen in stellate cell activation (measured through α-SMA staining) and hepatomegaly (measured using liver weight to body weight ratio) using the longer dosing regimen data shown in FIGS. 19-22). The HMGB1 RNAi oligonucleotides used in this study are identified as S212-AS296-M49, and have monovalent GalNac moieties conjugated at each of the four nucleotide positions of the GAAA loop.

Figure 23:
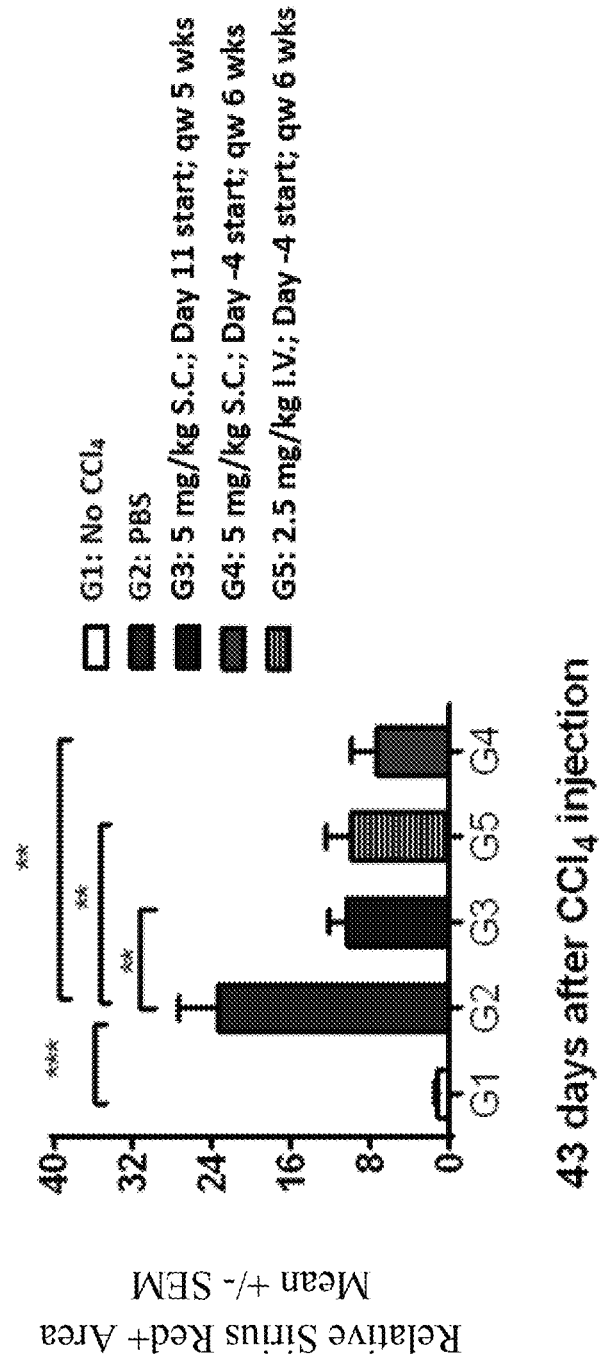
FIG. 23 is a graph of Sirius Red relative mean intensity levels in a $CCl_4$ model for anti-fibrotic activity 43 days after treatment with a 5 mg/kg subcutaneous dose GalNAc-conjugated HMGB1 oligonucleotides in a tetraloop structure or a 2.5 mg/kg intravenous dose of LNP-formulated oligonucleotide in a tetraloop structure. PBS-treated animals and animals untreated with $CCl_4$ were used as controls. The HMGB1 oligonucleotide used in FIG. 23 is S212-AS296-M49.

Additionally, livers from animals treated as above with carbon tetrachloride were examined at 43 days post-injection using Sirius Red staining. These experiments revealed that administration of GalNAc-conjugated HMGB1 RNAi oligonucleotide containing a nicked tetraloop structure (either at a 5 mg/kg subcutaneous dose or a 2.5 mg/kg intravenous dose) significantly reduced the relative Sirius Red-positive area in liver samples, indicating that liver fibrosis in these animals was significantly reduced (FIG. 23). The HMGB1 oligonucleotide used in the experiments depicted in FIG. 23 is S212-AS296-M49.

Example 3: Evaluation of Treatment in Model of Autoimmune Liver Disease

Figure 24:
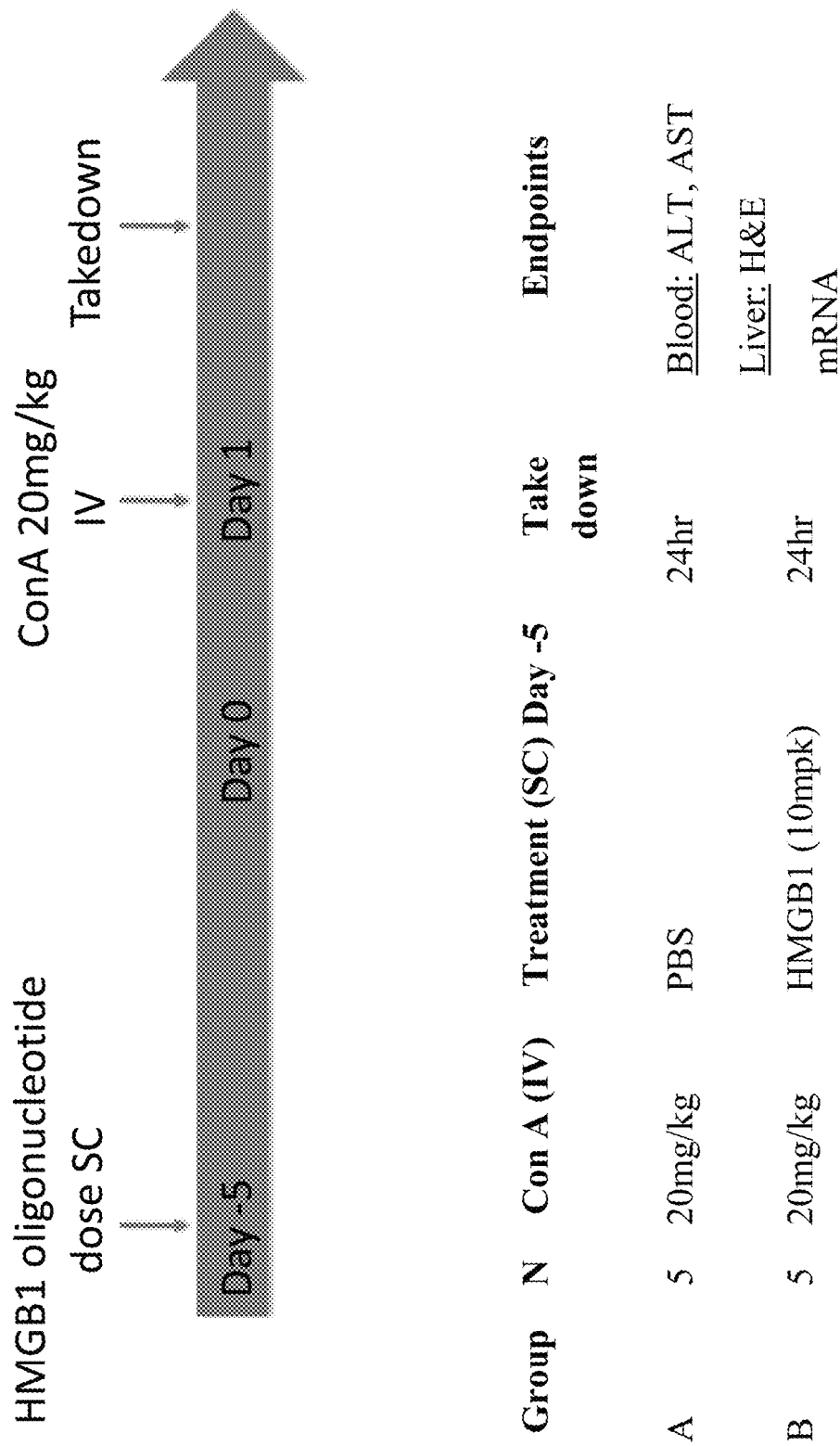
FIG. 24 is a schematic showing the flowchart for a Concavalin A induced hepatitis model in mice alongside a chart showing a basic outline of the experimental design.
Figure 25:
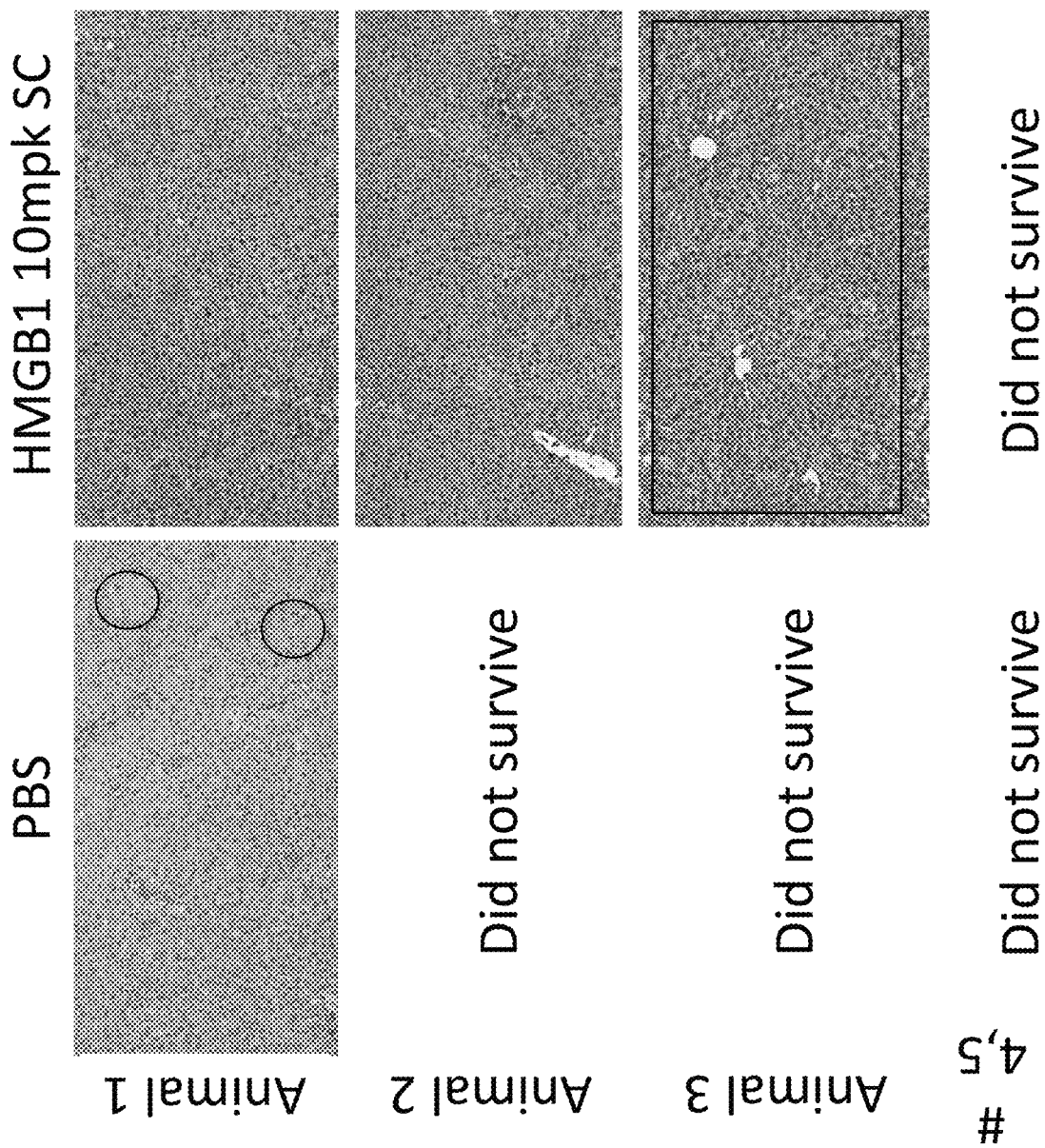
FIG. 25 is a series of pictures demonstrating the results of GalNAc-conjugated HMGB1 oligonucleotide treatment in a Concavalin A model of induced hepatitis in mice. Data from mice treated with PBS control are shown at left. Data from mice treated with a subcutaneous dose of 10 mg/kg of GalNAc-conjugated HMGB1 oligonucleotides are shown at right. The HMGB1 oligonucleotide used in FIG. 25 is S212-AS296-M49.

Two groups of five C57BL/6 male mice (10-11 weeks old) were treated with 20 mg/kg of intravenous concavalin A six days after subcutaneous administration of either 10 mg/kg GalNAc-conjugated HMGB1 oligonucleotide containing a nicked tetraloop structure or PBS. One day following concavalin A administration, the animals were examined for ALT and AST serum levels as well as H&E staining of the liver (experimental schematic shown in FIG. 24). FIG. 25 demonstrates that animals were three times more likely to survive when treated with the GalNAc-conjugated HMGB1 RNAi oligonucleotide containing a nicked tetraloop structure than with PBS. Further, surviving HMGB1 oligonucleotide-treated animals had less necrosis in H&E stained samples of liver than the PBS controls. The HMGB1 oligonucleotide used in the experiments depicted in FIG. 25 is S212-AS296-M49.

Example 4: Evaluation of Treatment in Model of Choline-Deficient Amino Acid-Defined High-Fat Diet (CDAHFD)

C57Bl/6 mice were fed either a control high-fat diet (CDHFD) or a choline deficient amino acid defined high fat diet (CDAHFD) and normal or sugar water. CDAHFD has a lower methionine content than CDHFD. As a result of the difference in methionine content, CDHFD is expected to generate steatosis, but is not expected to generate the NAFLD-like liver pathology seen in the CDAHFD diet. As shown in Tables 5 and 6, the animals were left untreated or were administered a PBS control or GalNAc-conjugated HMGB1 RNAi oligonucleotides containing nicked tetraloop structures at 5 mg/kg for 6 weeks (subcutaneous administration) starting six weeks after the mice were placed on the high fat diets.

TABLE 5

Treatment of animals with high fat control diet and normal or sugar water

| Treatment | Diet | # mice | Necropsy week |
|---|---|---|---|
| — | CDHFD + normal water | 5 | 6 |
| — | CDHFD + normal water | 5 | 9 |
| PBS | CDHFD + normal water | 5 | 12 |
| GalNAc-conjugated HMGB1 oligo | CDHFD + normal water | 5 | 12 |
| — | CDHFD + sugar water | 5 | 6 |
| — | CDHFD + sugar water | 5 | 9 |
| PBS | CDHFD + sugar water | 5 | 12 |
| GalNAc-conjugated HMGB1 oligo | CDHFD + sugar water | 5 | 12 |

TABLE 6

Treatment of animals with choline deficient amino acid defined high fat diet (CDAHFD) and normal or sugar water

| Treatment | Diet | # mice | Necropsy week |
|---|---|---|---|
| — | CDAHFD + normal water | 5 | 6 |
| — | CDAHFD + normal water | 5 | 9 |
| PBS | CDAHFD + normal water | 5 | 12 |
| GalNAc-conjugated HMGB1 oligo | CDAHFD + normal water | 5 | 12 |
| — | CDAHFD + sugar water | 5 | 6 |
| — | CDAHFD + sugar water | 5 | 9 |
| PBS | CDAHFD + sugar water | 5 | 12 |
| GalNAc-conjugated HMGB1 oligo | CDAHFD + sugar water | 5 | 12 |

Figure 26B:
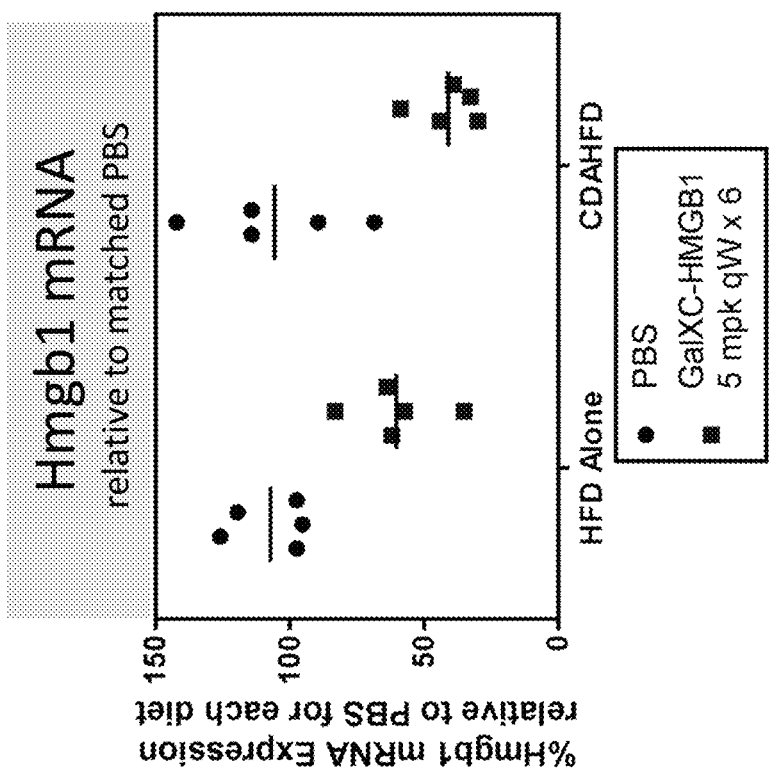
FIGS. 26A-26D are a series of graphs demonstrating the results of subcutaneous GalNAc-conjugated HMGB1 oligonucleotide treatment on HMGB1 (FIGS. 26A and 26B), Col1a1 (FIG. 26C), and Vimentin (FIG. 26D) mRNA levels in mice on a choline-deficient amino acid-defined high-fat diet (CDAHFD) or control high-fat diet (HFD) in comparison to PBS control treatment. The HMGB1 oligonucleotide used in FIGS. 26A-26D is S194-AS274-M30.
Figure 26A:
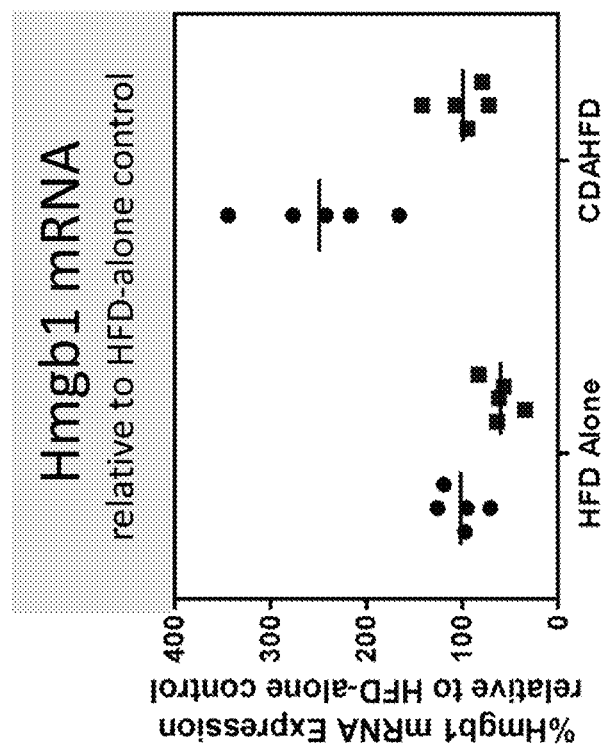
Figure 26C:
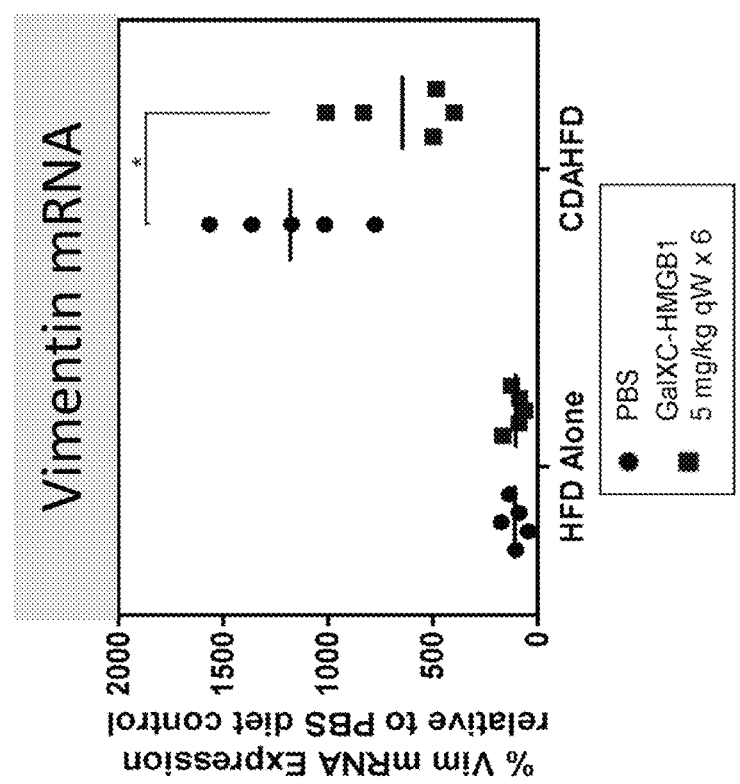
Figure 26D:
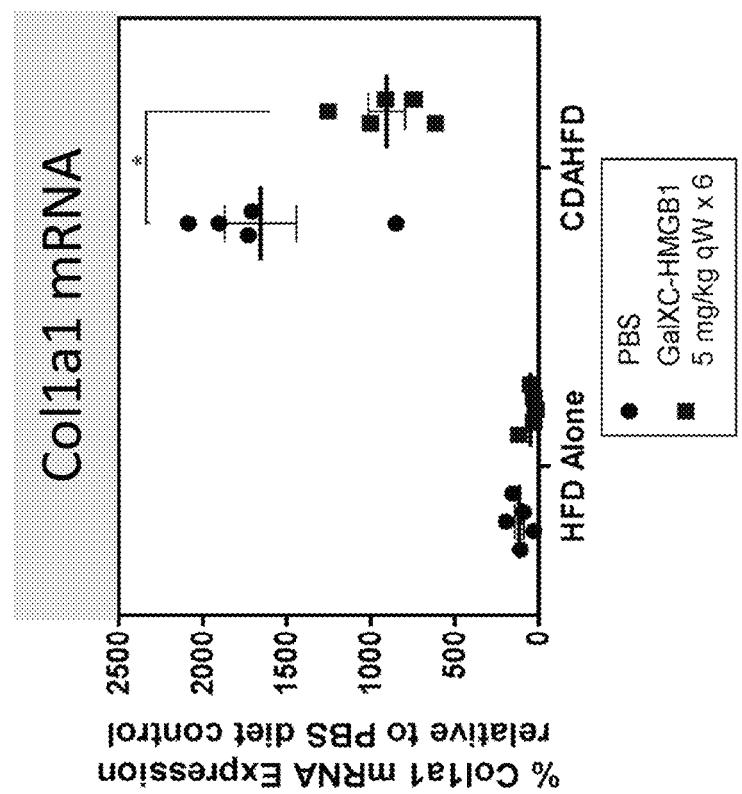

HMGB1 mRNA was elevated in mice that consumed the choline deficient amino acid defined high fat diet (CDAHFD) in comparison to the CDHFD control high-fat diet (FIGS. 26A and 26B). Further, Collagen 1a1 (Col1a1) and Vimentin mRNA levels were elevated by CDAHFD>100×, relative to the CDHFD alone (FIGS. 26C and 26D, respectively). GalNAc-conjugated HMGB1 oligonucleotides containing nicked tetraloop structures demonstrated significant reduction on these markers after 6 weeks of treatment.

Figure 27:
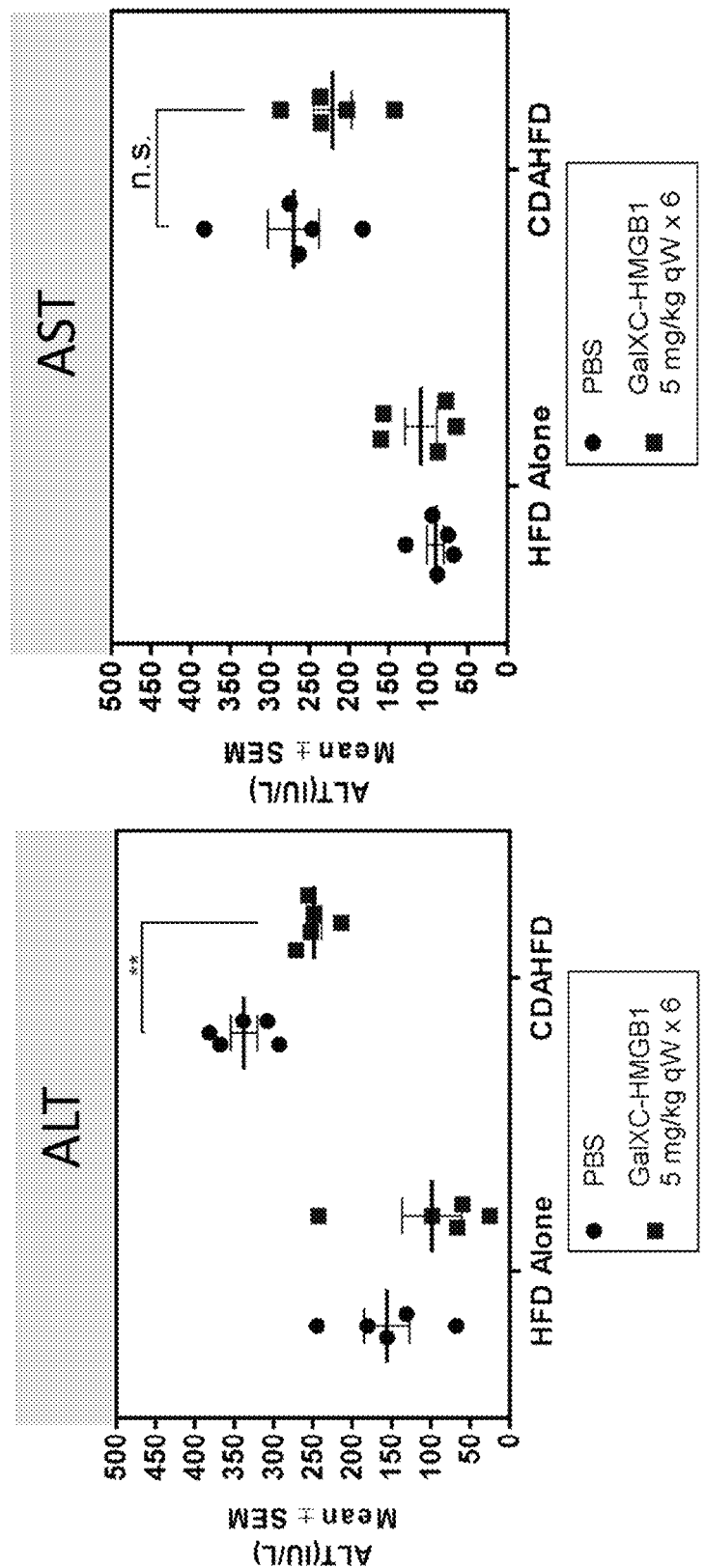
FIG. 27 is a set of graphs demonstrating the results of subcutaneous GalNAc-conjugated HMGB1 oligonucleotide treatment on ALT and AST levels in mice on a choline-deficient amino acid-defined high-fat diet (CDAHFD) or control high-fat diet (HFD) in comparison to PBS control treatment. The HMGB1 oligonucleotide used in FIG. 27 is S194-AS274-M30.

AST and ALT levels were also elevated in mice consuming CDAHFD, relative to mice consuming the control high fat diet (CDHFD) (FIG. 27). GalNAc-conjugated HMGB1 RNAi oligonucleotides demonstrated moderate reduction on these markers after 6 weeks of treatment. The HMGB1 oligonucleotide used in FIGS. 26A-26D and 27 is S194-AS274-M30. comprises in sense and antisense strands 2'-fluoro and 2'-O-methyl modified nucleotides in different arrangements and phosphorothioate and phosphodiester linkages, and include in its antisense strands a phosphate analog positioned at the 5' terminal nucleotide.

Example 5. Testing the Activity of Additional HMGB1 Oligonucleotides

All additional HMGB1 oligonucleotides used in this example were designed to bind to conserved sequences identified by the algorithm in the human, monkey (both rhesus), and mouse sequences ("triple common" sequences). The additional HMGB1 oligonucleotides were modified as described in Example 1 to contain tetraloops and adapt different modification patterns. The different modification patterns (e.g., designated M58, M59, M60, or M61) comprise in their sense and antisense strands 2'-fluoro and 2'-O-methyl modified nucleotides in different arrangements and phosphorothioate and phosphodiester linkages, and include in their antisense strands a phosphate analog positioned at the 5' terminal nucleotide. The oligonucleotide inhibitors were also conjugated to GalNAc moieties. Three GalNAc moieties were conjugated to nucleotides in the tetraloop of the sense strand. Conjugation was performed using a click linker as described in Example 1. The GalNAc-conjugated HMGB1 oligonucleotides were then tested for their ability to reduce HMGB1 mRNA expression in mice and in vitro in cultured hepatocytes.

Figure 28:
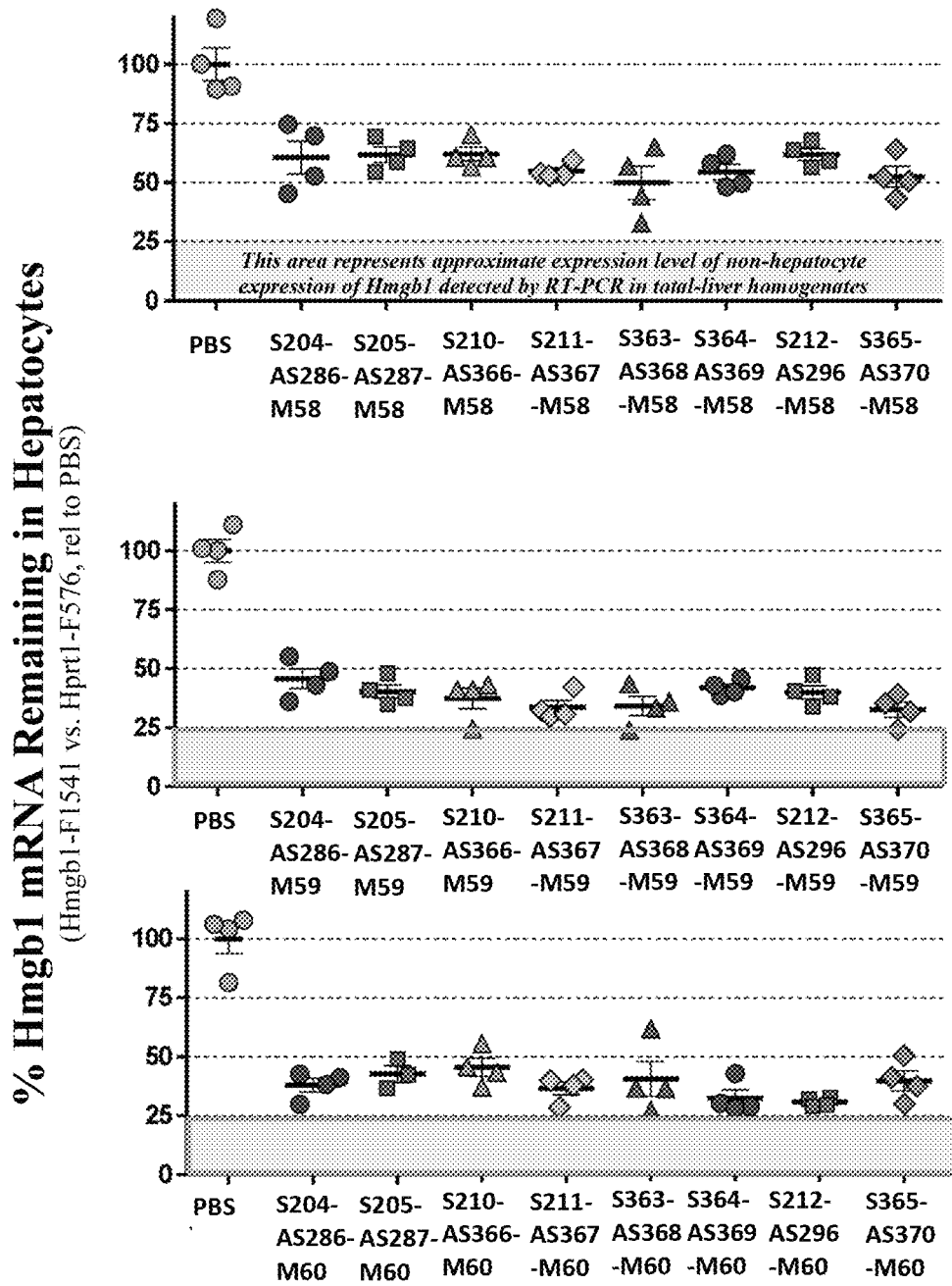
FIG. 28 is a graph showing an in vivo activity evaluation of eight GalNAc-conjugated HMGB1 oligonucleotides with 3 different modification patterns on day 5 following 1 mg/kg of subcutaneous administration. The percentage of remaining HMGB1 mRNA in the liver 5 days after administration of the oligonucleotides, normalized to the remaining HMGB1 mRNA levels in mice treated with PBS, is shown. The results show that all tested HMGB1 oligonucleotides with different chemical modification patterns are potent in knocking down HMGB1 in mice hepatocytes.

Eight different GalNAc-conjugated HMGB1 oligonucleotides (S204-AS286, S205-AS287, S210-AS366, S211-AS367, S363-AS368, S364-AS369, S212-AS296, and S365-AS370) with three different modification patterns (denoted M58, M59, and M60) were tested for their potency in knocking down HMGB1. One single dose (1 mg/kg) of indicated HMGB1 oligonucleotides with a specific modification pattern were injected subcutaneously to CD-1 mice. Mice were euthanized 5 days post injection and liver samples were obtained. RNA was extracted from the liver samples to evaluate HMGB1 mRNA levels by qPCR (normalized to HPRT1-F576, a housekeeping gene). The levels of remaining HMGB1 mRNA were interrogated using TAQMAN®-based qPCR assays. All tested HMGB1 oligonucleotides and modification patterns were potent in knocking down HMGB1, with modification patters M59 and M60 exhibiting higher potency (FIG. 28).

Figure 29A:
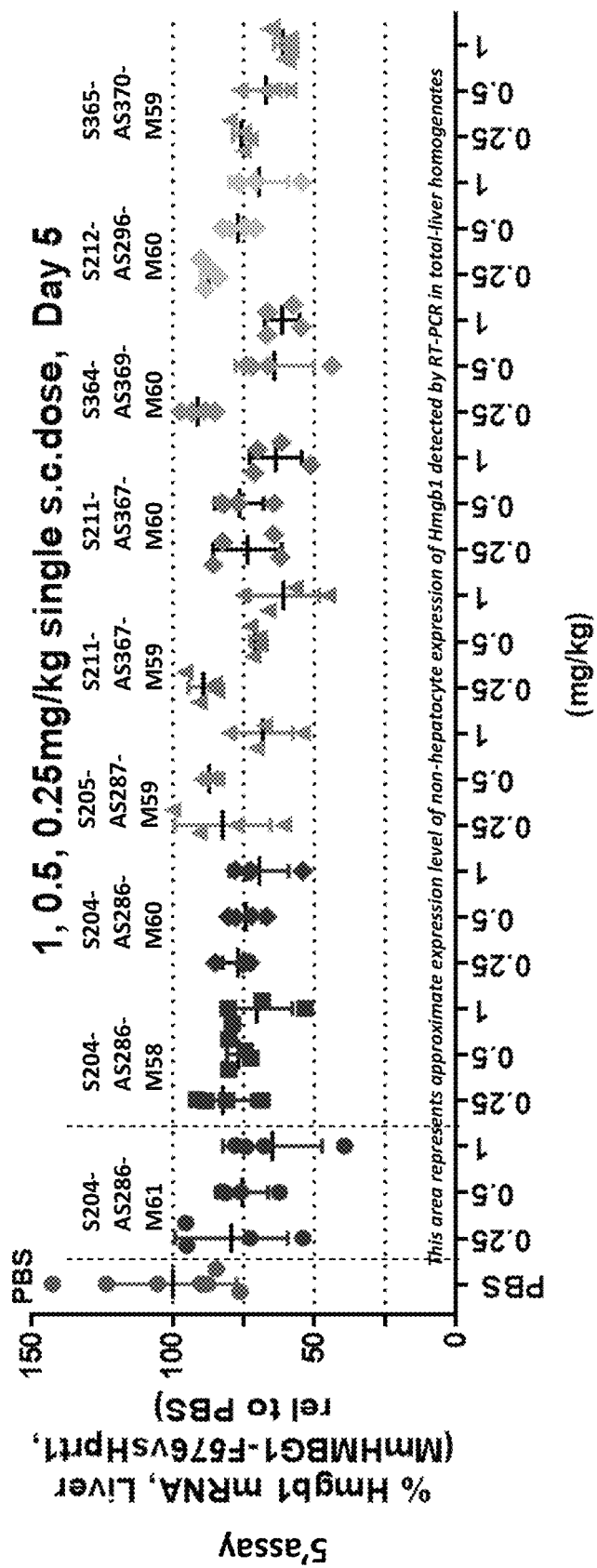
FIGS. 29A-29B are graphs showing an in vivo activity evaluation of eight GalNAc-conjugated HMGB1 oligonucleotides at three different dosages (1, 0.5, or 0.25 mg/kg). The percent remaining HMGB1 mRNA in the liver 5 days after administration of the oligonucleotides, normalized to the remaining HMGB1 mRNA levels in mice treated with PBS, was evaluated in either a 5' qPCR reaction (FIG. 29 A) or a 3' qPCR reaction (FIG. 29B). The results show that the potency of all tested HMGB1 oligonucleotides are dose-dependent.
Figure 29B:
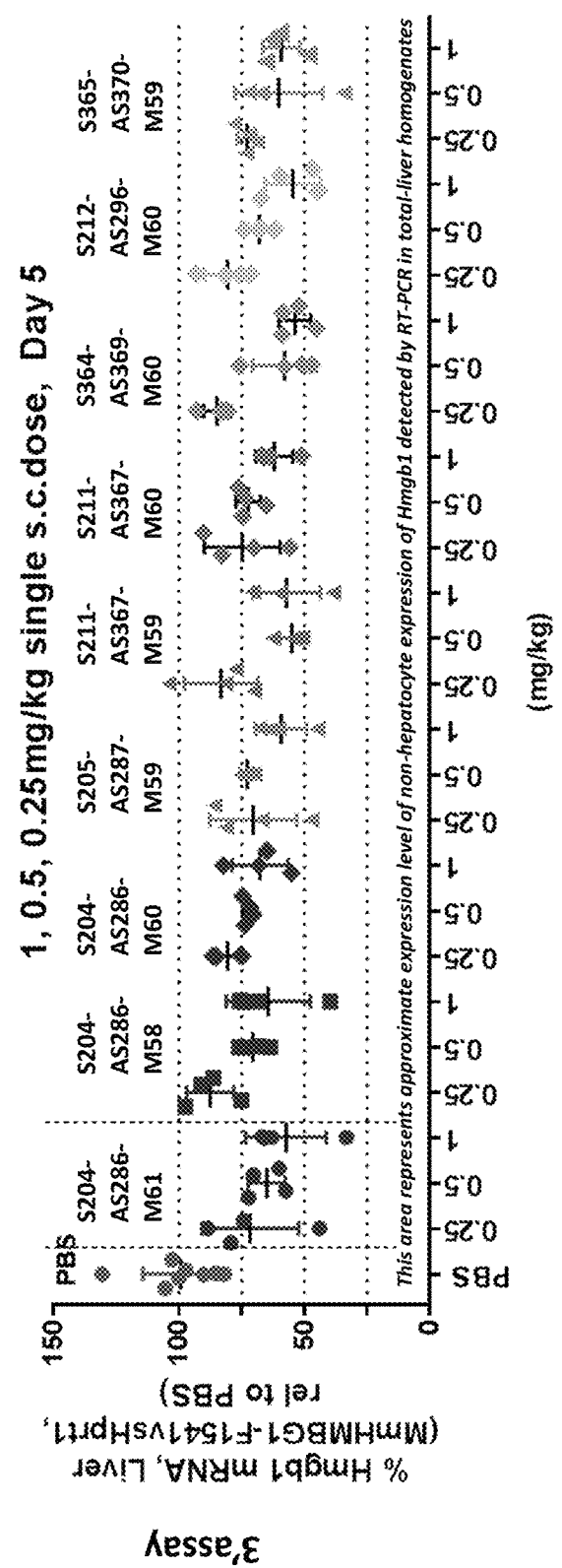

A confirmatory dose-response assay was also performed on six GalNAc-conjugated HMGB1 oligonucleotides (S204-AS286, S205-AS287, S211-AS367, S364-AS369, S212-AS296, and S365-AS370) with different modification patterns (M58, M59, or M60). A single dose (1, 0.5, or 0.25 mg/kg) of indicated GalNAc-conjugated HMGB1 oligonucleotides were administered to CD-1 mice subcutaneously. The mice were euthanized on day 5 after administration and liver samples were obtained. RNA was extracted to evaluate HMGB1 mRNA levels by qPCR (normalized to HPRT1-F576, a housekeeping gene). The levels of remaining HMGB1 mRNA were interrogated using TAQMAN®-based qPCR assays. PBS was used as negative control, and S204-AS286-M61 was used as positive control in this experiment. Almost all tested HMGB1 oligonucleotide inhibitors demonstrated dose-dependent potency (FIGS. 29A and 29B). Some of the tested HMGB1 oligonucleotide inhibitors showed improved potency compared to the S204-AS286-M61 control (FIGS. 29A and 29B). The confirmatory dose-response assay was repeated for S204-AS286-M59, S211-AS367-M59, S364-AS369-M60, and S365-AS370-M59. Similar results were obtained and all tested HMGB1 oligonucleotide inhibitors showed an $ED_{50}$ of about 0.5 to 1.0 mg/kg, if HMGB1 expression level in non-hepatocytes is considered the expression baseline (FIGS. 31A and 31B).

Figure 30C:
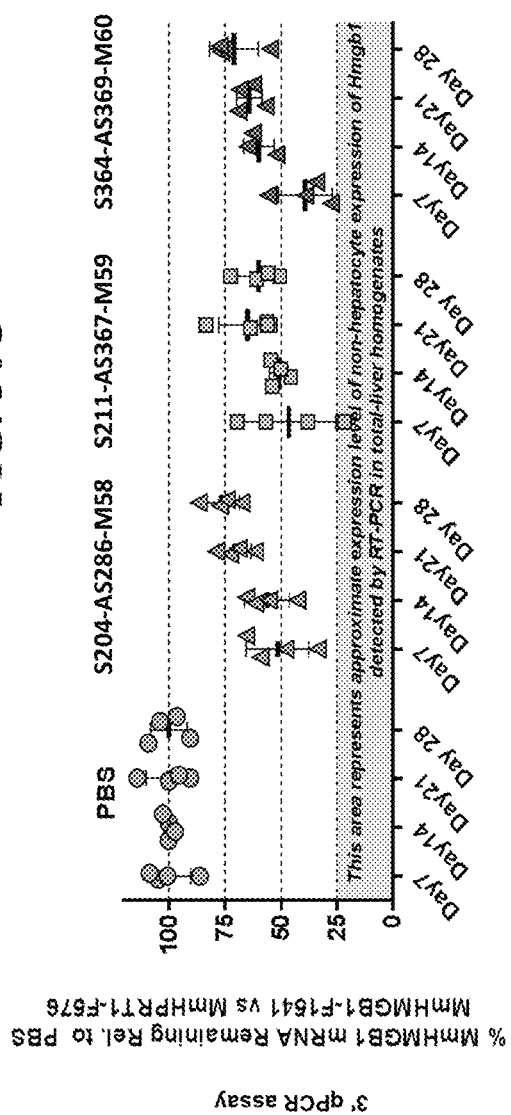
Figure 30D:
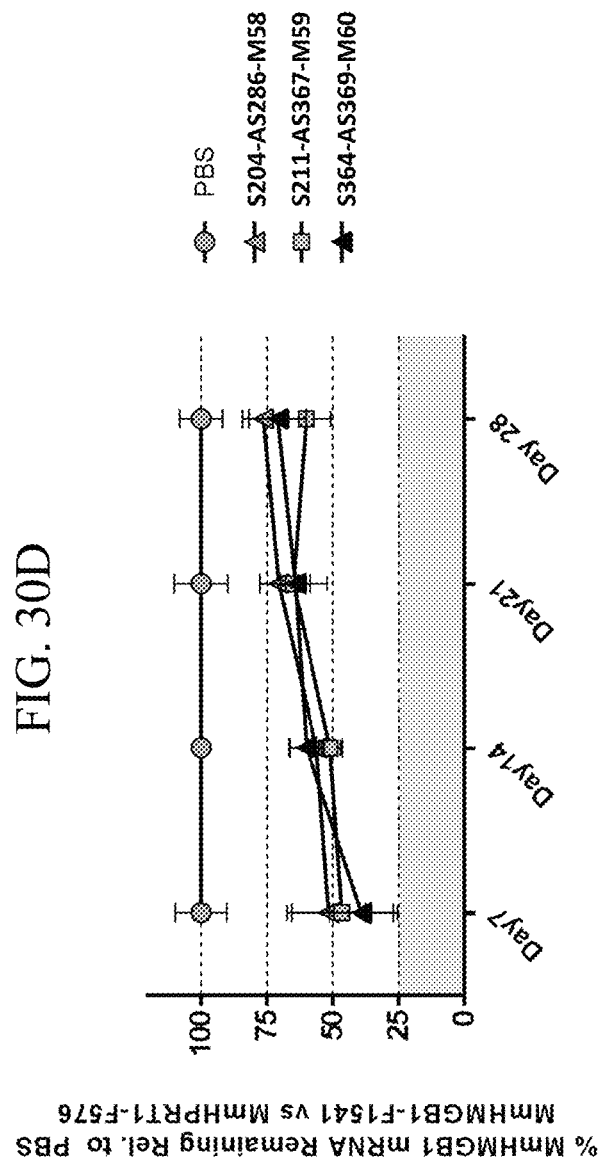

Two GalNAc-conjugated HMGB1 oligonucleotides (S211-AS367-M59, S364-AS369-M60) with different modification patterns (denoted as M59 and M60, respectively) were tested in vivo in a duration study to evaluate their activity in inhibiting HMGB1 expression in mice. PBS was used as negative control, and S204-AS286-M58 was used as positive control in this experiment. Mice were injected subcutaneously with a single dose (1 mg/kg) of indicated GalNAc-conjugated HMGB1 oligonucleotides. Mice were euthanized on days 7, 14, 21, and 28 post injection and liver samples were obtained. RNA was extracted to evaluate HMGB1 mRNA levels by qPCR (normalized to HPRT1-F576, a housekeeping gene). The qPCR was performed using two different primers specific to different regions in the HMGB1 mRNA. The qPCR performed using the primer at the 5' end relative to the other primer was designated "5' qPCR." Similarly, the qPCR performed using the primer at the 3' end relative to the other primer was designated "3' qPCR." The data showed that all tested HMGB1 oligonucleotides were potent in knockdown HMGB1 3 weeks after injection, as indicated by the reduced amount of HMGB1 mRNA remaining in mice liver at days 7, 14, 21, and 28 (normalized to a PBS control treatment) (FIGS. 30A and 30B).

Figure 31A:
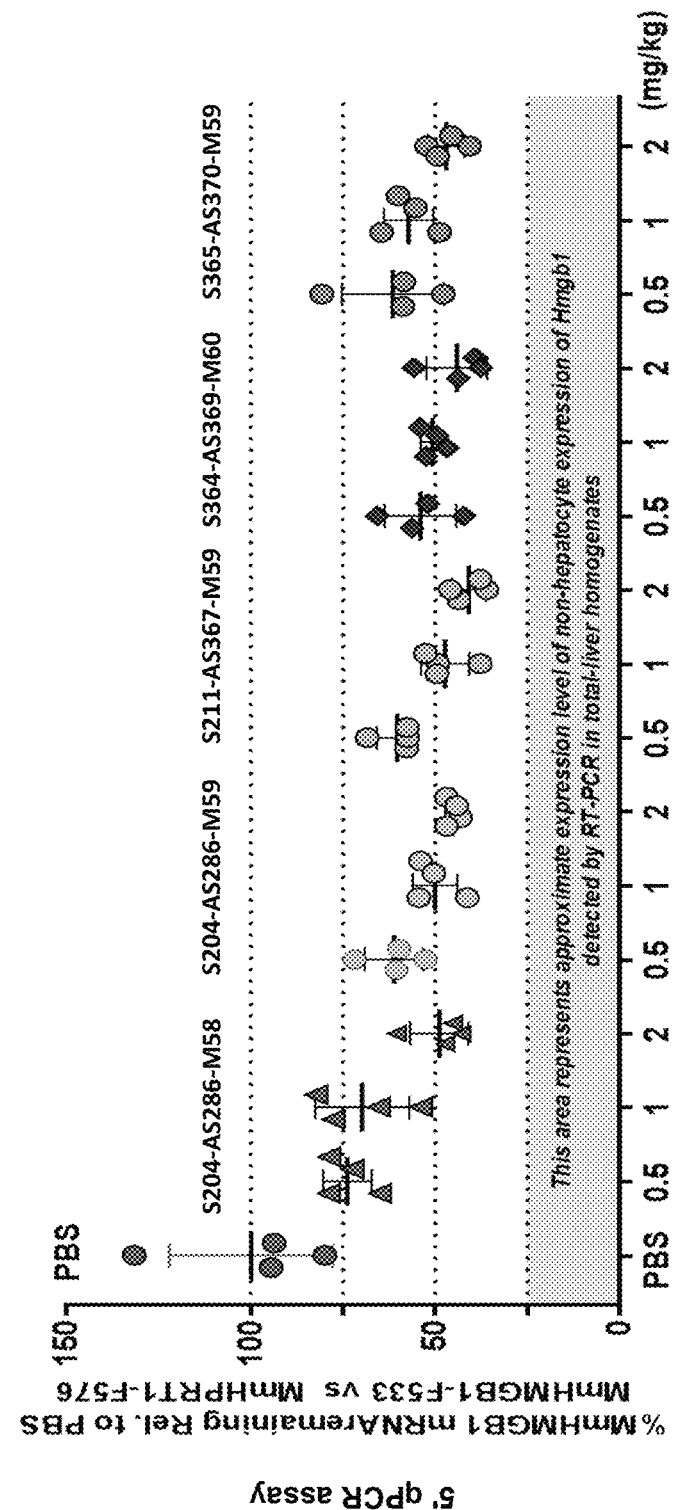
FIGS. 31A-31B are graphs showing an in vivo activity evaluation of four GalNAc-conjugated HMGB1 oligonucleotides at three different dosages (1, 0.5, or 0.25 mg/kg). The percentage of remaining HMGB1 mRNA in the liver 5 days after administration of the oligonucleotides, normalized to the remaining HMGB1 mRNA levels in mice treated with PBS, was evaluated in either a 5' qPCR reaction (FIG. 31 A) or a 3' qPCR reaction (FIG. 31B). All tested HMGB1 oligonucleotide inhibitors showed an $ED_{50}$ (effective dose for 50% of recipient receiving the drug) of about 0.5 to 1.0 mg/kg.
Figure 31B:
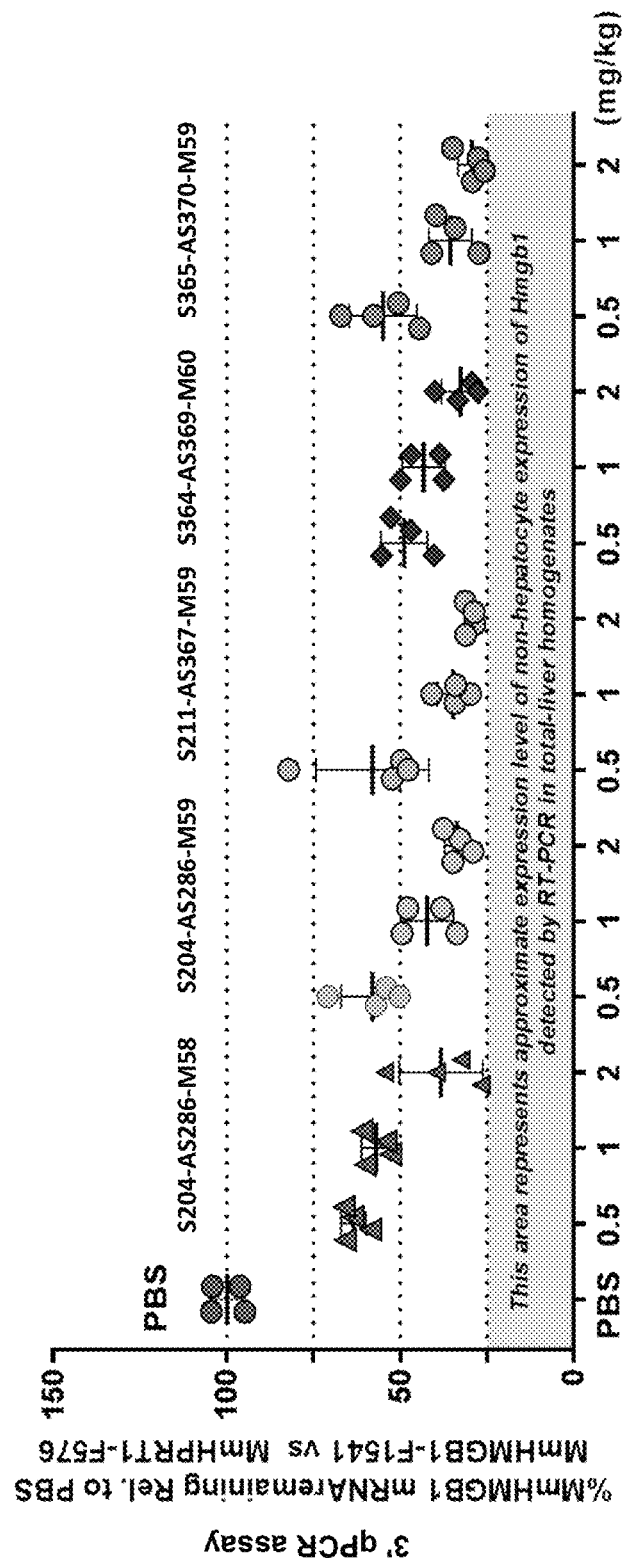
Figure 32A:
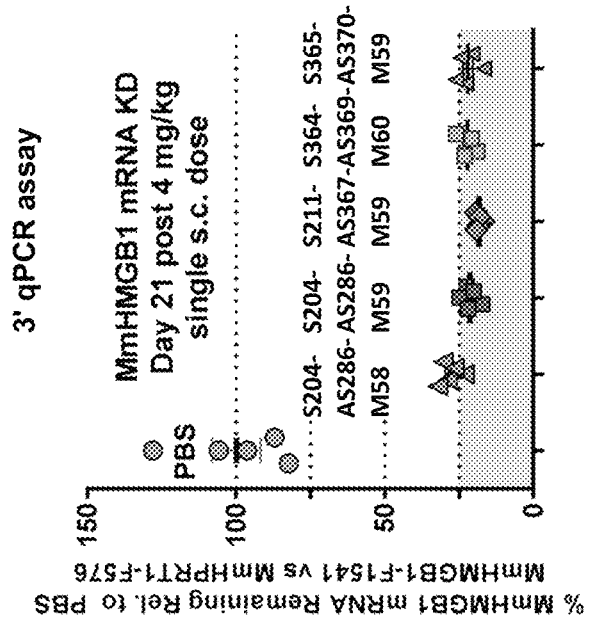
FIGS. 32A-32B are graphs showing an in vivo activity evaluation of four GalNAc-conjugated HMGB1 oligonucleotides 21 days after subcutaneous administration. The per cent percentage of remaining HMGB1 mRNA in the liver 21 days after administration of the oligonucleotides, normalized to the remaining HMGB1 mRNA levels in mice treated with PBS, was evaluated in either a 5' qPCR reaction (FIG. 32 A) or a 3' qPCR reaction (FIG. 32B). The results showed that all tested GalNAc-conjugated HMGB1 oligonucleotides retained potency in knockdown HMGB1 3 weeks post injection.
Figure 32B:
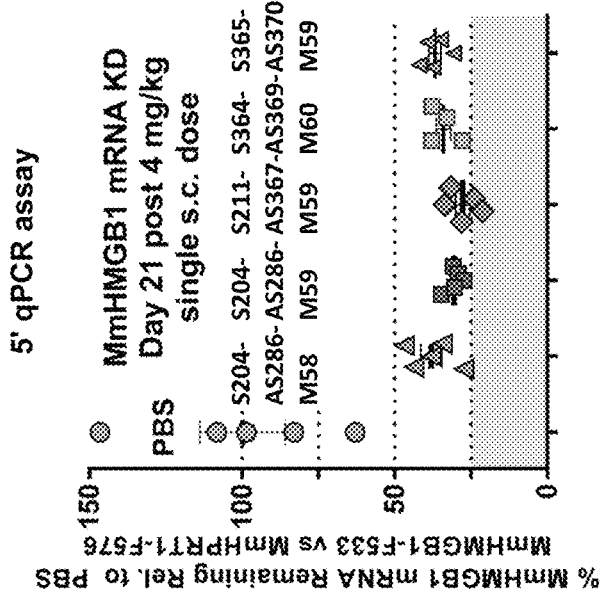

All HMGB1 oligonucleotide inhibitors tested in FIGS. 31A and 31B (S204-AS286-M59, S211-AS367-M59, S364-AS369-M60, and S365-AS370-M59) were selected to be further tested in a 3-week duration study. In this study, a single dose (4 mg/kg) of the indicated HMGB1 oligonucleotide inhibitors were injected subcutaneously to CD-1 mice. Mice were euthanized 21 days post injection and liver samples were obtained. RNA was extracted to evaluate HMGB1 mRNA levels by qPCR (normalized to HPRT1-F576 housekeeping gene). The levels of remaining HMGB1 mRNA were interrogated using TAQMAN®-based qPCR assays. The results showed that all tested HMGB1 oligonucleotide inhibitors retained potency in knocking down HMGB1 3 weeks post injection (FIGS. 32A and 32B).

Figure 33G:
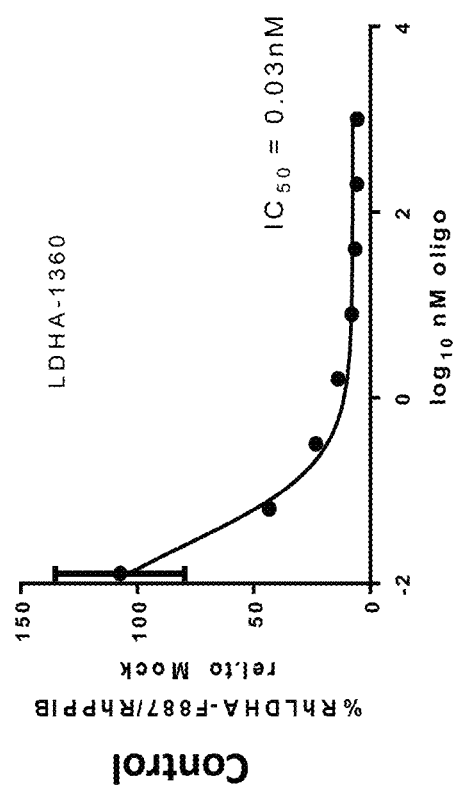
Figure 34A:
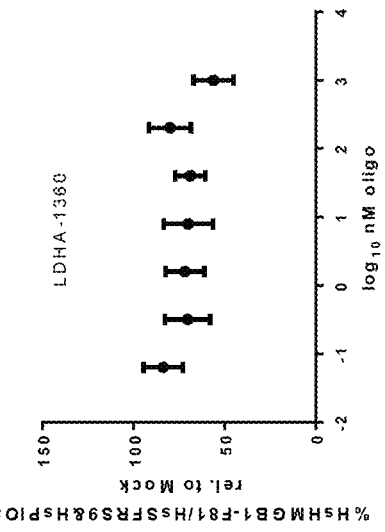
FIGS. 34A-34G are IC50 curves demonstrating uptake and activity of the 2 GalNAc-conjugates HMGB1 oligonucleotides in primary human hepatocytes. The IC50 curves were normalized to mock treatment. Results for hsHMGB1 5' qPCR reactions are shown in FIGS. 34A-34C), and results for 3' qPCR reactions are shown in FIGS. 34D-34F. A GalNAc-conjugate LDHA oligonucleotide was used as assay control (FIGS. 34C, 34F, and 34G). The level of remaining HsLDHA mRNA was measured by a LDHA specific primer in qPCR assay (FIG. 34G).
Figure 34B:
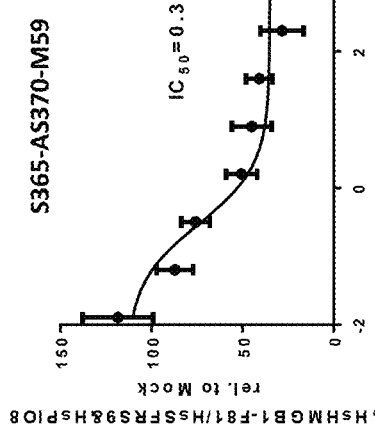
Figure 34C:
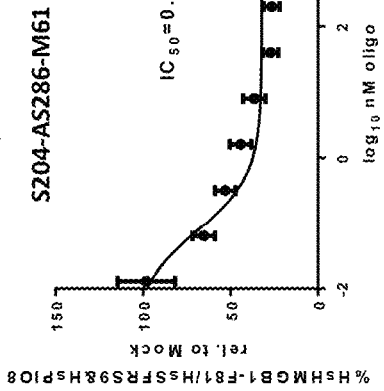
Figure 34D:
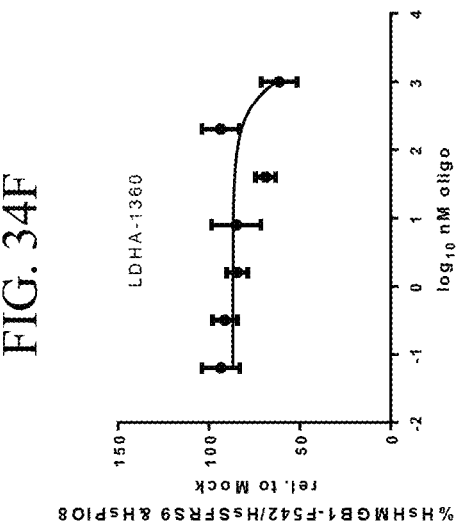
Figure 34E:
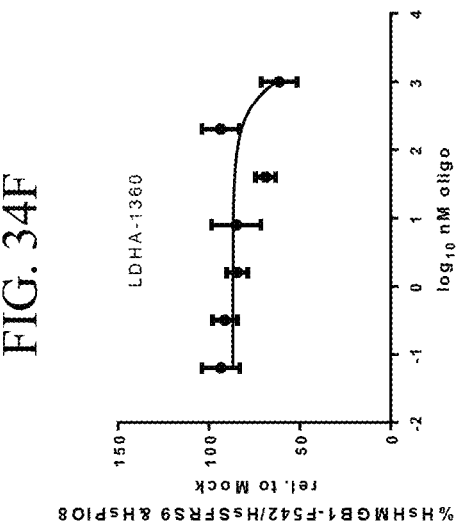
Figure 34F:
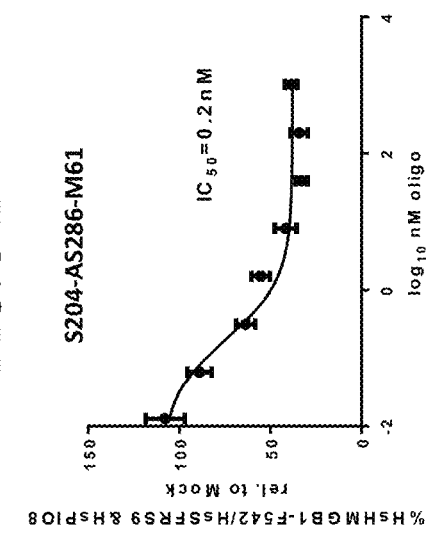
Figure 34G:
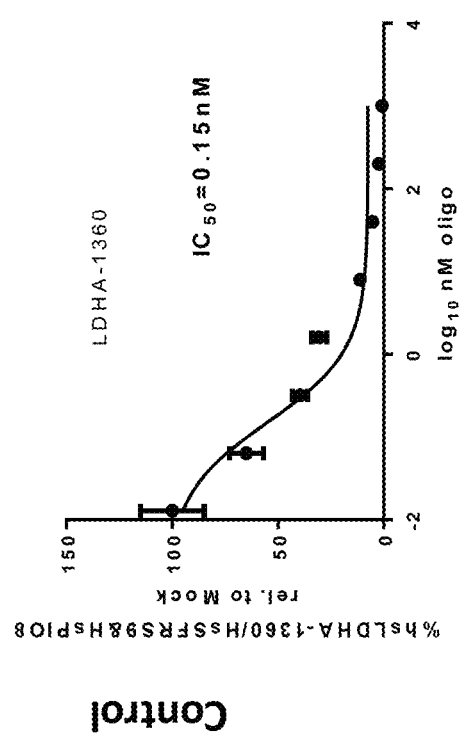

Certain GalNAc-conjugated HMGB1 oligonucleotides were further tested using a full dose response curve in rhesus monkey or human hepatocytes in order to determine the half maximal inhibitory concentration ($IC_{50}$) for each inhibitor. Human primary hepatocytes (HPCH10+, Lot #1410214, Cryopreserved Xenotech) or monkey primary hepatocyte (P2000.H15, Lot #1410285, Cryopreserved Xenotech) were thawed and plated at 50000 cells (human) or 100000 (monkey) per well in 96-well tissue culture plates in OptiPlate Hepatocyte Media (K8200). Plated hepatocytes were allowed to recover for 1-6 h at 37° C. and 5% CO2 and subsequently maintained using OptiCulture Hepatocyte Media (K8300). Five-fold serially diluted (7-times) GalNAc-conjugated HMGB1 oligonucleotides (S204-AS286-M61 and S365-AS370-M59) were added to cells. The uptake of the oligonucleotides into the monkey or human primary hepatocyte cells was mediated by ASGPR receptor. Cells were incubated for 48 h at 37° C. and 5% CO2. RNA was extracted from cells using SV 96 Total RNA Isolation System (Promega) to evaluate remaining HMGB1 mRNA levels by qPCR (normalized to RhPPIB or HsSFRS9 and HsPIO8, housekeeping genes). The levels of remaining HMGB1 mRNA were interrogated using TAQMAN®-based qPCR assays. A GalNAc-conjugate LDHA oligonucleotide was used as assay control (FIGS. 33C, 33F, 33G, 34C, 34F, 34G) and the level of remaining LDHA mRNA was measured by RhLDHA-F887 qPCR assay (FIGS. 33G and 34G).

The results showed that the HMGB1 oligonucleotide inhibitors were potent (sub-nM $IC_{50}$ values) in knocking down HMGB1 in primary mice hepatocytes, as demonstrated by the sub-nM to nM $IC_{50}$ values (FIGS. 33A, 33B, 33D, and 33E). Similar knock down potency was observed in in primary human hepatocytes, as demonstrated by sub-nM $IC_{50}$ values (FIGS. 34A, 34B, 34D, and 34E).

Materials and Methods
Transfection

For the first screen, Lipofectamine RNAiMAX™ was used to complex the oligonucleotides for efficient transfection. Oligonucleotides, RNAiMAX and Opti-MEM were added to a plate and incubated at room temperature for 20 minutes prior to transfection. Media was aspirated from a flask of actively passaging cells and the cells are incubated at 37° C. in the presence of trypsin for 3-5 minutes. After cells no longer adhered to the flask, cell growth media (lacking penicillin and streptomycin) was added to neutralize the trypsin and to suspend the cells. A 10 μL aliquot was removed and counted with a hemocytometer to quantify the cells on a per millimeter basis. For HeLa cells, 20,000 cells were seeded per well in 100 μL of media. The suspension was diluted with the known cell concentration to obtain the total volume required for the number of cells to be transfected. The diluted cell suspension was added to the 96 well transfection plates, which already contained the oligonucleotides in Opti-MEM. The transfection plates were then incubated for 24 hours at 37° C. After 24 hours of incubation, media was aspirated from each well. Cells were lysed using the lysis buffer from the Promega RNA Isolation kit. The lysis buffer was added to each well. The lysed cells were then transferred to the Corbett XtractorGENE (QIAxtractor) for RNA isolation or stored at −80° C.

For subsequent screens and experiments, e.g., the secondary screen, Lipofectamine RNAiMAx was used to complex the oligonucleotides for reverse transfection. The complexes were made by mixing RNAiMAX and siRNAs in OptiMEM medium for 15 minutes. The transfection mixture was transferred to multi-well plates and cell suspension was added to the wells. After 24 hours incubation the cells were washed once with PBS and then lysed using lysis buffer from the Promega SV96 kit. The RNA was purified using the SV96 plates in a vacuum manifold. Four microliters of the purified RNA was then heated at 65° C. for 5 minutes and cooled to 4° C. The RNA was then used for reverse transcription using the High Capacity Reverse Transcription kit (Life Technologies) in a 10 microliter reaction. The cDNA was then diluted to 50 μl with nuclease free water and used for quantitative PCR with multiplexed 5′-endonuclease assays and SSoFast qPCR mastermix (Bio-Rad laboratories).

cDNA Synthesis

RNA was isolated from mammalian cells in tissue culture using the Corbett X-tractor Gene™ (QIAxtractor). A modified SuperScript II protocol was used to synthesize cDNA from the isolated RNA. Isolated RNA (approximately 5 ng/μL) was heated to 65° C. for five minutes and incubated with dNPs, random hexamers, oligo dTs, and water. The mixture was cooled for 15 seconds. An "enzyme mix," consisting of water, 5× first strand buffer, DTT, SUPERase•In™ (an RNA inhibitor), and SuperScript II RTase was added to the mixture. The contents were heated to 42° C. for one hour, then to 70° C. for 15 minutes, and then cooled to 4° C. using a thermocycler. The resulting cDNA was then subjected to SYBR®-based qPCR. The qPCR reactions were multiplexed, containing two 5′ endonuclease assays per reaction.

qPCR Assays

Primer sets were initially screened using SYBR®-based qPCR. Assay specificity was verified by assessing melt curves as well as "minus RT" controls. Dilutions of cDNA template (10-fold serial dilutions from 20 ng and to 0.02 ng per reaction) from HeLa and Hepa1-6 cells are used to test human (Hs) and mouse (Mm) assays, respectively. qPCR assays were set up in 384-well plates, covered with MicroAmp film, and run on the 7900HT from Applied Biosystems. Reagent concentrations and cycling conditions included the following: 2×SYBR mix, 10 μM forward primer, 10 μM reverse primer, DD H$_2$O, and cDNA template up to a total volume of 10 μL.

In some cases, as noted, qPCR was performed using TAQMAN®-based qPCR assays. TAQMAN® probes target two different positions (5′ and 3′ to one another) within the coding region of the target mRNA (e.g., HMGB1) were generally used to provide additional confirmation of mRNA levels in the analysis.

Cloning

PCR amplicons that displayed a single melt-curve were ligated into the pGEM®-T Easy vector kit from Promega according to the manufacturer's instructions. Following the manufacturer's protocol, JM109 High Efficiency cells were transformed with the newly ligated vectors. The cells were then plated on LB plates containing ampicillin and incubated at 37° C. overnight for colony growth.

PCR Screening and Plasmid Mini-Prep

PCR was used to identify colonies of E. coli that had been transformed with a vector containing the ligated amplicon of interest. Vector-specific primers that flank the insert were used in the PCR reaction. All PCR products were then run on a 1% agarose gel and imaged by a transilluminator following staining. Gels were assessed qualitatively to determine which plasmids appeared to contain a ligated amplicon of the expected size (approximately 300 bp, including the amplicon and the flanking vector sequences specific to the primers used).

The colonies that were confirmed transformants by PCR screening were then incubated overnight in cultures consisting of 2 mL LB broth with ampicillin at 37° C. with shaking. E. coli cells were then lysed, and the plasmids of interest were isolated using Promega's Mini-Prep kit. Plasmid concentration was determined by UV absorbance at 260 nm.

Plasmid Sequencing and Quantification

Purified plasmids were sequenced using the BigDye® Terminator sequencing kit. The vector-specific primer, T7, was used to give read lengths that span the insert. The following reagents were used in the sequencing reactions: water, 5× sequencing buffer, BigDye terminator mix, T7 primer, and plasmid (100 ng/μL) to a volume of 10 μL. The mixture was held at 96° C. for one minute, then subjected to 15 cycles of 96° C. for 10 seconds, 50° C. for 5 seconds, 60° C. for 1 minute, 15 seconds; 5 cycles of 96° C. for 10 seconds, 50° C. for 5 seconds, 60° C. for 1 minute, 30 seconds; and 5 cycles of 96° C. for 10 seconds, 50° C. for 5 seconds, and 60° C. for 2 minutes. Dye termination reactions were then sequenced using Applied Biosystems' capillary electrophoresis sequencers.

Sequence-verified plasmids were then quantified. They were linearized using a single cutting restriction endonuclease. Linearity was confirmed using agarose gel electrophoresis. All plasmid dilutions were made in TE buffer (pH 7.5) with 100 μg of tRNA per mL buffer to reduce nonspecific binding of plasmid to the polypropylene vials.

The linearized plasmids were then serially diluted from 1,000,000 to 01 copies per μL and subjected to qPCR. Assay efficiency was calculated and the assays were deemed acceptable if the efficiency was in the range of 90-110%.

Multi-Plexing Assays

For each target, mRNA levels were quantified by two 5′ nuclease assays. In general, several assays are screened for each target. The two assays selected displayed a combination of good efficiency, low limit of detection, and broad 5′43′ coverage of the gene of interest (GOI). Both assays against one GOI could be combined in one reaction when different fluorophores were used on the respective probes. Thus, the final step in assay validation was to determine the efficiency of the selected assays when they were combined in the same qPCR or "multi-plexed".

Linearized plasmids for both assays in 10-fold dilutions were combined and qPCR was performed. The efficiency of each assay was determined as described above. The accepted efficiency rate was 90-110%.

While validating multi-plexed reactions using linearized plasmid standards, $C_q$ values for the target of interest were also assessed using cDNA as the template. For human or mouse targets, HeLa and Hepa1-6 cDNA were used, respectively. The cDNA, in this case, was derived from RNA isolated on the Corbett (~5 ng/μl in water) from untransfected cells. In this way, the observed $C_q$ values from this sample cDNA were representative of the expected $C_q$ values from a 96-well plate transfection. In cases where $C_q$ values were greater than 30, other cell lines were sought that exhibit higher expression levels of the gene of interest. A library of total RNA isolated from via high-throughput methods on the Corbett from each human and mouse line was generated and used to screen for acceptable levels of target expression.

Description of Oligonucleotide Nomenclature

All oligonucleotides described herein are designated either $SN_1$-$ASN_2$-$MN_3$. The following designations apply:
- $N_1$: sequence identifier number of the sense strand sequence
- $N_2$: sequence identifier number of the antisense strand sequence
- $N_3$: reference number of modification pattern, in which each number represents a pattern of modified nucleotides in the oligonucleotide.

For example, S27-AS123-M15 represents an oligonucleotide with a sense sequence that is set forth by SEQ ID NO: 27, an antisense sequence that is set forth by SEQ ID NO: 123, and which is adapted to modification pattern number 15.

TABLE 7

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S1-AS97 | AGAUUUGUUUUUAAACUGUACAGTG | 1 | CACUGUACAGUUUAAAAACAAAUCUUA | 97 |
| S2-AS98 | GUACAGUGUCUUUUUUGUAUAGTT | 2 | AACUAUACAAAAAAGACACUGUACAG | 98 |
| S3-AS99 | ACAGUGUCUUUUUUGUAUAGUUAA | 3 | UUAACUAUACAAAAAAGACACUGUAC | 99 |
| S4-AS100 | AGUGUCUUUUUUGUAUAGUUAACA | 4 | UGUUAACUAUACAAAAAAGACACUGU | 100 |
| S5-AS101 | GUGUCUUUUUUGUAUAGUUAACAC | 5 | GUGUUAACUAUACAAAAAAGACACUG | 101 |
| S6-AS102 | GGUGGUAUUUUCAAUAGCCACUAAC | 6 | GUUAGUGGCUAUUGAAAAUACCACCAG | 102 |
| S7-AS103 | GUAUUUUCAAUAGCCACUAACCUTG | 7 | CAAGGUUAGUGGCUAUUGAAAAUACCA | 103 |
| S8-AS104 | GUGCACAGCACAAAUUAGUUAUATA | 8 | UAUAUAACUAAUUUGUGCUGUGCACCA | 104 |
| S9-AS105 | GUUGUCUCUGAUGCAGCUAUACGA | 9 | UCGUAUAAGCUGCAUCAGAGACAACUG | 105 |
| S10-AS106 | UCUGAUGCAGCUUAUACGAAAUAAT | 10 | AUUAUUUCGUAUAAGCUGCAUCAGAGA | 106 |
| S11-AS107 | CUGAUGCAGCUUAUACGAAAUAATT | 11 | AAUUAUUUCGUAUAAGCUGCAUCAGAG | 107 |
| S12-AS108 | GAUGCAGCUUAUACGAAAUAAUUGT | 12 | ACAAUUAUUUCGUAUAAGCUGCAUCAG | 108 |
| S13-AS109 | AUGCAGCUUAUACGAAAUAAUUGTT | 13 | AACAAUUAUUUCGUAUAAGCUGCAUCA | 109 |
| S14-AS110 | GCAGCUUAUACGAAAUAAUUGUUGT | 14 | ACAACAAUUAUUUCGUAUAAGCUGCAU | 110 |
| S15-AS111 | CAGCUUAUACGAAAUAAUUGUUGTT | 15 | AACAACAAUUAUUUCGUAUAAGCUGCA | 111 |
| S16-AS112 | AGCUUAUACGAAAUAAUUGUUGUTC | 16 | GAACAACAAUUAUUUCGUAUAAGCUGC | 112 |
| S17-AS113 | GCUUAUACGAAAUAAUUGUUGUUCT | 17 | AGAACAACAAUUAUUUCGUAUAAGCUG | 113 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S18-AS114 | UACGAAAUAAUUGUUGUUCUGUUAA | 18 | UUAACAGAACAACAAUUAUUUCGUAUA | 114 |
| S19-AS115 | ACGAAAUAAUUGUUGUUCUGUUAAC | 19 | GUUAACAGAACAACAAUUAUUUCGUAU | 115 |
| S20-AS116 | CGAAAUAAUUGUUGUUCUGUUAACT | 20 | AGUUAACAGAACAACAAUUAUUUCGUA | 116 |
| S21-AS117 | GAAAUAAUUGUUGUUCUGUUAACTG | 21 | CAGUUAACAGAACAACAAUUAUUUCGU | 117 |
| S22-AS118 | AAAUAAUUGUUGUUCUGUUAACUGA | 22 | UCAGUUAACAGAACAACAAUUAUUUCG | 118 |
| S23-AS119 | AAUAAUUGUUGUUCUGUUAACUGAA | 23 | UUCAGUUAACAGAACAACAAUUAUUUC | 119 |
| S24-AS120 | AUAAUUGUUGUUCUGUUAACUGAAT | 24 | AUUCAGUUAACAGAACAACAAUUAUUU | 120 |
| S25-AS121 | UAAUUGUUGUUCUGUUAACUGAATA | 25 | UAUUCAGUUAACAGAACAACAAUUAUU | 121 |
| S26-AS122 | AAUUGUUGUUCUGUUAACUGAAUAC | 26 | GUAUUCAGUUAACAGAACAACAAUUAU | 122 |
| S27-AS123 | AUUGUUGUUCUGUUAACUGAAUACC | 27 | GGUAUUCAGUUAACAGAACAACAAUUA | 123 |
| S28-AS124 | UUGUUGUUCUGUUAACUGAAUACCA | 28 | UGGUAUUCAGUUAACAGAACAACAAUU | 124 |
| S29-AS125 | UGUUGUUCUGUUAACUGAAUACCAC | 29 | GUGGUAUUCAGUUAACAGAACAACAAU | 125 |
| S30-AS126 | GUUGUUCUGUUAACUGAAUACCACT | 30 | AGUGGUAUUCAGUUAACAGAACAACAA | 126 |
| S31-AS127 | UUGUUCUGUUAACUGAAUACCACTC | 31 | GAGUGGUAUUCAGUUAACAGAACAACA | 127 |
| S32-AS128 | GUUCUGUUAACUGAAUACCACUCTG | 32 | CAGAGUGGUAUUCAGUUAACAGAACAA | 128 |
| S33-AS129 | UGUUAACUGAAUACCACUCUGUAAT | 33 | AUUACAGAGUGGUAUUCAGUUAACAGA | 129 |
| S34-AS130 | GUUAACUGAAUACCACUCUGUAATT | 34 | AAUUACAGAGUGGUAUUCAGUUAACAG | 130 |
| S35-AS131 | UUAACUGAAUACCACUCUGUAAUTG | 35 | CAAUUACAGAGUGGUAUUCAGUUAACA | 131 |
| S36-AS132 | UAACUGAAUACCACUCUGUAAUUGC | 36 | GCAAUUACAGAGUGGUAUUCAGUUAAC | 132 |
| S37-AS133 | AACUGAAUACCACUCUGUAAUUGCA | 37 | UGCAAUUACAGAGUGGUAUUCAGUUAA | 133 |
| S38-AS134 | ACUGAAUACCACUCUGUAAUUGCAA | 38 | UUGCAAUUACAGAGUGGUAUUCAGUUA | 134 |
| S39-AS135 | CUGAAUACCACUCUGUAAUUGCAAA | 39 | UUUGCAAUUACAGAGUGGUAUUCAGUU | 135 |
| S40-AS136 | UGAAUACCACUCUGUAAUUGCAAAA | 40 | UUUUGCAAUUACAGAGUGGUAUUCAGU | 136 |
| S41-AS137 | GAAUACCACUCUGUAAUUGCAAAAA | 41 | UUUUUGCAAUUACAGAGUGGUAUUCAG | 137 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S42-AS138 | AAUACCACUCUGUAAUUGCAAAAAA | 42 | UUUUUUGCAAUUACAGAGUGGUAUUCA | 138 |
| S43-AS139 | AUACCACUCUGUAAUUGCAAAAAAA | 43 | UUUUUUUGCAAUUACAGAGUGGUAUUC | 139 |
| S44-AS140 | AUGCAGCUUAUACGAAGAUAAUUGT | 44 | ACAAUUAUCUUCGUAUAAGCUGCAUCA | 140 |
| S45-AS141 | UGCAGCUUAUACGAAGAUAAUUGTT | 45 | AACAAUUAUCUUCGUAUAAGCUGCAUC | 141 |
| S46-AS142 | GCAGCUUAUACGAAGAUAAUUGUTG | 46 | CAACAAUUAUCUUCGUAUAAGCUGCAU | 142 |
| S47-AS143 | CAGCUUAUACGAAGAUAAUUGUUGT | 47 | ACAACAAUUAUCUUCGUAUAAGCUGCA | 143 |
| S48-AS144 | GCUUAUACGAAGAUAAUUGUUGUTC | 48 | GAACAACAAUUAUCUUCGUAUAAGCUG | 144 |
| S49-AS145 | CUUAUACGAAGAUAAUUGUUGUUCT | 49 | AGAACAACAAUUAUCUUCGUAUAAGCU | 145 |
| S50-AS146 | AUACGAAGAUAAUUGUUGUUCUGTT | 50 | AACAGAACAACAAUUAUCUUCGUAUAA | 146 |
| S51-AS147 | ACGAAGAUAAUUGUUGUUCUGUUAA | 51 | UUAACAGAACAACAAUUAUCUUCGUAU | 147 |
| S52-AS148 | CGAAGAUAAUUGUUGUUCUGUUAAC | 52 | GUUAACAGAACAACAAUUAUCUUCGUA | 148 |
| S53-AS149 | GCAGCUGUUUUGUUGACAUUCUGAA | 53 | UUCAGAAUGUCAACAAAACAGCUGCAA | 149 |
| S54-AS150 | GCUGUUUUGUUGACAUUCUGAAUGC | 54 | GCAUUCAGAAUGUCAACAAAACAGCUG | 150 |
| S55-AS151 | CUGUUUUGUUGACAUUCUGAAUGCT | 55 | AGCAUUCAGAAUGUCAACAAAACAGCU | 151 |
| S56-AS152 | GUUUUGUUGACAUUCUGAAUGCUC | 56 | GAAGCAUUCAGAAUGUCAACAAAACAG | 152 |
| S57-AS153 | GUUGACAUUCUGAAUGCUUCUAAGT | 57 | ACUUAGAAGCAUUCAGAAUGUCAACAA | 153 |
| S58-AS154 | GACAUUCUGAAUGCUUCUAAGUAAA | 58 | UUUACUUAGAAGCAUUCAGAAUGUCAA | 154 |
| S59-AS155 | ACAUUCUGAAUGCUUCUAAGUAAAT | 59 | AUUUACUUAGAAGCAUUCAGAAUGUCA | 155 |
| S60-AS156 | AUUCUGAAUGCUUCUAAGUAAAUAC | 60 | GUAUUUACUUAGAAGCAUUCAGAAUGU | 156 |
| S61-AS157 | UUCUGAAUGCUUCUAAGUAAAUACA | 61 | UGUAUUUACUUAGAAGCAUUCAGAAUG | 157 |
| S62-AS158 | UCUGAAUGCUUCUAAGUAAAUACAA | 62 | UUGUAUUUACUUAGAAGCAUUCAGAAU | 158 |
| S63-AS159 | CUGAAUGCUUCUAAGUAAAUACAAT | 63 | AUUGUAUUUACUUAGAAGCAUUCAGAA | 159 |
| S64-AS160 | UGAAUGCUUCUAAGUAAAUACAATT | 64 | AAUUGUAUUUACUUAGAAGCAUUCAGA | 160 |
| S65-AS161 | GAAUGCUUCUAAGUAAAUACAAUTT | 65 | AAAUUGUAUUUACUUAGAAGCAUUCAG | 161 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
| --- | --- | --- | --- | --- |
| S66-AS162 | AAUGCUUCUAAGUAAAUA CAAUUTT | 66 | AAAAUUGUAUUUA CUUAGAAGCAUUCA | 162 |
| S67-AS163 | AUGCUUCUAAGUAAAUAC AAUUUTT | 67 | AAAAAUUGUAUUU ACUUAGAAGCAUUC | 163 |
| S68-AS164 | UGCUUCUAAGUAAAUACA AUUUUTT | 68 | AAAAAAUUGUAUU UACUUAGAAGCAUU | 164 |
| S69-AS165 | GUUGUCCUUUUCAUAGGU CUGAAAT | 69 | AUUUCAGACCUAUG AAAAGGACAACAA | 165 |
| S70-AS166 | UGAGAUAGUUUUCAUCCA UAACUGA | 70 | UCAGUUAUGGAUG AAAACUAUCUCAAC | 166 |
| S71-AS167 | GAGAUAGUUUUCAUCCAU AACUGAA | 71 | UUCAGUUAUGGAU GAAAACUAUCUCAA | 167 |
| S72-AS168 | ACAUUUUCAUCCAUAGUU GAAGAAT | 72 | AUUCUUCAACUAUG GAUGAAAAUGUUA | 168 |
| S73-AS169 | CAUUUACAAACUGAAGAG UAAUCAA | 73 | UUGAUUACUCUUCA GUUUGUAAAUGUA | 169 |
| S74-AS170 | AUUUACAAACUGAAGAGU AAUCAAT | 74 | AUUGAUUACUCUUC AGUUUGUAAAUGU | 170 |
| S75-AS171 | ACAAACUGAAGAGUAAUC AAUCUAC | 75 | GUAGAUUGAUUAC UCUUCAGUUUGUAA | 171 |
| S76-AS172 | GUAAUGACAGUUAUAUUU UGCAGTT | 76 | AACUGCAAAAUAUA ACUGUCAUUACAC | 172 |
| S77-AS173 | AAUGACAGUUAUAUUUUG CAGUUTC | 77 | GAAACUGCAAAAUA UAACUGUCAUUAC | 173 |
| S78-AS174 | AAUACAAGACUGCUGUAC UAUUUGT | 78 | ACAAAUAGUACAGC AGUCUUGUAUUUU | 174 |
| S79-AS175 | AUACAAGACUGCUGUACU AUUUGTT | 79 | AACAAAUAGUACAG CAGUCUUGUAUUU | 175 |
| S80-AS176 | UACAAGACUGCUGUACUA UUUGUTG | 80 | CAACAAAUAGUACA GCAGUCUUGUAUU | 176 |
| S81-AS177 | ACAAGACUGCUGUACUAU UUGUUGA | 81 | UCAACAAAUAGUAC AGCAGUCUUGUAU | 177 |
| S82-AS178 | CAAGACUGCUGUACUAUU UGUUGAC | 82 | GUCAACAAAUAGUA CAGCAGUCUUGUA | 178 |
| S83-AS179 | GACUGCUGUACUAUUUGU UGACCTT | 83 | AAGGUCAACAAAUA GUACAGCAGUCUU | 179 |
| S84-AS180 | ACUGCUGUACUAUUUGUU GACCUTA | 84 | UAAGGUCAACAAAU AGUACAGCAGUCU | 180 |
| S85-AS181 | GUGGUUUGUCCCUUUAUG AAUCAGA | 85 | UCUGAUUCAUAAAG GGACAAACCACAG | 181 |
| S86-AS182 | CAAUACAUUUGCUUUUUC UUUAUAA | 86 | UUAUAAAGAAAAA GCAAAUGUAUUGG A | 182 |
| S87-AS183 | AUACAUUUGCUUUUUCUU UAUAAAA | 87 | UUUUAUAAAGAAA AAGCAAAUGUAUU G | 183 |
| S88-AS184 | UGAUGGAGUGCUGUUAUA UAAUUTT | 88 | AAAAUUAUAUAAC AGCACUCCAUCACA | 184 |
| S89-AS185 | GAUGGAGUGCUGUUUUGU UAUAUAA | 89 | UUAUAUAACAAAAC AGCACUCCAUCAC | 185 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S90-AS186 | AUGGAGUGCUGUUUUGUU AUAUAAT | 90 | AUUAUAUAACAAA ACAGCACUCCAUCA | 186 |
| S91-AS187 | GGAGUGCUGUUUUGUUAU AUAAUTT | 91 | AAAUUAUAUAACA AAACAGCACUCCAU | 187 |
| S92-AS188 | GAGUGCUGUUUUGUUAUA UAAUUTA | 92 | UAAAUUAUAUAAC AAAACAGCACUCCA | 188 |
| S93-AS189 | CUGUUUUGUUAUAUAAUU UAGACTT | 93 | AAGUCUAAAUUAU AUAACAAAACAGCA | 189 |
| S94-AS190 | CAUUUGCGUUGUUAAUGU AAUUUGA | 94 | UCAAUUACAUUAA CAACGCAAAUGUA | 190 |
| S95-AS191 | AUGUAAUUUCAGGAGGAA UACUGAA | 95 | UUCAGUAUUCCUCC UGAAAUUACAUAA | 191 |
| S96-AS192 | GAGUCCUGGAUGAUACUA AUAAACT | 96 | AGUUUAUUAGUAU CAUCCAGGACUCAG | 192 |
| S193-AS273 | GUACAGUGUCUUUUUUG UAGCAGCCGAAAGGCUGC | 193 | UACAAAAAAAGACA CUGUACGG | 273 |
| S194-AS274 | ACAGUGUCUUUUUUGUA UAGCAGCCGAAAGGCUGC | 194 | UAUACAAAAAAAG ACACUGUGG | 274 |
| S195-AS275 | UCUGAUGCAGCUUAUACG AAGCAGCCGAAAGGCUGC | 195 | UUCGUAUAAGCUGC AUCAGAGA | 275 |
| S195-AS361 | UCUGAUGCAGCUUAUACG AAGCAGCCGAAAGGCUGC | 195 | UTCGUAUAAGCUGC AUCAGAGA | 361 |
| S196-AS276 | CUGAUGCAGCUUAUACGA AAGCAGCCGAAAGGCUGC | 196 | UUUCGUAUAAGCUG CAUCAGAG | 276 |
| S196-AS277 | CUGAUGCAGCUUAUACGA AAGCAGCCGAAAGGCUGC | 196 | UUUCGUAUAAGCUG CAUCAGGG | 277 |
| S196-AS278 | CUGAUGCAGCUUAUACGA AAGCAGCCGAAAGGCUGC | 196 | UUCGUAUAAGCUGC AUCAGGG | 278 |
| S196-AS362 | CUGAUGCAGCUUAUACGA AAGCAGCCGAAAGGCUGC | 196 | UTUCGUAUAAGCTG CATCAGAG | 362 |
| S197-AS279 | AUGCAGCUUAUACGAAAU AAGCAGCCGAAAGGCUGC | 197 | UUAUUUCGUAUAA GCUGCAUGG | 279 |
| S198-AS280 | GCAGCUUAUACGAAAUAA UAGCAGCCGAAAGGCUGC | 198 | UAUUAUUUCGUAU AAGCUGCGG | 280 |
| S199-AS281 | CAGCUUAUACGAAAUAAU UAGCAGCCGAAAGGCUGC | 199 | UAAUUAUUUCGUA UAAGCUGGG | 281 |
| S200-AS282 | GCUUAUACGAAAUAAUUG UAGCAGCCGAAAGGCUGC | 200 | UACAAUUAUUUCGU AUAAGCGG | 282 |
| S201-AS283 | AAAUAAUUGUUGUUCUGU UAGCAGCCGAAAGGCUGC | 201 | UAACAGAACAACAA UUAUUUGG | 283 |
| S202-AS284 | AAUAAUUGUUGUUCUGUU AAGCAGCCGAAAGGCUGC | 202 | UUAACAGAACAACA AUUAUUGG | 284 |
| S203-AS285 | AUUGUUGUUCUGUUAACU GAGCAGCCGAAAGGCUGC | 203 | UCAGUUAACAGAAC AACAAUGG | 285 |
| S204-AS286 | UUGUUGUUCUGUUAACUG AAGCAGCCGAAAGGCUGC | 204 | UUCAGUUAACAGAA CAACAAGG | 286 |
| S205-AS287 | UGUUGUUCUGUUAACUGA AAGCAGCCGAAAGGCUGC | 205 | UUUCAGUUAACAGA ACAACAGG | 287 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S206-AS288 | GUUGUUCUGUUAACUGAAUAGCAGCCGAAAGGCUGC | 206 | UAUUCAGUUAACAGAACAACGG | 288 |
| S207-AS289 | AACUGAAUACCACUCUGUAAGCAGCCGAAAGGCUGC | 207 | UUACAGAGUGGUAUUCAGUUGG | 289 |
| S208-AS290 | CUGAAUACCACUCUGUAAUAGCAGCCGAAAGGCUGC | 208 | UAUUACAGAGUGGUAUUCAGG | 290 |
| S209-AS291 | AAUACCACUCUGUAAUUGCAGCAGCCGAAAGGCUGC | 209 | UGCAAUUACAGAGUGGUAUUGG | 291 |
| S210-AS292 | AUUCUGAAUGCUUCUAAGUAGCAGCCGAAAGGCUGC | 210 | UACUUAGAAGCAUUCAGAAUGU | 292 |
| S210-AS293 | AUUCUGAAUGCUUCUAAGUAGCAGCCGAAAGGCUGC | 210 | UACUUAGAAGCATUCAGAAUGT | 293 |
| S210-AS366 | AUUCUGAAUGCUUCUAAGUAGCAGCCGAAAGGCUGC | 210 | UACUUAGAAGCAUUCAGAAUGG | 366 |
| S211-AS294 | UUCUGAAUGCUUCUAAGUAAGCAGCCGAAAGGCUGC | 211 | UTACUUAGAAGCAUUCAGAATG | 294 |
| S211-AS295 | UUCUGAAUGCUUCUAAGUAAGCAGCCGAAAGGCUGC | 211 | UUACUUAGAAGCAUUCAGAAUG | 295 |
| S211-AS367 | UUCUGAAUGCUUCUAAGUAAGCAGCCGAAAGGCUGC | 211 | UUACUUAGAAGCAUUCAGAAGG | 367 |
| S212-AS296 | UGAAUGCUUCUAAGUAAAUAGCAGCCGAAAGGCUGC | 212 | UAUUUACUUAGAAGCAUUCAGG | 296 |
| S212-AS297 | UGAAUGCUUCUAAGUAAAUAGCAGCCGAAAGGCUGC | 212 | UAUUUACUUAGAAGCAUUCAGA | 297 |
| S212-AS298 | UGAAUGCUUCUAAGUAAAUAGCAGCCGAAAGGCUGC | 212 | AUUUACUUAGAAGCAUUCAGG | 298 |
| S212-AS299 | UGAAUGCUUCUAAGUAAAUAGCAGCCGAAAGGCUGC | 212 | UAUUUACUUAGAAGCATUCAGA | 299 |
| S213-AS300 | GAAUGCUUCUAAGUAAAUACGCAGCCGAAAGGCUGC | 213 | GUAUUUACUUAGAAGCAUUCAG | 300 |
| S213-AS301 | GAAUGCUUCUAAGUAAAUACGCAGCCGAAAGGCUGC | 213 | GTAUUUACUUAGAAGCAUTCAG | 301 |
| S214-AS302 | AAUGCUUCUAAGUAAAUACAGCAGCCGAAAGGCUGC | 214 | UGUAUUUACUUAGAAGCAUUGG | 302 |
| S215-AS303 | AUGCUUCUAAGUAAAUACAAGCAGCCGAAAGGCUGC | 215 | UUGUAUUUACUUAGAAGCAUGG | 303 |
| S216-AS304 | UGAGAUAGUUUUCAUCCAUAGCAGCCGAAAGGCUGC | 216 | UAUGGAUGAAAACUAUCUCAGG | 304 |
| S217-AS305 | GAGAUAGUUUUCAUCCAUAAGCAGCCGAAAGGCUGC | 217 | UUAUGGAUGAAAACUAUCUCGG | 305 |
| S218-AS306 | AUUUACAAACUGAAGAGUAAGCAGCCGAAAGGCUGC | 218 | UUACUCUUCAGUUUGUAAAUGG | 306 |
| S219-AS307 | AAUACAAGACUGCCAUAUUAGCAGCCGAAAGGCUGC | 219 | UAAUAUGGCAGUCUUGUAUUGG | 307 |
| S220-AS308 | AUACAAGACUGCCAUAUUAAGCAGCCGAAAGGCUGC | 220 | UUAAUAUGGCAGUCUUGUAUGG | 308 |
| S221-AS309 | UACAAGACUGCCAUAUUAAAGCAGCCGAAAGGCUGC | 221 | UUUAAUAUGGCAGUCUUGUAGG | 309 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S222-AS310 | CAAGACUGCCAUAUUAAAUAGCAGCCGAAAGGCUGC | 222 | UAUUUAAUAUGGCAGUCUUGGG | 310 |
| S223-AS311 | AAGACUGCCAUAUUAAAUUAGCAGCCGAAAGGCUGC | 223 | UAAUUUAAUAUGGCAGUCUUGG | 311 |
| S224-AS312 | AGACUGCCAUAUUAAAUUUAGCAGCCGAAAGGCUGC | 224 | UAAAUUUAAUAUGGCAGUCUGG | 312 |
| S225-AS313 | GACUGCCAUAUUAAAUUUUAGCAGCCGAAAGGCUGC | 225 | UAAAAUUUAAUAUGGCAGUCGG | 313 |
| S226-AS314 | ACUGCCAUAUUAAAUUUUUAGCAGCCGAAAGGCUGC | 226 | UAAAAAUUUAAUAUGGCAGUGG | 314 |
| S227-AS315 | AGUAUGAAUUAUUCAAUUUAGCAGCCGAAAGGCUGC | 227 | UAAAUUGAAUAAUUCAUACUGG | 315 |
| S228-AS316 | GUAUGAAUUAUUCAAUUUAAGCAGCCGAAAGGCUGC | 228 | UUAAAUUGAAUAAUUCAUACGG | 316 |
| S229-AS317 | GAUGGAGUGCUGUUUUGUUAGCAGCCGAAAGGCUGC | 229 | UAACAAAACAGCACUCCAUCGG | 317 |
| S230-AS318 | AUGGAGUGCUGUUUUGUUAAGCAGCCGAAAGGCUGC | 230 | UUAACAAAACAGCACUCCAUGG | 318 |
| S231-AS319 | GGAGUGCUGUUUUGUUAUAAGCAGCCGAAAGGCUGC | 231 | UUAUAACAAAACAGCACUCCGG | 319 |
| S232-AS320 | GAGUGCUGUUUUGUUAUAUAGCAGCCGAAAGGCUGC | 232 | UAUAUAACAAAACAGCACUCGG | 320 |
| S233-AS321 | CUGUUUUGUUAUAUAAUUUAGCAGCCGAAAGGCUGC | 233 | UAAAUUAUAUAACAAAACAGGG | 321 |
| S234-AS322 | UGCAGAGGUUUUAAAUACUAGCAGCCGAAAGGCUGC | 234 | UAGUAUUUAAAACCUCUGCAGG | 322 |
| S235-AS323 | GCAGAGGUUUUAAAUACUAAGCAGCCGAAAGGCUGC | 235 | UUAGUAUUUAAAACCUCUGCGG | 323 |
| S236-AS324 | CAGAGGUUUUAAAUACUAGAGCAGCCGAAAGGCUGC | 236 | UCUAGUAUUUAAAACCUCUGGG | 324 |
| S237-AS325 | GAGGUUUUAAAUACUAGUUAGCAGCCGAAAGGCUGC | 237 | UAACUAGUAUUUAAACCUCGG | 325 |
| S238-AS326 | AGAUUUUGUUACAUAUUUUAGCAGCCGAAAGGCUGC | 238 | UAAAAUAUGUAACAAAAUCUGG | 326 |
| S239-AS327 | AUUUUGUUACAUAUUUUUAAGCAGCCGAAAGGCUGC | 239 | UUAAAAAUAUGUAACAAAAUGG | 327 |
| S240-AS328 | AAAAUACUCACUUUAUGCUAGCAGCCGAAAGGCUGC | 240 | UAGCAUAAAGUGAGUAUUUGG | 328 |
| S241-AS329 | AAAUACUCACUUUAUGCUUAGCAGCCGAAAGGCUGC | 241 | UAAGCAUAAAGUGAGUAUUUGG | 329 |
| S242-AS330 | AAUACUCACUUUAUGCUUAAGCAGCCGAAAGGCUGC | 242 | UUAAGCAUAAAGUGAGUAUUGG | 330 |
| S243-AS331 | AUAAAAGGUUUUGUCAAACAGCAGCCGAAAGGCUGC | 243 | UGUUUGACAAAACCUUUUAUGG | 331 |
| S244-AS332 | AGGUUUUGUCAAACAUUGCAGCAGCCGAAAGGCUGC | 244 | UGCAAUGUUUGACAAAACCUGG | 332 |
| S245-AS333 | GGUUUUGUCAAACAUUGCAAGCAGCCGAAAGGCUGC | 245 | UUGCAAUGUUUGACAAAACCGG | 333 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S246-AS334 | GCAAGUAUUCGGUGCUAUAAGCAGCCGAAAGGCUGC | 246 | UUAUAGCACCGAAUACUUGCGG | 334 |
| S247-AS335 | AGAUGGAAGUUUCUACUGUAGCAGCCGAAAGGCUGC | 247 | UACAGUAGAAACUUCCAUCUGG | 335 |
| S248-AS336 | AUGGAAGUUUCUACUGUAUAGCAGCCGAAAGGCUGC | 248 | UAUACAGUAGAAACUUCCAUGG | 336 |
| S249-AS337 | GGAAGUUUCUACUGUAUAGAGCAGCCGAAAGGCUGC | 249 | UCUAUACAGUAGAAACUUCCGG | 337 |
| S250-AS338 | GAAGUUUCUACUGUAUAGAAGCAGCCGAAAGGCUGC | 250 | UUCUAUACAGUAGAAACUUCGG | 338 |
| S251-AS339 | AAGUUUCUACUGUAUAGAAAGCAGCCGAAAGGCUGC | 251 | UUUCUAUACAGUAGAAACUUGG | 339 |
| S252-AS340 | AGUUUCUACUGUAUAGAAAAGCAGCCGAAAGGCUGC | 252 | UUUUCUAUACAGUAGAAACUGG | 340 |
| S253-AS341 | CUACUGUAUAGAAAUCACCAGCAGCCGAAAGGCUGC | 253 | UGGUGAUUUCUAUACAGUAGGG | 341 |
| S254-AS342 | CUGUAUAGAAAUCACCAUUAGCAGCCGAAAGGCUGC | 254 | UAAUGGUGAUUUCUAUACAGGG | 342 |
| S255-AS343 | GUCAUGACAACUACCAUUUAGCAGCCGAAAGGCUGC | 255 | UAAAUGGUAGUUGUCAUGACGG | 343 |
| S256-AS344 | GACAACUACCAUUUUUUUAAGCAGCCGAAAGGCUGC | 256 | UUAAAAAAAUGGUAGUUGUCGG | 344 |
| S257-AS345 | AGUUGGAUGUCUAAAACUCAGCAGCCGAAAGGCUGC | 257 | UGAGUUUUAGACAUCCAACUGG | 345 |
| S258-AS346 | GUUGGAUGUCUAAAACUCAAGCAGCCGAAAGGCUGC | 258 | UUGAGUUUUAGACAUCCAACGG | 346 |
| S259-AS347 | GAUGUCUAAAACUCAAGUAAGCAGCCGAAAGGCUGC | 259 | UUACUUGAGUUUUAGACAUCGG | 347 |
| S260-AS348 | GAUAAGUGUAAAGCCUUGUAGCAGCCGAAAGGCUGC | 260 | UACAAGGCUUUACACUUAUCGG | 348 |
| S261-AS349 | AUAAGUGUAAAGCCUUGUAAGCAGCCGAAAGGCUGC | 261 | UUACAAGGCUUUACACUUAUGG | 349 |
| S262-AS350 | GCCUUGUAACUGAAGAUGAAGCAGCCGAAAGGCUGC | 262 | UUCAUCUUCAGUUACAAGGCGG | 350 |
| S263-AS351 | GUGUAUAGAAACUAUUUUAAGCAGCCGAAAGGCUGC | 263 | UUAAAAUAGUUUCUAUACACGG | 351 |
| S264-AS352 | AAAGACUUUGUUGACAUCAAGCAGCCGAAAGGCUGC | 264 | UUGAUGUCAACAAAGUCUUUGG | 352 |
| S265-AS353 | GAAGAUGCUUUUUAAAACUAGCAGCCGAAAGGCUGC | 265 | UAGUUUUAAAAGCAUCUUCGG | 353 |
| S266-AS354 | AAGAUGCUUUUUAAAACUAAGCAGCCGAAAGGCUGC | 266 | UUAGUUUUAAAAAGCAUCUUGG | 354 |
| S267-AS355 | GAGCUAUUGCUGAUUAGUUAGCAGCCGAAAGGCUGC | 267 | UAACUAAUCAGCAAUAGCUCGG | 355 |
| S268-AS356 | GUGUUGUUAAUGUUUGCUGAGCAGCCGAAAGGCUGC | 268 | UCAGCAAACAUUAACAACACGG | 356 |
| S269-AS357 | GUUGUUAAUGUUUGCUGUAAGCAGCCGAAAGGCUGC | 269 | UUACAGCAAACAUUAACAACGG | 357 |

TABLE 7-continued

HMGB1 RNAi Oligonucleotide Sequences

| Sense (S) - Antisense (AS) Designation | Sense Sequence/mRNA seq | S SEQ ID NO | Antisense Sequence | AS SEQ ID NO |
|---|---|---|---|---|
| S270-AS358 | UGUUAAUGUUUGCUGUAU UAGCAGCCGAAAGGCUGC | 270 | UAAUACAGCAAACA UUAACAGG | 358 |
| S271-AS359 | GUUAAUGUUUGCUGUAUU UAGCAGCCGAAAGGCUGC | 271 | UAAAUACAGCAAAC AUUAACGG | 359 |
| S272-AS360 | UUAAUGUUUGCUGUAUUU AAGCAGCCGAAAGGCUGC | 272 | UUAAAUACAGCAAA CAUUAAGG | 360 |
| S363-AS368 | UCUGAAUGCUUCUAAGUA AAGCAGCCGAAAGGCUGC | 363 | UUUACUUAGAAGCA UUCAGAGG | 368 |
| S364-AS369 | CUGAAUGCUUCUAAGUAA AAGCAGCCGAAAGGCUGC | 364 | UUUUACUUAGAAGC AUUCAGGG | 369 |
| S365-AS370 | GAAUGCUUCUAAGUAAAU AAGCAGCCGAAAGGCUGC | 365 | UUAUUUACUUAGA AGCAUUCGG | 370 |

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide for reducing expression of HMGB1, the oligonucleotide comprising an antisense strand of 15 to 30 nucleotides in length, wherein the antisense strand has a region of complementarity to HMGB1 that is complementary to at least 15 contiguous nucleotides of a sequence as set forth in SEQ ID NOs: 374-381, 193-272, and 363-365, further comprising a sense strand of 15 to 50 nucleotides in length, wherein the sense strand forms a duplex region with the antisense strand, wherein the sense strand comprises a sequence as set forth in any one of SEQ ID NOs: 193-272 or 363-365.

2. The oligonucleotide of claim 1, wherein the sense strand comprises a sequence as set forth in SEQ ID NOs: 204, 211, 364, or 365.

3. The oligonucleotide of claim 1, wherein the antisense strand comprises a sequence as set forth in any one of SEQ ID NOs: 273-362 or 366-370.

4. The oligonucleotide of claim 2, wherein the antisense strand comprises a sequence as set forth in any one of SEQ ID NOs: 274, 276, 286, 292, 296, 367, 369 or 370.

5. An oligonucleotide for reducing expression of HMGB1, the oligonucleotide comprising an antisense strand of 15 to 30 nucleotides in length, wherein the antisense strand has a region of complementarity to HMGB1 that is complementary to at least 15 contiguous nucleotides of a sequence as set forth in SEQ ID NOs: 374-381, 193-272, and 363-365, further comprising a sense strand of 15 to 50 nucleotides in length, wherein the sense strand forms a duplex region with the antisense strand, wherein the sense strand comprises at its 3'-end a stem-loop set forth as: $S_1$-L-$S_2$, wherein $S_1$ is complementary to $S_2$, and wherein L forms a loop between $S_1$ and $S_2$ of 3 to 5 nucleotides in length.

6. An oligonucleotide for reducing expression of HMGB1, the oligonucleotide comprising an antisense strand of 15 to 30 nucleotides in length, wherein the antisense strand has a region of complementarity to HMGB1 that is complementary to at least 15 contiguous nucleotides of a sequence as set forth in SEQ ID NOs: 374-381, 193-272, and 363-365, wherein:
the oligonucleotide comprises at least one modified nucleotide, or at least one modified internucleotide linkage, or at least one targeting ligand; and/or
the 4'-carbon of the sugar of the 5'-nucleotide of the antisense strand comprises a phosphate analog.

7. The oligonucleotide of claim 6, wherein the oligonucleotide comprises at least one modified internucleotide linkage.

8. The oligonucleotide of claim 7, wherein the at least one modified internucleotide linkage is a phosphorothioate linkage.

9. The oligonucleotide of claim 6, wherein the 4'-carbon of the sugar of the 5'-nucleotide of the antisense strand comprises a phosphate analog.

10. The oligonucleotide of claim 6, wherein the oligonucleotide comprises at least one targeting ligand, wherein each targeting ligand comprises a N-acetylgalactosamine (GalNAc) moiety.

11. A composition comprising an oligonucleotide of claim 1 and an excipient.

12. A method of delivering an oligonucleotide to a subject, the method comprising administering the composition of claim 11 to the subject.

13. The oligonucleotide of claim 6, wherein the oligonucleotide comprises at least one modified nucleotide.

14. The oligonucleotide of claim 13, wherein the at least one modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

15. The oligonucleotide of claim 6, further comprising a sense strand of 15 to 50 nucleotides in length, wherein the sense strand forms a duplex region with the antisense strand.

16. The oligonucleotide of claim 15, wherein the sense strand comprises a sequence as set forth in any one of SEQ ID NOs: 193-272 or 363-365.

17. A composition comprising an oligonucleotide of claim 5 and an excipient.

18. A composition comprising an oligonucleotide of claim 6 and an excipient.

19. A method of delivering an oligonucleotide to a subject, the method comprising administering the composition of claim 17 to the subject.

20. A method of delivering an oligonucleotide to a subject, the method comprising administering the composition of claim 18 to the subject.

\* \* \* \* \*

SEQUENCE LISTING

<160> NUMBER OF SEQ ID NOS: 381

<210> SEQ ID NO 1
<211> LENGTH: 25
<212> TYPE: DNA
<213> ORGANISM: Artificial Sequence

```
<220> FEATURE:
<223> OTHER INFORMATION: Synthetic Polynucleotide

<400> SEQUENCE: 1
agauuuguuu uuaaacugua cagtg                                    25

<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 2
guacaguguc uuuuuugua uagtt                                     25

<210> SEQ ID NO 3
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 3
acagugucuu uuuuguaua guuaa                                     25

<210> SEQ ID NO 4
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 4
agugucuuuu uuuguauagu uaaca                                    25

<210> SEQ ID NO 5
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 5
gugucuuuuu uuguauaguu aacac                                    25

<210> SEQ ID NO 6
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 6
ggugguauuu ucaauagcca cuaac                                    25

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
guauuuucaa uagccacuaa ccutg                                    25
```

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
gugcacagca caaauuaguu auata                                     25

<210> SEQ ID NO 9
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 9
guugucucug augcagcuua uacga                                     25

<210> SEQ ID NO 10
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 10
ucugaugcag cuuauacgaa auaat                                     25

<210> SEQ ID NO 11
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 11
cugaugcagc uuauacgaaa uaatt                                     25

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 12
gaugcagcuu auacgaaaua auugt                                     25

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 13
augcagcuua uacgaaauaa uugtt                                     25

<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide -continued

```
<400> SEQUENCE: 14
gcagcuuaua cgaaauaauu guugt                                    25

<210> SEQ ID NO 15
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 15
cagcuuauac gaaauaauug uugtt                                    25

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 16
agcuuauacg aaauaauugu ugutc                                    25

<210> SEQ ID NO 17
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 17
gcuuauacga aauaauuguu guuct                                    25

<210> SEQ ID NO 18
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 18
uacgaaauaa uuguuguucu guuaa                                    25

<210> SEQ ID NO 19
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 19
acgaaauaau uguuguucug uuaac                                    25

<210> SEQ ID NO 20
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 20
cgaaauaauu guuguucugu uaact                                    25

<210> SEQ ID NO 21
```

```
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 21 gaauaauug uuguucuguu aactg                                          25

<210> SEQ ID NO 22
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 22
aaauaauugu uguucuguua acuga                                         25

<210> SEQ ID NO 23
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 23
aauaauuguu guucuguuaa cugaa                                         25

<210> SEQ ID NO 24
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 24
auaauuguug uucuguuaac ugaat                                         25

<210> SEQ ID NO 25
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 25
uaauuguugu ucuguuaacu gaata                                         25

<210> SEQ ID NO 26
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 26
aauuguuguu cuguuaacug aauac                                         25

<210> SEQ ID NO 27
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 27
```
auuguuguuc uguuaacuga auacc					25

<210> SEQ ID NO 28
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 28
uuguuguucu guuaacugaa uacca					25

<210> SEQ ID NO 29
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 29
uguuguucug uuaacugaau accac					25

<210> SEQ ID NO 30
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 30
guuguucugu uaacugaaua ccact					25

<210> SEQ ID NO 31
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 31
uuguucuguu aacugaauac cactc					25

<210> SEQ ID NO 32
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 32
guucuguuaa cugaauacca cuctg					25

<210> SEQ ID NO 33
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 33
uguuaacuga auaccacucu guaat					25

<210> SEQ ID NO 34
<211> LENGTH: 25
<212> TYPE: DNA

<213> ORGANISM: Artificial Sequence
<220> FEATURE:
<223> OTHER INFORMATION: Synthetic Polynucleotide

<400> SEQUENCE: 34
guuaacugaa uaccacucug uaatt                                                25

<210> SEQ ID NO 35
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 35
uuaacugaau accacucugu aautg                                                25

<210> SEQ ID NO 36
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 36
uaacugaaua ccacucugua auugc                                                25

<210> SEQ ID NO 37
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 37
aacugaauac cacucuguaa uugca                                                25

<210> SEQ ID NO 38
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 38
acugaauacc acucuguaau ugcaa                                                25

<210> SEQ ID NO 39
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 39
cugaauacca cucuguaauu gcaaa                                                25

<210> SEQ ID NO 40
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 40
ugaauaccac ucuguaauug caaaa                                                25

<210> SEQ ID NO 41
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 41
gaauaccacu cuguaauugc aaaaa                                      25

<210> SEQ ID NO 42
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 42
aauaccacuc uguaauugca aaaaa                                      25

<210> SEQ ID NO 43
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 43
auaccacucu guaauugcaa aaaaa                                      25

<210> SEQ ID NO 44
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 44
augcagcuua uacgaagaua auugt                                      25

<210> SEQ ID NO 45
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 45
ugcagcuuau acgaagauaa uugtt                                      25

<210> SEQ ID NO 46
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 46
gcagcuuaua cgaagauaau ugutg                                      25

<210> SEQ ID NO 47
<211> LENGTH: 25
<212> TYPE: DNA
<213> ORGANISM: Artificial Sequence
<220> FEATURE:

<223> OTHER INFORMATION: Synthetic Polynucleotide

<400> SEQUENCE: 47
cagcuuauac gaagauaauu guugt                                    25

<210> SEQ ID NO 48
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 48
gcuuauacga agauaauugu ugutc                                    25

<210> SEQ ID NO 49
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 49
cuuauacgaa gauaauuguu guuct                                    25

<210> SEQ ID NO 50
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 50
auacgaagau aauguuguu cugtt                                     25

<210> SEQ ID NO 51
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 51
acgaagauaa uuguuguucu guuaa                                    25

<210> SEQ ID NO 52
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 52
cgaagauaau uguuguucug uuaac                                    25

<210> SEQ ID NO 53
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 53
gcagcuguuu uguugacauu cugaa                                    25

```
<210> SEQ ID NO 54
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 54 gcuguuugu ugacauucug aaugc                                          25

<210> SEQ ID NO 55
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 55
cuguuuuguu gacauucuga augct                                         25

<210> SEQ ID NO 56
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 56 guuuguuga cauucugaau gcutc                                          25

<210> SEQ ID NO 57
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 57
guugacauuc ugaaugcuuc uaagt                                         25

<210> SEQ ID NO 58
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 58
gacauucuga augcuucuaa guaaa                                         25

<210> SEQ ID NO 59
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 59
acauucugaa ugcuucuaag uaaat                                         25

<210> SEQ ID NO 60
<211> LENGTH: 25
<212> TYPE: RNA
<213> ORGANISM: Artificial Sequence
<220> FEATURE:
<223> OTHER INFORMATION: Synthetic Polynucleotide
```

<400> SEQUENCE: 60
auucugaaug cuucuaagua aauac                                                 25

<210> SEQ ID NO 61
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 61
uucugaaugc uucuaaguaa auaca                                                 25

<210> SEQ ID NO 62
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 62
ucugaaugcu cuaaguaaau acaa                                                  25

<210> SEQ ID NO 63
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 63
cugaaugcuu cuaaguaaau acaat                                                 25

<210> SEQ ID NO 64
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 64
ugaaugcuuc uaaguaaaua caatt                                                 25

<210> SEQ ID NO 65
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 65
gaaugcuucu aaguaaauac aautt                                                 25

<210> SEQ ID NO 66
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 66
aaugcuucua aguaaauaca auutt                                                 25

<210> SEQ ID NO 67
<211> LENGTH: 25

```
<212> TYPE: DNA
<213> ORGANISM: Artificial Sequence
<220> FEATURE:
<223> OTHER INFORMATION: Synthetic Polynucleotide

<400> SEQUENCE: 67
augcuucuaa guaaauacaa uuutt                                              25

<210> SEQ ID NO 68
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 68
ugcuucuaag uaaauacaau uuutt                                              25

<210> SEQ ID NO 69
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 69
guuguccuuu ucauaggucu gaaat                                              25

<210> SEQ ID NO 70
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 70
ugagauaguu uucauccaua acuga                                              25

<210> SEQ ID NO 71
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 71
gagauaguuu ucauccauaa cugaa                                              25

<210> SEQ ID NO 72
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 72
acauuuucau ccauaguuga agaat                                              25

<210> SEQ ID NO 73
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 73
```
cauuuacaaa cugaagagua aucaa     25

<210> SEQ ID NO 74
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 74
auuuacaaac ugaagaguaa ucaat     25

<210> SEQ ID NO 75
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 75
acaaacugaa gaguaaucaa ucuac     25

<210> SEQ ID NO 76
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 76
guaaugacag uuauauuuug cagtt     25

<210> SEQ ID NO 77
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 77
aaugacaguu auauuugca guutc     25

<210> SEQ ID NO 78
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 78
aauacaagac ugcuguacua uuugt     25

<210> SEQ ID NO 79
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 79
auacaagacu gcuguacuau uugtt     25

<210> SEQ ID NO 80
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 80
uacaagacug cuguacuauu ugutg                                            25

<210> SEQ ID NO 81
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 81
acaagacugc uguacuauuu guuga                                            25

<210> SEQ ID NO 82
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 82
caagacugcu guacuauuug uugac                                            25

<210> SEQ ID NO 83
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 83
gacugcugua cuauuuguug acctt                                            25

<210> SEQ ID NO 84
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 84
acugcuguac uauuuguuga ccuta                                            25

<210> SEQ ID NO 85
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 85
gugguuuguc ccuuuaugaa ucaga                                            25

<210> SEQ ID NO 86
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 86
caauacauuu gcuuuuucuu uauaa                                            25

```
<210> SEQ ID NO 87
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 87
auacauuugc uuuuucuuua uaaaa                                              25

<210> SEQ ID NO 88
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 88
ugauggagug cuguuauaua auutt                                              25

<210> SEQ ID NO 89
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 89
gauggagugc uguuuuguua uauaa                                              25

<210> SEQ ID NO 90
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 90
auggagugcu guuuguuau auaat                                               25

<210> SEQ ID NO 91
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 91
ggagugcugu uuguuauau aautt                                               25

<210> SEQ ID NO 92
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 92
gagugcuguu uuguuauaua auuta                                              25

<210> SEQ ID NO 93
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 93 cguuuuguu auauaauuua gacuu                                              25

<210> SEQ ID NO 94
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 94
cauuugcguu guuaauguaa uuuga                                             25

<210> SEQ ID NO 95
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 95
auguaauuuc aggaggaaua cugaa                                             25

<210> SEQ ID NO 96
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 96
gaguccugga ugauacuaau aaact                                             25

<210> SEQ ID NO 97
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 97
cacuguacag uuuaaaaaca aaucuua                                           27

<210> SEQ ID NO 98
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 98
aacuauacaa aaaagacac uguacag                                            27

<210> SEQ ID NO 99
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 99
uuaacuauac aaaaaagac acuguac                                            27

<210> SEQ ID NO 100
```

```
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 100
uguuaacuau acaaaaaag acacugu                                             27

<210> SEQ ID NO 101
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 101
guguuaacua uacaaaaaaa gacacug                                            27

<210> SEQ ID NO 102
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 102
guuaguggcu auugaaaaua ccaccag                                            27

<210> SEQ ID NO 103
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 103
caagguuagu ggcuauugaa aauacca                                            27

<210> SEQ ID NO 104
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 104
uauauaacua auuugugcug ugcacca                                            27

<210> SEQ ID NO 105
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 105
ucguauaagc ugcaucagag acaacug                                            27

<210> SEQ ID NO 106
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 106
```

-continued auuauuucgu auaagcugca ucagaga    27

<210> SEQ ID NO 107
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 107
aauuauuucg uauaagcugc aucagag    27

<210> SEQ ID NO 108
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 108
acaauuauuu cguauaagcu gcaucag    27

<210> SEQ ID NO 109
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 109
aacaauuauu ucguauaagc ugcauca    27

<210> SEQ ID NO 110
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 110
acaacaauua uuucguauaa gcugcau    27

<210> SEQ ID NO 111
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 111
aacaacaauu auuucguaua agcugca    27

<210> SEQ ID NO 112
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 112
gaacaacaau uauuucguau aagcugc    27

<210> SEQ ID NO 113
<211> LENGTH: 27
<212> TYPE: RNA

```
<213> ORGANISM: Artificial Sequence
<220> FEATURE:
<223> OTHER INFORMATION: Synthetic Polynucleotide

<400> SEQUENCE: 113
agaacaacaa uuauuucgua uaagcug                                              27

<210> SEQ ID NO 114
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 114
uuaacagaac aacaauuauu ucguaua                                              27

<210> SEQ ID NO 115
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 115
guuaacagaa caacaauuau uucguau                                              27

<210> SEQ ID NO 116
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 116
aguuaacaga acaacaauua uuucgua                                              27

<210> SEQ ID NO 117
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 117
caguuaacag aacaacaauu auuucgu                                              27

<210> SEQ ID NO 118
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 118
ucaguuaaca gaacaacaau uauuucg                                              27

<210> SEQ ID NO 119
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 119
uucaguuaac agaacaacaa uuauuuc                                              27
```

<210> SEQ ID NO 120
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 120
auucaguuaa cagaacaaca auuauuu                                              27

<210> SEQ ID NO 121
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 121
uauucaguua acagaacaac aauuauu                                              27

<210> SEQ ID NO 122
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 122
guauucaguu aacagaacaa caauuau                                              27

<210> SEQ ID NO 123
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 123
gguauucagu uaacagaaca acaauua                                              27

<210> SEQ ID NO 124
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 124
ugguauucag uuaacagaac aacaauu                                              27

<210> SEQ ID NO 125
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 125
gugguauuca guuaacagaa caacaau                                              27

<210> SEQ ID NO 126
<211> LENGTH: 27
<212> TYPE: RNA
<213> ORGANISM: Artificial Sequence
<220> FEATURE:

```
<223> OTHER INFORMATION: Synthetic Polynucleotide

<400> SEQUENCE: 126
agugguauuc aguuaacaga acaacaa                                              27

<210> SEQ ID NO 127
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 127
gagugguauu caguuaacag aacaaca                                              27

<210> SEQ ID NO 128
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 128
cagaguggua uucaguuaac agaacaa                                              27

<210> SEQ ID NO 129
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 129
auuacagagu gguauucagu uaacaga                                              27

<210> SEQ ID NO 130
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 130
aauuacagag ugguauucag uuaacag                                              27

<210> SEQ ID NO 131
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 131
caauuacaga gugguauuca guuaaca                                              27

<210> SEQ ID NO 132
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 132
gcaauuacag agugguauuc aguuaac                                              27
```

```
<210> SEQ ID NO 133
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 133
ugcaauuaca gagugguauu caguuaa                                    27

<210> SEQ ID NO 134
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 134
uugcaauuac agagugguau ucaguua                                    27

<210> SEQ ID NO 135
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 135
uuugcaauua cagaguggua uucaguu                                    27

<210> SEQ ID NO 136
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 136
uuuugcaauu acagagggu auucagu                                     27

<210> SEQ ID NO 137
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 137
uuuuugcaau uacagagugg uauucag                                    27

<210> SEQ ID NO 138
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 138
uuuuuugcaa uuacagagug guauuca                                    27

<210> SEQ ID NO 139
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 139
uuuuuuugca auuacagagu gguauuc                                              27

<210> SEQ ID NO 140
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 140
acaauuaucu ucguauaagc ugcauca                                              27

<210> SEQ ID NO 141
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 141
aacaauuauc uucguauaag cugcauc                                              27

<210> SEQ ID NO 142
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 142
caacaauuau cuucguauaa gcugcau                                              27

<210> SEQ ID NO 143
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 143
acaacaauua ucuucguaua agcugca                                              27

<210> SEQ ID NO 144
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 144
gaacaacaau uaucuucgua uaagcug                                              27

<210> SEQ ID NO 145
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 145
agaacaacaa uuaucuucgu auaagcu                                              27

<210> SEQ ID NO 146
<211> LENGTH: 27
```

```
<212> TYPE: RNA
<213> ORGANISM: Artificial Sequence
<220> FEATURE:
<223> OTHER INFORMATION: Synthetic Polynucleotide

<400> SEQUENCE: 146
aacagaacaa caauuaucuu cguauaa                                              27

<210> SEQ ID NO 147
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 147
uuaacagaac aacaauuauc uucguau                                              27

<210> SEQ ID NO 148
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 148
guuaacagaa caacaauuau cuucgua                                              27

<210> SEQ ID NO 149
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 149
uucagaaugu caacaaaaca gcugcaa                                              27

<210> SEQ ID NO 150
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 150
gcauucagaa ugucaacaaa acagcug                                              27

<210> SEQ ID NO 151
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 151
agcauucaga augucaacaa aacagcu                                              27

<210> SEQ ID NO 152
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 152
```
gaagcauuca gaaugucaac aaaacag 27

<210> SEQ ID NO 153
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 153
acuuagaagc auucagaaug ucaacaa 27

<210> SEQ ID NO 154
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 154
uuuacuuaga agcauucaga augucaa 27

<210> SEQ ID NO 155
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 155
auuuacuuag aagcauucag aaugca 27

<210> SEQ ID NO 156
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 156
guauuuacuu agaagcauuc agaaugu 27

<210> SEQ ID NO 157
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 157
uguauuuacu uagaagcauu cagaaug 27

<210> SEQ ID NO 158
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 158
uuguauuuac uuagaagcau ucagaau 27

<210> SEQ ID NO 159
<211> LENGTH: 27
<212> TYPE: RNA
<213> ORGANISM: Artificial Sequence

```
<220> FEATURE:
<223> OTHER INFORMATION: Synthetic Polynucleotide

<400> SEQUENCE: 159
auuguauuua cuuagaagca uucagaa                                              27

<210> SEQ ID NO 160
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 160
aauuguauuu acuuagaagc auucaga                                              27

<210> SEQ ID NO 161
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 161
aaauuguauu uacuuagaag cauucag                                              27

<210> SEQ ID NO 162
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 162
aaaauuguau uuacuuagaa gcauuca                                              27

<210> SEQ ID NO 163
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 163
aaaaauugua uuuacuuaga agcauuc                                              27

<210> SEQ ID NO 164
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 164
aaaaaauugu auuuacuuag aagcauu                                              27

<210> SEQ ID NO 165
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 165
auuucagacc uaugaaaagg acaacaa                                              27
```

<210> SEQ ID NO 166
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 166
ucaguuaugg augaaaacua ucucaac                                27

<210> SEQ ID NO 167
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 167
uucaguuaug gaugaaaacu aucucaa                                27

<210> SEQ ID NO 168
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 168
auucuucaac uauggaugaa aauguua                                27

<210> SEQ ID NO 169
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 169
uugauuacuc uucaguuugu aaaugua                                27

<210> SEQ ID NO 170
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 170
auugauuacu cuucaguuug uaaaugu                                27

<210> SEQ ID NO 171
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 171
guagauugau uacucuucag uuuguaa                                27

<210> SEQ ID NO 172
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 172
aacugcaaaa uauaacuguc auuacac                                                27

<210> SEQ ID NO 173
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 173
gaaacugcaa aauauaacug ucauuac                                                27

<210> SEQ ID NO 174
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 174
acaaauagua cagcagucuu guauuuu                                                27

<210> SEQ ID NO 175
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 175
aacaaauagu acagcagucu uguauuu                                                27

<210> SEQ ID NO 176
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 176
caacaaauag uacagcaguc uuguauu                                                27

<210> SEQ ID NO 177
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 177
ucaacaaaua guacagcagu cuuguau                                                27

<210> SEQ ID NO 178
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 178
gucaacaaau aguacagcag ucuugua                                                27

<210> SEQ ID NO 179

```
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 179
aaggucaaca aauaguacag cagucuu                                              27

<210> SEQ ID NO 180
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 180
uaaggucaac aaauaguaca gcagucu                                              27

<210> SEQ ID NO 181
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 181
ucugauucau aaagggacaa accacag                                              27

<210> SEQ ID NO 182
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 182
uuauaaagaa aaagcaaaug uauugga                                              27

<210> SEQ ID NO 183
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 183
uuuuauaaag aaaaagcaaa uguauug                                              27

<210> SEQ ID NO 184
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 184
aaaauuauau aacagcacuc caucaca                                              27

<210> SEQ ID NO 185
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 185
```
uuauauaaca aaacagcacu ccaucac                                              27

<210> SEQ ID NO 186
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 186
auuauauaac aaaacagcac uccauca                                              27

<210> SEQ ID NO 187
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 187
aaauuauaua acaaaacagc acuccau                                              27

<210> SEQ ID NO 188
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 188
uaaauuauau aacaaaacag cacucca                                              27

<210> SEQ ID NO 189
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 189
aagucuaaau uauauaacaa aacagca                                              27

<210> SEQ ID NO 190
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 190
ucaaauuaca uuaacaacgc aaaugua                                              27

<210> SEQ ID NO 191
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 191
uucaguauuc cuccugaaau uacauaa                                              27

<210> SEQ ID NO 192
<211> LENGTH: 27
<212> TYPE: RNA

<213> ORGANISM: Artificial Sequence
<220> FEATURE:
<223> OTHER INFORMATION: Synthetic Polynucleotide

<400> SEQUENCE: 192
aguuuauuag uaucauccag gacucag                                27

<210> SEQ ID NO 193
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 193
guacaguguc uuuuuugua gcagccgaaa ggcugc                       36

<210> SEQ ID NO 194
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 194 acagucuu uuuuuguaua gcagccgaaa ggcugc                        36

<210> SEQ ID NO 195
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 195 ucgaugcag cuuauacgaa gcagccgaaa ggcugc                       36

<210> SEQ ID NO 196
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 196
cugaugcagc uuauacgaaa gcagccgaaa ggcugc                      36

<210> SEQ ID NO 197
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 197
augcagcuua uacgaaauaa gcagccgaaa ggcugc                      36

<210> SEQ ID NO 198
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 198
gcagcuuaua cgaaauaaua gcagccgaaa ggcugc                      36

<210> SEQ ID NO 199
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 199
cagcuuauac gaaauaauua gcagccgaaa ggcugc         36

<210> SEQ ID NO 200
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 200
gcuuauacga aauaauugua gcagccgaaa ggcugc         36

<210> SEQ ID NO 201
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 201
aaauaauugu uguucuguua gcagccgaaa ggcugc         36

<210> SEQ ID NO 202
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 202
aauaauuguu guucuguuaa gcagccgaaa ggcugc         36

<210> SEQ ID NO 203
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 203
auuguuguuc uguuaacuga gcagccgaaa ggcugc         36

<210> SEQ ID NO 204
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 204
uuguuguucu guuaacugaa gcagccgaaa ggcugc         36

<210> SEQ ID NO 205
<211> LENGTH: 36
<212> TYPE: RNA
<213> ORGANISM: Artificial Sequence
<220> FEATURE:

<223> OTHER INFORMATION: Synthetic Polynucleotide

<400> SEQUENCE: 205
uguuguucug uuaacugaaa gcagccgaaa ggcugc    36

<210> SEQ ID NO 206
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 206
guuguucugu uaacugaaua gcagccgaaa ggcugc    36

<210> SEQ ID NO 207
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 207
aacugaauac cacucuguaa gcagccgaaa ggcugc    36

<210> SEQ ID NO 208
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 208
cugaauacca cucuguaaua gcagccgaaa ggcugc    36

<210> SEQ ID NO 209
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 209
aauaccacuc uguaauugca gcagccgaaa ggcugc    36

<210> SEQ ID NO 210
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 210
auucugaaug cuucuaagua gcagccgaaa ggcugc    36

<210> SEQ ID NO 211
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 211
uucugaaugc uucuaaguaa gcagccgaaa ggcugc    36

<210> SEQ ID NO 212
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 212
ugaaugcuuc uaaguaaaua gcagccgaaa ggcugc                                36

<210> SEQ ID NO 213
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 213
gaaugcuucu aaguaaauac gcagccgaaa ggcugc                                36

<210> SEQ ID NO 214
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 214
aaugcuucua aguaaauaca gcagccgaaa ggcugc                                36

<210> SEQ ID NO 215
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 215
augcuucuaa guaaauacaa gcagccgaaa ggcugc                                36

<210> SEQ ID NO 216
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 216
ugagauaguu uucauccaua gcagccgaaa ggcugc                                36

<210> SEQ ID NO 217
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 217
gagauaguuu ucauccauaa gcagccgaaa ggcugc                                36

<210> SEQ ID NO 218
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 218
auuuacaaac ugaagaguaa gcagccgaaa ggcugc                                36

<210> SEQ ID NO 219
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 219
aauacaagac ugccauauua gcagccgaaa ggcugc                                36

<210> SEQ ID NO 220
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 220
auacaagacu gccauauuaa gcagccgaaa ggcugc                                36

<210> SEQ ID NO 221
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 221
uacaagacug ccauauuaaa gcagccgaaa ggcugc                                36

<210> SEQ ID NO 222
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 222
caagacugcc auauuaaaua gcagccgaaa ggcugc                                36

<210> SEQ ID NO 223
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 223
aagacugcca uauuaaauua gcagccgaaa ggcugc                                36

<210> SEQ ID NO 224
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 224
agacugccau auuaaauuua gcagccgaaa ggcugc                                36

<210> SEQ ID NO 225
<211> LENGTH: 36

```
<212> TYPE: RNA
<213> ORGANISM: Artificial Sequence
<220> FEATURE:
<223> OTHER INFORMATION: Synthetic Polynucleotide

<400> SEQUENCE: 225
gacugccaua uuaaauuuua gcagccgaaa ggcugc                              36

<210> SEQ ID NO 226
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 226
acugccauau uaaauuuuua gcagccgaaa ggcugc                              36

<210> SEQ ID NO 227
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 227
aguaugaauu auucaauuua gcagccgaaa ggcugc                              36

<210> SEQ ID NO 228
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 228
guaugaauua uucaauuaa gcagccgaaa ggcugc                               36

<210> SEQ ID NO 229
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 229
gauggagugc uguuuuguua gcagccgaaa ggcugc                              36

<210> SEQ ID NO 230
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 230
auggagugcu guuuuguuaa gcagccgaaa ggcugc                              36

<210> SEQ ID NO 231
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 231
```
ggagugcugu uuguuauaaa gcagccgaaa ggcugc                                36

<210> SEQ ID NO 232
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 232
gagugcuguu uuguuauaua gcagccgaaa ggcugc                                36

<210> SEQ ID NO 233
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 233
cuguuuuguu auauaauuua gcagccgaaa ggcugc                                36

<210> SEQ ID NO 234
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 234
ugcagagguu uuaaauacua gcagccgaaa ggcugc                                36

<210> SEQ ID NO 235
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 235
gcagagguuu uaaauacuaa gcagccgaaa ggcugc                                36

<210> SEQ ID NO 236
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 236
cagagguuuu aaauacuaga gcagccgaaa ggcugc                                36

<210> SEQ ID NO 237
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 237
gagguuuuaa auacuaguua gcagccgaaa ggcugc                                36

<210> SEQ ID NO 238
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 238 agauuuguu acauauuuua gcagccgaaa ggcugc                          36

<210> SEQ ID NO 239
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 239 auuuguuac auauuuuaa gcagccgaaa ggcugc                           36

<210> SEQ ID NO 240
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 240
aaaauacuca cuuuaugcua gcagccgaaa ggcugc                         36

<210> SEQ ID NO 241
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 241
aaauacucac uuuaugcuua gcagccgaaa ggcugc                         36

<210> SEQ ID NO 242
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 242
aauacucacu uuaugcuaa gcagccgaaa ggcugc                          36

<210> SEQ ID NO 243
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 243
auaaaagguu uugucaaaca gcagccgaaa ggcugc                         36

<210> SEQ ID NO 244
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 244
agguuuuguc aaacauugca gcagccgaaa ggcugc                         36

<210> SEQ ID NO 245
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 245
gguuuuguca aacauugcaa gcagccgaaa ggcugc                                    36

<210> SEQ ID NO 246
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 246
gcaaguauuc ggugcuauaa gcagccgaaa ggcugc                                    36

<210> SEQ ID NO 247
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 247
agauggaagu uucuacugua gcagccgaaa ggcugc                                    36

<210> SEQ ID NO 248
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 248
auggaaguuu cuacuguaua gcagccgaaa ggcugc                                    36

<210> SEQ ID NO 249
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 249
ggaaguuucu acuguauaga gcagccgaaa ggcugc                                    36

<210> SEQ ID NO 250
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 250
gaaguuucua cuguauagaa gcagccgaaa ggcugc                                    36

<210> SEQ ID NO 251
<211> LENGTH: 36
<212> TYPE: RNA
<213> ORGANISM: Artificial Sequence
<220> FEATURE:
<223> OTHER INFORMATION: Synthetic Polynucleotide

```
<400> SEQUENCE: 251
aaguuucuac uguauagaaa gcagccgaaa ggcugc                                36

<210> SEQ ID NO 252
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 252
aguuucuacu guauagaaaa gcagccgaaa ggcugc                                36

<210> SEQ ID NO 253
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 253
cuacuguaua gaaaucacca gcagccgaaa ggcugc                                36

<210> SEQ ID NO 254
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 254
cuguauagaa aucaccauua gcagccgaaa ggcugc                                36

<210> SEQ ID NO 255
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 255
gucaugacaa cuaccauuua gcagccgaaa ggcugc                                36

<210> SEQ ID NO 256
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 256
gacaacuacc auuuuuuaa gcagccgaaa ggcugc                                 36

<210> SEQ ID NO 257
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 257
aguuggaugu cuaaaacuca gcagccgaaa ggcugc                                36

<210> SEQ ID NO 258
```

```
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 258
guuggauguc uaaaacucaa gcagccgaaa ggcugc                                    36

<210> SEQ ID NO 259
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 259
gaugucuaaa acucaaguaa gcagccgaaa ggcugc                                    36

<210> SEQ ID NO 260
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 260
gauaagugua aagccuugua gcagccgaaa ggcugc                                    36

<210> SEQ ID NO 261
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 261
auaaguguaa agccuuguaa gcagccgaaa ggcugc                                    36

<210> SEQ ID NO 262
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 262
gccuuguaac ugaagaugaa gcagccgaaa ggcugc                                    36

<210> SEQ ID NO 263
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 263
guguauagaa acuauuuuaa gcagccgaaa ggcugc                                    36

<210> SEQ ID NO 264
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 264
```
aaagacuuug uugacaucaa gcagccgaaa ggcugc                                36

<210> SEQ ID NO 265
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 265
gaagaugcuu uuuaaaacua gcagccgaaa ggcugc                                36

<210> SEQ ID NO 266
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 266
aagaugcuuu uuaaaacuaa gcagccgaaa ggcugc                                36

<210> SEQ ID NO 267
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 267
gagcuauugc ugauuaguua gcagccgaaa ggcugc                                36

<210> SEQ ID NO 268
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 268
guguuguuaa uguuugcuga gcagccgaaa ggcugc                                36

<210> SEQ ID NO 269
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 269
guuguuaaug uuugcuguaa gcagccgaaa ggcugc                                36

<210> SEQ ID NO 270
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 270
uguuaauguu ugcuguauua gcagccgaaa ggcugc                                36

<210> SEQ ID NO 271
<211> LENGTH: 36
<212> TYPE: RNA

```
<213> ORGANISM: Artificial Sequence
<220> FEATURE:
<223> OTHER INFORMATION: Synthetic Polynucleotide

<400> SEQUENCE: 271
guuaauguuu gcuguauuua gcagccgaaa ggcugc                                  36

<210> SEQ ID NO 272
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 272
uuaauguuug cuguauuuaa gcagccgaaa ggcugc                                  36

<210> SEQ ID NO 273
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 273
uacaaaaaaa gacacuguac gg                                                 22

<210> SEQ ID NO 274
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 274
uauacaaaaa aagacacugu gg                                                 22

<210> SEQ ID NO 275
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 275
uucguauaag cugcaucaga ga                                                 22

<210> SEQ ID NO 276
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 276
uuucguauaa gcugcaucag ag                                                 22

<210> SEQ ID NO 277
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 277
uuucguauaa gcugcaucag gg                                                 22
```

<210> SEQ ID NO 278
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 278
uucguauaag cugcaucagg g                                              21

<210> SEQ ID NO 279
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 279
uuauuucgua uaagcugcau gg                                             22

<210> SEQ ID NO 280
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 280
uauuauuucg uauaagcugc gg                                             22

<210> SEQ ID NO 281
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 281
uaauuauuuc guauaagcug gg                                             22

<210> SEQ ID NO 282
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 282
uacaauuauu ucguauaagc gg                                             22

<210> SEQ ID NO 283
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 283
uaacagaaca acaauuauuu gg                                             22

<210> SEQ ID NO 284
<211> LENGTH: 22
<212> TYPE: RNA
<213> ORGANISM: Artificial Sequence
<220> FEATURE:

<223> OTHER INFORMATION: Synthetic Polynucleotide

<400> SEQUENCE: 284
uuaacagaac aacaauuauu gg                                    22

<210> SEQ ID NO 285
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 285
ucaguuaaca gaacaacaau gg                                    22

<210> SEQ ID NO 286
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 286
uucaguuaac agaacaacaa gg                                    22

<210> SEQ ID NO 287
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 287
uuucaguuaa cagaacaaca gg                                    22

<210> SEQ ID NO 288
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 288
uauucaguua acagaacaac gg                                    22

<210> SEQ ID NO 289
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 289
uuacagagug guauucaguu gg                                    22

<210> SEQ ID NO 290
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 290
uauuacagag ugguauucag gg                                    22

```
<210> SEQ ID NO 291
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 291
ugcaauuaca gagugguauu gg                                              22

<210> SEQ ID NO 292
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 292
uacuuagaag cauucagaau gu                                              22

<210> SEQ ID NO 293
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 293
uacuuagaag catucagaau gt                                              22

<210> SEQ ID NO 294
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 294
utacuuagaa gcauucagaa tg                                              22

<210> SEQ ID NO 295
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 295
uuacuuagaa gcauucagaa ug                                              22

<210> SEQ ID NO 296
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 296
uauuuacuua gaagcauuca gg                                              22

<210> SEQ ID NO 297
<211> LENGTH: 22
<212> TYPE: RNA
<213> ORGANISM: Artificial Sequence
<220> FEATURE:
<223> OTHER INFORMATION: Synthetic Polynucleotide
```

<400> SEQUENCE: 297
uauuuacuua gaagcauuca ga                                              22

<210> SEQ ID NO 298
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 298
auuuacuuag aagcauucag g                                               21

<210> SEQ ID NO 299
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 299
uauuuacuua gaagcatuca ga                                              22

<210> SEQ ID NO 300
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 300
guauuuacuu agaagcauuc ag                                              22

<210> SEQ ID NO 301
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 301
gtauuuacuu agaagcautc ag                                              22

<210> SEQ ID NO 302
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 302
uguauuuacu uagaagcauu gg                                              22

<210> SEQ ID NO 303
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 303
uuguauuuac uuagaagcau gg                                              22

<210> SEQ ID NO 304
<211> LENGTH: 22

```
<212> TYPE: RNA
<213> ORGANISM: Artificial Sequence
<220> FEATURE:
<223> OTHER INFORMATION: Synthetic Polynucleotide

<400> SEQUENCE: 304
uauggaugaa aacuaucuca gg                                              22

<210> SEQ ID NO 305
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 305
uuauggauga aaacuaucuc gg                                              22

<210> SEQ ID NO 306
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 306
uuacucuuca guuuguaaau gg                                              22

<210> SEQ ID NO 307
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 307
uaauauggca gucuuguauu gg                                              22

<210> SEQ ID NO 308
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 308
uuaauauggc agucuuguau gg                                              22

<210> SEQ ID NO 309
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 309
uuuaauaugg cagucuugua gg                                              22

<210> SEQ ID NO 310
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 310
```
uauuuaauau ggcagucuug gg 22

<210> SEQ ID NO 311
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 311
uaauuuaaua uggcagucuu gg 22

<210> SEQ ID NO 312
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 312
uaaauuuaau auggcagucu gg 22

<210> SEQ ID NO 313
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 313
uaaaauuuaa uauggcaguc gg 22

<210> SEQ ID NO 314
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 314
uaaaaauuua auauggcagu gg 22

<210> SEQ ID NO 315
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 315
uaaauugaau aauucauacu gg 22

<210> SEQ ID NO 316
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 316
uuaaauugaa uaauucauac gg 22

<210> SEQ ID NO 317
<211> LENGTH: 22
<212> TYPE: RNA
<213> ORGANISM: Artificial Sequence

```
<220> FEATURE:
<223> OTHER INFORMATION: Synthetic Polynucleotide

<400> SEQUENCE: 317
uaacaaaaca gcacuccauc gg                                              22

<210> SEQ ID NO 318
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 318
uuaacaaaac agcacuccau gg                                              22

<210> SEQ ID NO 319
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 319
uuauaacaaa acagcacucc gg                                              22

<210> SEQ ID NO 320
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 320
uauauaacaa aacagcacuc gg                                              22

<210> SEQ ID NO 321
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 321
uaaauuauau aacaaaacag gg                                              22

<210> SEQ ID NO 322
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 322
uaguauuuaa aaccucugca gg                                              22

<210> SEQ ID NO 323
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 323
uuaguauuua aaaccucugc gg                                              22
```

```
<210> SEQ ID NO 324
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 324
ucuaguauuu aaaaccucug gg                                              22

<210> SEQ ID NO 325
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 325
uaacuaguau uuaaaaccuc gg                                              22

<210> SEQ ID NO 326
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 326
uaaaauaugu aacaaaaucu gg                                              22

<210> SEQ ID NO 327
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 327
uuaaaaauau guaacaaaau gg                                              22

<210> SEQ ID NO 328
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 328
uagcauaaag ugaguauuuu gg                                              22

<210> SEQ ID NO 329
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 329
uaagcauaaa gugaguauuu gg                                              22

<210> SEQ ID NO 330
<211> LENGTH: 22
<212> TYPE: RNA
<213> ORGANISM: Artificial Sequence
<220> FEATURE:
<223> OTHER INFORMATION: Synthetic Polynucleotide
```

<400> SEQUENCE: 330
uuaagcauaa agugaguauu gg                                        22

<210> SEQ ID NO 331
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 331
uguuugacaa aaccuuuuau gg                                        22

<210> SEQ ID NO 332
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 332
ugcaauguuu gacaaaaccu gg                                        22

<210> SEQ ID NO 333
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 333
uugcaauguu ugacaaaacc gg                                        22

<210> SEQ ID NO 334
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 334
uuauagcacc gaauacuugc gg                                        22

<210> SEQ ID NO 335
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 335
uacaguagaa acuuccaucu gg                                        22

<210> SEQ ID NO 336
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 336
uauacaguag aaacuuccau gg                                        22

<210> SEQ ID NO 337

```
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 337
ucuauacagu agaaacuucc gg                                              22

<210> SEQ ID NO 338
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 338
uucuauacag uagaaacuuc gg                                              22

<210> SEQ ID NO 339
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 339
uuucuauaca guagaaacuu gg                                              22

<210> SEQ ID NO 340
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 340
uuuucuauac aguagaaacu gg                                              22

<210> SEQ ID NO 341
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 341
uggugauuuc uauacaguag gg                                              22

<210> SEQ ID NO 342
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 342
uaauggugau uucuauacag gg                                              22

<210> SEQ ID NO 343
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 343
```
uaaauggtag uugucaugac gg                                        22

<210> SEQ ID NO 344
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 344
uuaaaaaaau gguaguuguc gg                                        22

<210> SEQ ID NO 345
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 345
ugaguuuuag acauccaacu gg                                        22

<210> SEQ ID NO 346
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 346
uugaguuuua gacauccaac gg                                        22

<210> SEQ ID NO 347
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 347
uuacuugagu uuuagacauc gg                                        22

<210> SEQ ID NO 348
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 348
uacaaggcuu uacacuuauc gg                                        22

<210> SEQ ID NO 349
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 349
uuacaaggcu uuacacuuau gg                                        22

<210> SEQ ID NO 350
<211> LENGTH: 22
<212> TYPE: RNA

```
<213> ORGANISM: Artificial Sequence
<220> FEATURE:
<223> OTHER INFORMATION: Synthetic Polynucleotide

<400> SEQUENCE: 350
uucaucuuca guuacaaggc gg                                              22

<210> SEQ ID NO 351
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 351
uuaaaauagu uucuauacac gg                                              22

<210> SEQ ID NO 352
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 352
uugaugucaa caaagucuuu gg                                              22

<210> SEQ ID NO 353
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 353
uaguuuuaaa aagcaucuuc gg                                              22

<210> SEQ ID NO 354
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 354
uuaguuuuaa aaagcaucuu gg                                              22

<210> SEQ ID NO 355
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 355
uaacuaauca gcaauagcuc gg                                              22

<210> SEQ ID NO 356
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 356
ucagcaaaca uuaacaacac gg                                              22
```

```
<210> SEQ ID NO 357
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 357
uuacagcaaa cauuaacaac gg                                              22

<210> SEQ ID NO 358
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 358
uaauacagca aacauuaaca gg                                              22

<210> SEQ ID NO 359
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 359
uaaauacagc aaacauuaac gg                                              22

<210> SEQ ID NO 360
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 360
uuaaauacag caaacauuaa gg                                              22

<210> SEQ ID NO 361
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 361
utcguauaag cugcaucaga ga                                              22

<210> SEQ ID NO 362
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 362
utucguauaa gctgcatcag ag                                              22

<210> SEQ ID NO 363
<211> LENGTH: 36
<212> TYPE: RNA
<213> ORGANISM: Artificial Sequence
<220> FEATURE:
```

<223> OTHER INFORMATION: Synthetic Polynucleotide

<400> SEQUENCE: 363
ucugaaugcu ucuaaguaaa gcagccgaaa ggcugc                36

<210> SEQ ID NO 364
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 364
cugaaugcuu cuaaguaaaa gcagccgaaa ggcugc                36

<210> SEQ ID NO 365
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 365
gaaugcuucu aaguaaauaa gcagccgaaa ggcugc                36

<210> SEQ ID NO 366
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 366
uacuuagaag cauucagaau gg                22

<210> SEQ ID NO 367
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 367
uuacuuagaa gcauucagaa gg                22

<210> SEQ ID NO 368
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 368
uuuacuuaga agcauucaga gg                22

<210> SEQ ID NO 369
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 369
uuuuacuuag aagcauucag gg                22

-continued

```
<210> SEQ ID NO 370
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 370
uuauuuacuu agaagcauuc gg                                              22

<210> SEQ ID NO 371
<211> LENGTH: 4273
<212> TYPE: DNA
<213> ORGANISM: Homo sapiens

<400> SEQUENCE: 371
gccaatagga gccgcgctgg ctggagagta atgttacaga gcggagagag tgaggaggct     60
gcgtctggct cccgctctca cagccattgc agtacattga gctccataga gacagcgccg    120
gggcaagtga gagccggacg ggcactgggc gactctgtgc ctcgctgagg aaaaataact    180
aaacatgggc aaaggagatc ctaagaagcc gagaggcaaa atgtcatcat atgcattttt    240
tgtgcaaact tgtcgggagg agcataagaa gaagcaccca gatgcttcag tcaacttctc    300
agagttttct aagaagtgct cagagaggtg gaagaccatg tctgctaaag agaaaggaaa    360
atttgaagat atggcaaaag cggacaaggc ccgttatgaa agagaaatga aaacctatat    420
ccctcccaaa ggggagacaa aaagaagtt caaggatccc aatgcaccca gaggcctcc     480 ttcggccttc ttcctcttct gctctgagta tcgcccaaaa atcaaaggag aacatcctgg    540
cctgtccatt ggtgatgttg cgaagaaact gggagagatg tggaataaca ctgctgcaga    600
tgacaagcag ccttatgaaa agaaggctgc gaagctgaag gaaaaatacg aaaaggatat    660
tgctgcatat cgagctaaag aaagcctga tgcagcaaaa aagggagttg tcaaggctga    720
aaaaagcaag aaaaagaagg aagaggagga agatgaggaa gatgaagagg atgaggagga    780
ggaggaagat gaagaagatg aagatgaaga agaagatgat gatgatgaat aagttggttc    840
tagcgcagtt ttttttttct tgtctataaa gcatttaacc cccctgtaca caactcactc    900
cttttaaaga aaaaaattga atgtaaggc tgtgtaagat ttgttttaa actgtacagt     960 gtctttttt gtatagttaa cacactaccg aatgtgtctt tagatagccc tgtcctggtg   1020
gtattttcaa tagccactaa ccttgcctgg tacagtatgg gggttgtaaa ttggcatgga   1080
aatttaaagc aggttcttgt tggtgcacag cacaaattag ttatatatgg ggatggtagt   1140
tttttcatct tcagttgtct ctgatgcagc ttatacgaaa taattgttgt tctgttaact   1200
gaataccact ctgtaattgc aaaaaaaaaa aaaagttgc agctgttttg ttgacattct    1260
gaatgcttct aagtaaatac aattttttt attagtattg ttgtcctttt cataggtctg    1320 aaattttct tcttgagggg aagctagtct tttgcttttg cccatttga atcacatgaa     1380 ttattacagt gttatatcctt tcatatagtt agctaataaa aagcttttgt ctacacaccc   1440
tgcatatcat aatgggggta aagttaagtt gagatagttt tcatccataa ctgaacatcc   1500
aaaatcttga tcagttaaga aatttcacat agcccactta catttacaaa ctgaagagta   1560
atcaatctac tcaaagcatg ggattattag aatcaaacat tttgaaagtc tgtccttgaa   1620
ggactaatag aaaagtatgt tctaacctt acatgaggac tctattcttt aactcccatt    1680
accatgtaat ggcagttata ttttgcagtt cccacattaa agaagacctg agaatgtatc   1740
cccaaaagcg tgagcttaaa atacaagact gccatattaa atttttgtt gacattagtc    1800
```

```
tcagtgaaga ctatgaaaat gctggctata gatgtcttttt cccatttatc taaatatgga    1860
ctgctcagga aacgagactt tccattacaa gtattttttaa ttaattgggc cagcttttca    1920
aacaaagatg ccacattcaa aatagggtat atttttcctat attacggttt gccccttat     1980 aaatccaagt agataggaag aaagaagaca aactttgcat ctcagtatga attattcaat    2040
ttatttgaat gattttttctt tacaaaacaa actcattcat tagtcatgtt tatctgctta    2100
ggagtttagg gaacaatttg gcaattttgt ggttttcgag attatcgttt tcttaaagtg    2160
ccagtatttt aaaatagcgt tcttgtaatt ttacacgctt ttgtgatgga gtgctgtttt    2220
gttatataat ttagacttgg attctttcca tttgcatttg tttatgtaat tcaggagga     2280 atactgaaca tctgagtcct ggatgatact aataaactaa taattgcaga ggttttaaat    2340
actagttaaa tggctttcac ttaagaactt aagattttgt tacatatttt taaatcttgt    2400
ttctaataat acctcttagc agtacctttt aaataagtat aagggatggc aaagttttc     2460 cctttaaaaa tactcacttt atgcttataa ataggttaat gggctgataa aaggttttgt    2520
caaacattgc aagtattcgg tgctatatat aaaggaggaa aaactagttt tactttcaga    2580
atgatttaaa caagattttt aaaaacaaga tacatgcaag cgaacagcag ggttagtgat    2640
aggctgcaat tgtgtcgaac atcagatttt ttgttaagag gagcaaatga ctcaatctga    2700
tttagatgga agtttctact gtatagaaat caccattaat caccaacatt aataattctg    2760
atccatttaa aatgaattct ggctcaagga gaatttgtaa ctttagtagg tacgtcatga    2820
caactaccat tttttttaaga tgttgagaat gggaacagtt tttttagggt ttattcttga    2880
ccacagatct taagaaaatg gacaaaaccc ctcttcaatc tgaagattag tatggtttgg    2940
tgttctaaca gtatcccta gaagttggat gtctaaaact caagtaaatg gaagtgggag    3000
gcaatttaga taagtgtaaa gccttgtaac tgaagatgat ttttttttaga aagtgtatag    3060 aaactatttt aatgccaaga tagttacagt gctgtggggt taaagacttt tgttgacatc    3120
aagaaaagac taaatctata attaattggg ccaactttta aaatgaagat gcttttttaaa    3180 actaatgaac taagatgtat aaatcttagt tttttttgtat tttaaagata ggcatatggc    3240
atattgatta acgagtcaaa tttcctaact ttgctgtgca aaggttgaga gctattgctg    3300
attagttacc acagttctga tgatcgtccc atcacagtgt tgttaatgtt tgctgtatttt    3360 attaattttc ttaaagtgaa atctgaaaaa tgaaatttgt gtgtcctgtg tacccgaggg    3420
gtaatgatta aatgataaag ataagaaaag cgcccatgta acacaaactg ccattcaaca    3480
ggtatttccc ttactaccta aggaattgta accattgctc agacattgta ggatttaact    3540
atgttgaaaa ctacaggaga ggccgggcgc agtggctcac gcctgtaatc ccagcacttt    3600
gggaggccaa gcgggcaga tcacgaggtc aggagattga gaccatcctg gctaacgtgg    3660
tgaaaccccg cctctactaa aaatacaaaa aattagccaa gcgtggtgct gggcgcctgt    3720
agtcccagta actcaggagg ctgaggcagg agaatggcgt gaacccggga ggcggaggtt    3780
gcagtgagcc gagattgtgc cactgcactc cagcctgggt gacagagcaa gactccatct    3840
caaaaaaaaa aaaaaaacac aggagagaca actggttttt gaatgaaata catgggtact    3900
gccttgcttg acatcacata gtccttgatg aaagttcaca tttaggtctg cttggtacaa    3960
tacgcctcct aaaaaggtcc ttgatgaaag ttcacattta ggtctgcttg gtacaacacg    4020
cctcctgaaa gggtctgata gctttcagta gcagtaagac acttgcatgt gatggtaagg    4080
tatctgcaaa tttgcacaca ccgtacacag cttaagtctt agaattaact tgctaaaatg    4140
tgagcctttg gtaattaggc tgtttttatta gggagtgtga taatatttga atttcttttc    4200
```

| | |
|---|---|
| atatttgtgc tttgtgtcat tttcaaatga cccttgaaat gtattttaaa agtagataaa | 4260 |
| agccagaaag tga | 4273 |

<210> SEQ ID NO 372
<211> LENGTH: 2323
<212> TYPE: DNA
<213> ORGANISM: Macaca fascicularis

<400> SEQUENCE: 372

| | |
|---|---|
| aatgttacag agcggagaga gtgaggaggc tgcgtctggc tcccgctctc acagccattg | 60 |
| cagtacattg agctccatag agacagcgcc ggggcaagtg agagccggac gggcactggg | 120 |
| cgactctgtg cctcgctgag gaaaaataac taaacatggg caaaggagat cctaagaagc | 180 |
| cgagaggcaa aatgtcatca tatgcatttt ttgtgcaaac ttgtcgggag gagcataaga | 240 |
| agaagcaccc agatgcttca gtcaacttct cagagttttc taagaagtgc tcagagaggt | 300 |
| ggaagaccat gtctgctaaa gagaaaggaa aatttgaaga tatggcaaag gcggacaagg | 360 |
| cccgttacga aagagaaatg aaaacctata tccctcccaa aggggagaca aaaaagaagt | 420 |
| tcaaggatcc caatgcaccc aagaggcctc cttcggcctt cttcctgttc tgctctgagt | 480 |
| atcgcccaaa aatcaaagga gaacatcctg gcctgtccat tggtgatgtt gcgaagaaac | 540 |
| tgggagagat gtggaataac actgctgcag atgacaagca gccttatgaa aagaaggctg | 600 |
| cgaagctgaa ggaaaaatac gaaaaggata ttgctgcata tcgagctaaa ggaaagcctg | 660 |
| atgcagcaaa aaagggagtt gtcaaggctg aaaaaagcaa gaaaaagaag gaagaggagg | 720 |
| aagatgagga agatgaagag gatgaggagg aggaggaaga tgaagaagat gaagatgaag | 780 |
| aagaagatga tgatgatgaa taagttggtt ctagcgcagt ttttttttc ttgtctataa | 840 |
| agcatttaac ccccctgtac acaactcact ccttttaaag aaaaaaattg aaatgtaagg | 900 |
| ctgtgtaaga tttgttttta aactgtacag tgtcttttt tgtatagtta acacactacc | 960 |
| gaatgtgtct ttacatagcc ctgtcctggt ggtattttca atagccacta accttgcctg | 1020 |
| gtacagtatg ggggttgtaa attggcatgg aaatttaaag caggttcttg ttggtgcaca | 1080 |
| gcacaaatta gttatatatg gggatggtag ttttttcatc ttcagttgtc tctgatgcag | 1140 |
| cttatacgaa ataattgttg ttctgttaac tgaataccac tctgtaattg caaaaaaaaa | 1200 |
| aaaaaaagtt gcagctgttt tgttgacatt ctgaatgctt ctaagtaaat acaatttttt | 1260 |
| ttattagtat tgttgtcctt ttcataggtc tgaaattttt cttcttgagg ggaagctagt | 1320 |
| cttttgcttt tgcccatttt gaatcacatg aattattaca gtgtttatcc tttcatatag | 1380 |
| ttagctaata aaaagctttt gtctacacac cctgcatacc ataatggggg taaagttaag | 1440 |
| ttgagatagt tttcatccat aactgaacat cgaaaatctt gatcagttaa gaaatttcac | 1500 |
| atagcccact tacatttaca aactgaagag taatcagtct actcaaagca tgggattatt | 1560 |
| agaatcaaac attttgaaag tctgtccttg aaggactaat agaaaagtat gttctaacct | 1620 |
| ttacatgagg actctattct ttaactccca ttaccatgta atggcagtta tattttgcag | 1680 |
| ttcccacatt aaagaagacc tgagaatgta tccccaaaag cgtgagctta aaatacaaga | 1740 |
| ttgccatatt aaattttttg ttgacattag tctcagtgaa gactatgaaa atgctggcta | 1800 |
| tagatgtctt ttcccatttta tctcaatatg gactgctcag gaaacgagac tttccattac | 1860 |
| aagtattttt aattaattgg gccagctttt aaaatgaaga tgcccacattc aaaataggg t | 1920 |
| gtattttcct atattatggt ttgccccttt ataaatcgaa gtagatagga ggaaagaaga | 1980 |

| | |
|---|---:|
| cacttaaact ttgcatctca gtatgaatta ttcaattgat ttgaatgatt tttcttttaca | 2040 |
| aaacaaactc attagtcatt atctgcttag cagtttaggg aacaatttgg caattttgtg | 2100 |
| gttttttcgag attatcgttt tcttaaagtg ccagtatttt aaaatagcgt tcttgtaatt | 2160 |
| ttacacgctt ttgtgatgga gtgctgtttt gttatataat tttgacttgg attcttccca | 2220 |
| tttgcatttg tttatgtaat ttcaggagga atactgaaca tctgagtcct ggatgatact | 2280 |
| aataaactaa taattgcaga ggttttaaaa aaaaaaaaa aaa | 2323 |

<210> SEQ ID NO 373
<211> LENGTH: 2855
<212> TYPE: DNA
<213> ORGANISM: Mus musculus

<400> SEQUENCE: 373

| | |
|---|---:|
| cgcgctggct ggagagtaat gttacagagc ggagagagtg aggaggctgc gtctggctcc | 60 |
| cgctctcaca gccattgcag tacattgagc tccatagaga cagcgccggg gcaagcgcga | 120 |
| gccggacggg cactgggcga ctctgtgcct cgcggaggaa aatcaactaa acatgggcaa | 180 |
| aggagatcct aaaaagccga gaggcaaaat gtcctcatat gcattctttg tgcaaacttg | 240 |
| ccgggaggag cacaagaaga agcacccgga tgcttctgtc aacttctcag agttctccaa | 300 |
| gaagtgctca gagaggtgga agaccatgtc tgctaaagaa aaggggaaat ttgaagatat | 360 |
| ggcaaaggct gacaaggctc gttatgaaag agaaatgaaa acctacatcc cccccaaagg | 420 |
| ggagaccaaa aagaagttca aggaccccaa tgcacccaag aggcctcctt cggccttctt | 480 |
| cttgttctgt tctgagtacc gccccaaaat caaaggcgag catcctggct tatccattgg | 540 |
| tgatgttgca aagaaactag gagagatgtg gaacaacact gcagcagatg acaagcagcc | 600 |
| ctatgagaag aaagctgcca agctgaagga gaagtatgag aaggatattg ctgcctacag | 660 |
| agctaaagga aaacctgatg cagcgaaaaa gggggtggtc aaggctgaaa agagcaagaa | 720 |
| aaagaaggaa gaggaagatg atgaggagga tgaagaggat gaggaagagg aggaagaaga | 780 |
| ggaagacgaa gatgaagaag aagatgatga tgatgaataa gttggttcta gcgcagtttt | 840 |
| ttttttcttgt ctataaagca tttaacccc ctgtacacaa ctcactcctt ttaaagaaaa | 900 |
| aaattgaaat gtaaggctgt gtaagatttg tttttaaact gtacagtgtc tttttttgta | 960 |
| tagttaacac actaccgaat gtgtctttag atagccctgt cctggtggta ttttcaatag | 1020 |
| ccactaacct tgcctggtac agtctggggg ttgtaaattg gcatggaaat ttaaagcagg | 1080 |
| ttcttgttgg tgcacagcac aaattagtta tatatgggga cagtagtttg gttttttgtt | 1140 |
| tttttttttt tttcttttgg ttttcttttt gggtttatt ttttcatct tcagttgtct | 1200 |
| ctgatgcagc ttatacgaag ataattgttg ttctgttaac tgaataccac tctgtaattg | 1260 |
| caaaaaaaaa attgcggctg ttttgttgac attctgaatg cttctaagta aatacaattt | 1320 |
| tttttattag tattgttgtc cttttcatag gtctgaaagt tttcttctca aggggaagct | 1380 |
| agtcttttgc tttgcccatt ttgggtcaca tggattatta gtgtgttatc tttcatctag | 1440 |
| ttagctggaa gagagctttt gtccacatgc cctgccattg tggtagggta acattttcat | 1500 |
| ccatagttga agaatctcct aaatcgtgat agttggataa gagatattat ataacctact | 1560 |
| tggcaaagca aggagtgatc aatactgtca caccgtggga ctattaggat caagcaatct | 1620 |
| gaacgtctgt ccttgaagga ctgatagaaa agtaccttct aatccttaca cgaggactct | 1680 |
| cctttaaccg ccattactgt gtaatgacag ttatattttg cagtttcccc tactaaagaa | 1740 |
| gacctgagaa tgtatcccca aaagtgtgag cttaaaatac aagactgctg tactatttgt | 1800 |

```
tgaccttagt cccagcgaag gctatcacaa gaacgctggc tgtaaagcct ttgcccttct    1860
atctagatat ggattgctca ggaaacttga ctgtttaaag gtattttttaa ttacttgagc   1920 cagcttttaa aattatgcca catttaaaat gaagggtata ttttcctata ctgtggtttg    1980 tcccttatg aatcagatac aagaggataa actttgcata ttagtaccat ttgtccaata     2040
catttgcttt ttcttatata aacccaaact cattcattaa tcaggtttaa tctgcttagt    2100
ttagggaaca atttggcaat tttgtggatt tttttttgag attatcgttc tcttaaagtg    2160
ccagtgtttt aaatagcgtt cttgtaattt cacgcgcttt tgtgatggag tgctgttata    2220
taattttgac ttgggttctt tacatttgcg ttgttaatgt aatttgagga ggaatactga    2280
acatgagtcc tggatgatac taataaacta ataattacag aggttttaaa tattagttaa    2340
atgactttca cttaagaatt taagcttttg gtcacacttt ataatagtgc cttatatgat    2400
aaacaactga aaggctcttt cccattaaca acccttgatg ctggggccag tgagatagtg    2460
ggtaaaaagg cagttggctg ccaaccctga caaccgatgg caaaaggagg gaaccagctt    2520
ccaaaatgct ttgaccaaat gctccctcca ttcatgaaca cagttttaaa atgttaaata    2580
ggctagaggg cagtaaaaac aggttttttt atcgagcatc cctaatctat acatatgagg    2640
agccataatc tgaatgttaa gtgaaaagcg aggttggtct taaagattgc acgtgtgttc    2700
ttaagcctgt agaggacctc cgcaggccgt aatggtctcg attaccaact taagaacaag    2760
tgactggctt ggaaacttgt actgttgctt tagaactacc attgtggaca tctgttgtta    2820
gtaagtgatc catttaaaag tgaactctgc ctcaa                               2855
```

<210> SEQ ID NO 374
<211> LENGTH: 31
<212> TYPE: DNA
<213> ORGANISM: Homo sapiens

<400> SEQUENCE: 374

```
taagatttgt ttttaaactg tacagtgtct t                                    31
```

<210> SEQ ID NO 375
<211> LENGTH: 31
<212> TYPE: DNA
<213> ORGANISM: Homo sapiens

<400> SEQUENCE: 375

```
ttggtgcaca gcacaaatta gttatatatg g                                    31
```

<210> SEQ ID NO 376
<211> LENGTH: 56
<212> TYPE: DNA
<213> ORGANISM: Homo sapiens

<400> SEQUENCE: 376

```
tctgatgcag cttatacgaa ataattgttg ttctgttaac tgaataccac tctgta         56
```

<210> SEQ ID NO 377
<211> LENGTH: 41
<212> TYPE: DNA
<213> ORGANISM: Homo sapiens

<400> SEQUENCE: 377

```
aaaaaagttg cagctgtttt gttgacattc tgaatgcttc t                         41
```

<210> SEQ ID NO 378

```
<211> LENGTH: 31
<212> TYPE: DNA
<213> ORGANISM: Homo sapiens

<400> SEQUENCE: 378
tgagatagtt ttcatccata actgaacatc c                                    31

<210> SEQ ID NO 379
<211> LENGTH: 31
<212> TYPE: DNA
<213> ORGANISM: Homo sapiens

<400> SEQUENCE: 379
taccatgtaa tggcagttat attttgcagt t                                    31

<210> SEQ ID NO 380
<211> LENGTH: 31
<212> TYPE: DNA
<213> ORGANISM: Homo sapiens

<400> SEQUENCE: 380
tttacacgct tttgtgatgg agtgctgttt t                                    31

<210> SEQ ID NO 381
<211> LENGTH: 31
<212> TYPE: DNA
<213> ORGANISM: Homo sapiens

<400> SEQUENCE: 381
aatactgaac atctgagtcc tggatgatac t                                    31
```